United States Patent
Goldenberg et al.

(10) Patent No.: US 10,744,129 B2
(45) Date of Patent: *Aug. 18, 2020

(54) THERAPY OF SMALL-CELL LUNG CANCER (SCLC) WITH A TOPOISOMERASE-I INHIBITING ANTIBODY-DRUG CONJUGATE (ADC) TARGETING TROP-2

(71) Applicant: Immunomedics, Inc., Morris Plains, NJ (US)

(72) Inventors: David M. Goldenberg, Mendham, NJ (US); Serengulam V. Govindan, Summit, NJ (US)

(73) Assignee: Immunomedics, Inc., Morris Plains, NJ (US)

(*) Notice: Subject to any disclaimer, the term of this patent is extended or adjusted under 35 U.S.C. 154(b) by 71 days.

This patent is subject to a terminal disclaimer.

(21) Appl. No.: 15/901,691

(22) Filed: Feb. 21, 2018

(65) Prior Publication Data

US 2018/0185351 A1 Jul. 5, 2018

Related U.S. Application Data

(60) Continuation-in-part of application No. 15/820,708, filed on Nov. 22, 2017, now Pat. No. 10,413,539, (Continued)

(51) Int. Cl.
| | | |
|---|---|---|
| *A61K 31/4745* | (2006.01) | |
| *A61K 47/68* | (2017.01) | |
| *C07K 16/30* | (2006.01) | |
| *A61B 6/00* | (2006.01) | |
| *C07K 16/32* | (2006.01) | |
| *A61K 31/337* | (2006.01) | |
| *A61K 31/4184* | (2006.01) | |
| *A61K 31/4375* | (2006.01) | |
| *A61K 31/513* | (2006.01) | |
| *A61K 31/675* | (2006.01) | |
| *A61K 31/7088* | (2006.01) | |
| *A61K 31/713* | (2006.01) |

(Continued)

(52) U.S. Cl.
CPC ........... *A61K 31/4745* (2013.01); *A61B 6/481* (2013.01); *A61K 31/337* (2013.01); *A61K 31/4184* (2013.01); *A61K 31/4375* (2013.01); *A61K 31/454* (2013.01); *A61K 31/513* (2013.01); *A61K 31/555* (2013.01); *A61K 31/675* (2013.01); *A61K 31/7088* (2013.01); *A61K 31/713* (2013.01); *A61K 33/24* (2013.01); *A61K 39/39558* (2013.01); *A61K 47/6803* (2017.08); *A61K 47/6851* (2017.08); *A61K 47/6853* (2017.08); *A61P 35/04* (2018.01); *C07K 16/2803* (2013.01); *C07K 16/2833* (2013.01); *C07K 16/2887* (2013.01); *C07K 16/30* (2013.01); *C07K 16/303* (2013.01); *C07K 16/3007* (2013.01); *C07K 16/3015* (2013.01); *C07K 16/3023* (2013.01); *C07K 16/3061* (2013.01); *C07K 16/3092* (2013.01); *C07K 16/32* (2013.01); *A61K 45/06* (2013.01); *A61K 2039/505* (2013.01); *A61K 2039/507* (2013.01); *A61K 2039/545* (2013.01); *A61K 2039/55* (2013.01); *A61K 2300/00* (2013.01); *C07K 2317/24* (2013.01); *C07K 2317/73* (2013.01); *C07K 2317/77* (2013.01); *C07K 2317/92* (2013.01); *C07K 2317/94* (2013.01)

(58) Field of Classification Search
CPC ............ A61K 47/6803; A61K 47/6851; A61K 31/4745
USPC ....................................................... 424/181.1
See application file for complete search history.

(56) References Cited

U.S. PATENT DOCUMENTS

| | | | |
|---|---|---|---|
| 4,036,945 | A | 7/1977 | Haber |
| 4,046,722 | A | 9/1977 | Rowland |

(Continued)

FOREIGN PATENT DOCUMENTS

| | | |
|---|---|---|
| EP | 0253202 | 1/1988 |
| EP | 0306943 | 3/1989 |

(Continued)

OTHER PUBLICATIONS

US 6,558,648 B1, 05/2003, Griffiths et al. (withdrawn)

(Continued)

*Primary Examiner* — Yan Xiao
(74) *Attorney, Agent, or Firm* — Richard A. Nakashima

(57) ABSTRACT

The present invention relates to treatment of SCLC with therapeutic ADCs comprising a drug attached to an anti-Trop-2 antibody or antigen-binding antibody fragment. Preferably, the drug is SN-38. More preferably, the antibody is an hRS7 antibody and the ADC is sacituzumab govitecan. The ADC may be administered at a dosage of between 4 mg/kg and 16 mg/kg, preferably 4, 6, 8, 9, 10, 12, or 16 mg/kg, mostly preferably 8 to 10 mg/kg. When administered at specified dosages and schedules, the ADC can reduce solid tumors in size, reduce or eliminate metastases and is effective to treat cancers resistant to standard therapies, such as radiation therapy, chemotherapy or immunotherapy. Surprisingly, the ADC is effective to treat cancers that are refractory to or relapsed from irinotecan or topotecan. Preferably, the ADC is administered as a combination therapy with one or more other anti-cancer treatments, such as carboplatin or cisplatinum.

13 Claims, 20 Drawing Sheets
Specification includes a Sequence Listing.

Related U.S. Application Data which is a continuation-in-part of application No. 15/069,208, filed on Mar. 14, 2016, now Pat. No. 10,137,196, which is a continuation-in-part of application No. 14/667,982, filed on Mar. 25, 2015, now Pat. No. 9,493,573, which is a division of application No. 13/948,732, filed on Jul. 23, 2013, now Pat. No. 9,028,833.

(60) Provisional application No. 62/463,316, filed on Feb. 24, 2017, provisional application No. 62/428,655, filed on Dec. 1, 2016, provisional application No. 62/241,881, filed on Oct. 15, 2015, provisional application No. 62/156,608, filed on May 4, 2015, provisional application No. 62/138,092, filed on Mar. 25, 2015, provisional application No. 62/133,654, filed on Mar. 16, 2015, provisional application No. 62/133,729, filed on Mar. 16, 2015, provisional application No. 61/749,548, filed on Jan. 7, 2013, provisional application No. 61/736,684, filed on Dec. 13, 2012.

(51) Int. Cl.
| | | |
|---|---|---|
| *C07K 16/28* | (2006.01) | |
| *A61K 31/454* | (2006.01) | |
| *A61K 39/395* | (2006.01) | |
| *A61K 33/24* | (2019.01) | |
| *A61P 35/04* | (2006.01) | |
| *A61K 31/555* | (2006.01) | |
| *A61K 39/00* | (2006.01) | |
| *A61K 45/06* | (2006.01) | |

(56) References Cited

U.S. PATENT DOCUMENTS

| | | |
|---|---|---|
| 4,200,690 A | 4/1980 | Root et al. |
| 4,331,647 A | 5/1982 | Goldenberg |
| 4,359,457 A | 11/1982 | Neville et al. |
| 4,699,784 A | 10/1987 | Shih et al. |
| 4,704,692 A | 11/1987 | Ladner |
| 4,816,567 A | 3/1989 | Cabilly et al. |
| 4,824,659 A | 4/1989 | Howthorne |
| 4,916,213 A | 4/1990 | Scannon et al. |
| 4,918,163 A | 4/1990 | Young et al. |
| 4,925,922 A | 5/1990 | Byers et al. |
| 4,932,412 A | 6/1990 | Goldenberg |
| 4,946,778 A | 8/1990 | Ladner et al. |
| 5,057,313 A | 10/1991 | Shih et al. |
| 5,106,955 A | 4/1992 | Endo et al. |
| 5,112,954 A | 5/1992 | Abrams et al. |
| 5,122,368 A | 6/1992 | Greenfield et al. |
| 5,134,075 A | 7/1992 | Hellstrom et al. |
| 5,171,665 A | 12/1992 | Hellstrom et al. |
| 5,196,337 A | 3/1993 | Ochi et al. |
| 5,204,095 A | 4/1993 | Goodall et al. |
| 5,229,275 A | 7/1993 | Goroff |
| 5,443,953 A | 8/1995 | Hansen et al. |
| 5,484,892 A | 1/1996 | Tedder et al. |
| 5,525,338 A | 6/1996 | Goldenberg |
| 5,565,215 A | 10/1996 | Gref et al. |
| 5,567,610 A | 10/1996 | Borrebaeck et al. |
| 5,593,676 A | 1/1997 | Bhat et al. |
| 5,618,920 A | 4/1997 | Robinson et al. |
| 5,620,708 A | 4/1997 | Amkraut et al. |
| 5,633,425 A | 5/1997 | Lonberg et al. |
| 5,679,640 A | 10/1997 | Gaeta et al. |
| 5,686,072 A | 11/1997 | Uhr et al. |
| 5,693,762 A | 12/1997 | Queen et al. |
| 5,698,178 A | 12/1997 | Goldenberg |
| 5,702,727 A | 12/1997 | Amkraut et al. |
| 5,708,146 A | 1/1998 | Willner et al. |
| 5,716,595 A | 2/1998 | Goldenberg |
| 5,736,119 A | 4/1998 | Goldenberg et al. |
| 5,750,105 A | 5/1998 | Newman et al. |
| 5,776,456 A | 7/1998 | Anderson et al. |
| 5,789,554 A | 8/1998 | Leung et al. |
| 5,792,845 A | 8/1998 | O'Reilly et al. |
| 5,795,967 A | 8/1998 | Aggarwal et al. |
| 5,798,554 A | 8/1998 | Grimaldi et al. |
| 5,817,307 A | 10/1998 | Cummins |
| 5,824,701 A | 10/1998 | Greenwald et al. |
| 5,874,540 A | 2/1999 | Hansen et al. |
| 5,922,302 A | 7/1999 | Goldenberg et al. |
| 6,051,228 A | 4/2000 | Aruffo et al. |
| 6,051,230 A | 4/2000 | Thorpe et al. |
| 6,056,973 A | 5/2000 | Allen et al. |
| 6,077,499 A | 6/2000 | Griffiths et al. |
| 6,096,289 A | 8/2000 | Goldenberg |
| 6,156,754 A | 12/2000 | Lerchen et al. |
| 6,165,440 A | 12/2000 | Esenaliev |
| 6,183,744 B1 | 2/2001 | Goldenberg |
| 6,187,287 B1 | 2/2001 | Leung et al. |
| 6,201,104 B1 | 3/2001 | MacDonald et al. |
| 6,214,345 B1 | 4/2001 | Firestone et al. |
| 6,254,868 B1 | 7/2001 | Leung et al. |
| 6,306,393 B1 | 10/2001 | Goldenberg |
| 6,331,175 B1 | 12/2001 | Goldenberg |
| 6,379,698 B1 | 4/2002 | Leamon |
| 6,387,350 B2 | 5/2002 | Goldenberg |
| 6,395,276 B1 | 5/2002 | Rybak et al. |
| 6,530,944 B2 | 3/2003 | West et al. |
| 6,562,318 B1 | 5/2003 | Filler |
| 6,653,104 B2 | 11/2003 | Goldenberg |
| 6,716,821 B2 | 4/2004 | Zhao et al. |
| 7,018,809 B1 | 5/2006 | Carter |
| 7,074,403 B1 | 7/2006 | Goldenberg et al. |
| 7,122,636 B1 | 10/2006 | Hsei et al. |
| 7,151,164 B2 | 12/2006 | Hansen et al. |
| 7,238,785 B2 | 7/2007 | Govindan et al. |
| 7,312,318 B2 | 12/2007 | Hansen et al. |
| 7,387,779 B2 | 6/2008 | Kalluri |
| 7,585,491 B2 | 9/2009 | Govindan et al. |
| 7,591,994 B2 | 9/2009 | Govindan et al. |
| 7,772,373 B2 | 8/2010 | Hansen et al. |
| 7,820,161 B1 | 10/2010 | Curd et al. |
| 7,910,103 B2 | 3/2011 | Goldenberg |
| 7,931,903 B2 | 4/2011 | Hansen et al. |
| 7,999,083 B2 | 8/2011 | Govindan et al. |
| 8,080,250 B1 | 12/2011 | Govindan et al. |
| 8,119,101 B2 | 2/2012 | Byrd et al. |
| 8,268,317 B2 | 9/2012 | Govindan et al. |
| 8,268,319 B2 | 9/2012 | Govindan et al. |
| 8,420,086 B2 | 4/2013 | Govindan et al. |
| 8,425,912 B2 | 4/2013 | Govindan et al. |
| 8,658,773 B2 | 2/2014 | Zeng et al. |
| 9,028,833 B2 | 5/2015 | Govindan et al. |
| 9,180,205 B2 | 11/2015 | Zeng et al. |
| 9,492,566 B2 | 11/2016 | Goldenberg et al. |
| 9,707,302 B2 * | 7/2017 | Goldenberg ....... A61K 47/6853 |
| 9,770,517 B2 * | 9/2017 | Govindan .......... A61K 47/6803 |
| 10,130,626 B2 * | 11/2018 | Govindan ............ A61K 31/454 |
| 10,137,196 B2 * | 11/2018 | Govindan .......... C07K 16/2887 |
| 10,195,175 B2 * | 2/2019 | Goldenberg ....... A61K 47/6851 |
| 10,266,605 B2 * | 4/2019 | Govindan .......... A61K 47/6801 |
| 2001/0034363 A1 | 10/2001 | Li et al. |
| 2002/0018749 A1 | 2/2002 | Hudson et al. |
| 2003/0103979 A1 | 6/2003 | Leung et al. |
| 2003/0133972 A1 | 7/2003 | Danthi et al. |
| 2004/0001838 A1 | 1/2004 | Zhao et al. |
| 2004/0076683 A1 | 4/2004 | Hoarau et al. |
| 2006/0142506 A1 | 6/2006 | Breitenkamp et al. |
| 2006/0193865 A1 | 8/2006 | Govindan et al. |
| 2007/0142331 A1 | 6/2007 | Zhang et al. |
| 2007/0212350 A1 | 9/2007 | Govindan et al. |
| 2008/0166363 A1 | 7/2008 | Govindan et al. |
| 2010/0104589 A1 | 4/2010 | Govindan et al. |
| 2010/0196266 A1 | 8/2010 | Goldenberg et al. |
| 2011/0070156 A1 | 3/2011 | Govindan et al. |
| 2011/0160159 A1 | 6/2011 | Ryan |
| 2011/0256053 A1 | 10/2011 | Chang et al. |

(56) References Cited

U.S. PATENT DOCUMENTS

| | | |
|---|---|---|
| 2011/0274704 A1 | 11/2011 | Chang et al. |
| 2011/0305631 A1 | 12/2011 | Govindan et al. |
| 2012/0082617 A1 | 4/2012 | Govindan et al. |
| 2012/0328564 A1 | 12/2012 | Govindan et al. |
| 2013/0090458 A1 | 4/2013 | Govindan et al. |
| 2013/0177526 A1 | 7/2013 | Govindan et al. |
| 2013/0216561 A1 | 8/2013 | Govindan et al. |
| 2014/0004078 A1 | 1/2014 | Govindan et al. |
| 2014/0178294 A1 | 6/2014 | Zeng et al. |
| 2015/0132217 A1 | 5/2015 | Chang et al. |
| 2016/0032008 A1 | 2/2016 | Zeng et al. |
| 2016/0166567 A1 | 6/2016 | Ryan |
| 2016/0303253 A1 | 10/2016 | Govindan et al. |
| 2017/0014527 A1 | 1/2017 | Goldenberg et al. |

FOREIGN PATENT DOCUMENTS

| | | |
|---|---|---|
| EP | 0332865 | 9/1989 |
| EP | 0510949 | 10/1992 |
| WO | 90/09196 | 8/1990 |
| WO | 91/11465 | 8/1991 |
| WO | 91/13974 | 9/1991 |
| WO | 94/27638 | 12/1994 |
| WO | 9509917 | 4/1995 |
| WO | 96/04925 | 2/1996 |
| WO | 98/04281 | 2/1998 |
| WO | 98/42378 | 10/1998 |
| WO | 98/50435 | 11/1998 |
| WO | 99/02567 | 1/1999 |
| WO | 99/54440 | 10/1999 |
| WO | 00/29584 | 5/2000 |
| WO | 00/67795 | 11/2000 |
| WO | 00/67796 | 11/2000 |
| WO | 0074718 | 12/2000 |
| WO | 0076551 | 12/2000 |
| WO | 0124763 | 4/2001 |
| WO | 2004054622 | 7/2004 |
| WO | 2007123995 | 11/2007 |
| WO | 2012151199 | 11/2012 |

OTHER PUBLICATIONS

Tang et al. (Cancer Chemother Pharmacol, published online: Aug. 31, 2010, 67: 1389-1400).*
Beckman et al., "Antibody constructs in cancer therapy: protein engineering strategies to improve exposure in solid tumors", Cancer. Jan. 15, 2007;109(2)170-9.
Berenbaum, MC., "Synergy, additivism and antagonism in immunosuppression. A critical review", Clin Exp Immunol. Apr. 1977;28(1):1-18.
Berenbaum, MC., "What is synergy?", Pharmacol Rev. Jun. 1989;41(2):93-141.
Cespedes et al., "Mouse models in oncogenesis and cancer therapy", Clin Transl Oncol. May 2006;8(5):318-29.
Dennis, C., "Cancer: off by a whisker", Nature. Aug. 17, 2006;442(7104):739-41.
Foran, JM., "Antibody-based therapy of non-Hodgkin's lymphoma", Best Pract Res Clin Haematol. Sep. 2002;15(3):449-65.
Fujimori et al., "A modeling analysis of monoclonal antibody percolation through tumors: a binding-site barrier", J Nucl Med. Jul. 1990;31(7):1191-8.
Lundberg et al., "Conjugation of an anti-B-cell lymphoma monoclonal antibody, LL2, to long-circulating drug-carrier lipid emulsions", J. Pharm. Pharmacol. 51(10):1099-105 (1999).
Mack et al., "A small bispecific antibody construct expressed as a functional single-chain molecule with high tumor cell cytotoxicity", Proc. Natl. Acad. Sci. USA 92:7021-7025 (1995).
Maloney et al., "Phase I clinical trial using escalating single-dose infusion of chimeric anti-CD20 monoclonal antibody (IDEC-C2B8) in patients with recurrent B-cell lymphoma", Blood 84(8):2457-66 (1994).
Maloney et al., "IDEC-C2B8 (Rituximab) anti-CD20 monoclonal antibody therapy in patients with relapsed low-grade non-Hodgkin's lymphoma", Blood. Sep. 15, 1997;90(6):2188-95.
Mason et al., "Value of monoclonal anti-CD22 (p135) antibodies for the detection of normal and neoplastic B lymphoid cells", Blood. Mar. 1987;69(3):836-40.
Mills et al., "Diagnostic imaging of non-Hodgkin's lymphoma with anti-lymphomas antibody labeled with Tc-99m", Proc Am Assoc Cancer Res 1993; 34:479, Abstract #2857.
Mole S. E., "Epitope Mapping", Methods in Molecular Biology, vol. 10: Immunochemical Protocols, Manson (Ed.), Humana Press, Inc. (1992).
Morrison et al., "Chimeric human antibody molecules: mouse antigen-binding domains with human constant region domains", Proc Natl Acad Sci USA Nov. 1984;81(21):6851-5.
Murthy et al., "Lymphoma imaging with a new technetium-99m labelled antibody, LL2", Eur J Nucl Med. 1992;19(6):394-401.
Ochakovskaya et al., Therapy of Disseminated B-Cell Lymphoma Xenografts in Severe Combined Immunodeficient Mice with an Anti-CD74 Antibody Conjugated with (111)Indium, (67)Gallium, or (90)Yttrium, Clin. Cancer Res. 7(6):1505-1510 (2001).
Orlandi et al., "Cloning immunoglobulin variable domains for expression by the polymerase chain reaction", Proc. Natl. Acad. Sci. USA 86:3833-3837 (1989).
Pastan et al., "Immunotoxins", Cell 47:641-648 (1986).
Pawlak-Byczkowska et al., "Two new monoclonal antibodies, EPB-1 and EPB-2, reactive with human lymphoma", Cancer Res. 49(16):4568-77 (1989).
Perrota et al., "Response of chronic relapsing ITP of 10 years duration to Rituximab", Blood, vol. 92(10 Suppl.), p. 88b, 1998, Abstract# 3360.
Press et al., "Radiolabeled-antibody therapy of B-cell lymphoma with autologous bone marrow support", N. Engl. J. Med. 329(17):1219-24 (1993).
Press et al., "Phase II trial of 131I-B1 (anti-CD20) antibody therapy with autologous stem cell transplantation for relapsed B cell lymphomas", Lancet 346:336-40 (1995).
Press et al., "Prospects for the management of non-Hodgkin's lymphomas with monoclonal antibodies and immunoconjugates", Cancer J. Sci. Am. 4(Suppl 2):S19-26 (1998).
Protheroe et al., "Remission of inflammatory arthropathy in association with anti-CD20 therapy for non-Hodgkin's lymphoma", Rheumatology (Oxford) 38(11):1150-2 (1999).
Qu et al., "Carbohydrates engineered at antibody constant domains can be used for site-specific conjugation of drugs and chelates", J. Immunol. Methods 213(2):131-44 (1998).
Qu et al., "Internalization and cytotoxic effects of a humanized anti-CD74 antibody, LL1", Proc Am Assoc Cancer Res 2002;43:255, Abstract # 1269.
Queen et al., "A humanized antibody that binds to the interleukin 2 receptor", Proc Natl Acad Sci U S A. Dec. 1989;86(24):10029-33.
Renner et al., "Monoclonal antibodies in the treatment of non-Hodgkin's lymphoma: recent results and future prospects", Leukemia 11(Suppl 2):S55-9 (1997).
Riechmann et al., "Reshaping human antibodies for therapy", Nature 332(6162):323-7 (1988).
Roche et al., "Cell surface HLA-DR-invariant chain complexes are targeted to endosomes by rapid internalization", Proc Natl Acad Sci U S A. Sep. 15, 1993;90(18):8581-5.
Rowan et al., "Cross-linking of the CAMPATH-1 antigen (CD52) mediates growth inhibition in human B- and T-lymphoma cell lines, and subsequent emergence of CD52-deficient cells", Immunology 95(3):427-36 (1998).
Rudikoff et al., "Single amino acid substitution altering antigen-binding specificity", Proc. Natl. Acad. Sci. USA 79(6):1979-83 (1982).
Rudnick et al., "Affinity and avidity in antibody-based tumor targeting", Cancer Biother Radiopharm. Apr. 2009;24(2):155-61.
Saltzman et al., "Transport rates of proteins in porous materials with known microgeometry", Biophys. J. 55(1):163-71 (1989).
Sandhu, J. S., "Protein engineering of antibodies", Crit. Rev. Biotechnol. 12(5-6):437-62 (1992).

(56) References Cited

OTHER PUBLICATIONS

Schwarts-Albiez et al., "The carbohydrate moiety of the CD22 antigen can be modulated by inhibitors of the glycosylation pathway", Leukocyte Typing IV. White Cell Differentiation Antigens, Knapp et al., (Eds.), p. 65-67, Oxford University Press, 1989.
Sherwood et al., "Controlled antibody delivery systems", Biotechnology 10(11):1446-9 (1992).
Shih et al., "Internalization and intracellular processing of an anti-B-cell lymphoma monoclonal antibody, LL2", Int J Cancer 56(4):538-45 (1994).
Singer et al., "Optimal humanization of 1B4, an anti-CD18 murine monoclonal antibody, is achieved by correct choice of human V-region framework sequences", J. Immunol. 150(7):2844-57 (1993).
Stein et al., "Epitope specificity of the anti-(B cell lymphoma) monoclonal antibody, LL2", Cancer Immunol. Immunother 37(5):293-8 (1993).
Tallarida, RJ., Drug Synergism and Dose Effect Analysis, Ed. Chapman & Hall, 2000, pp. 1-8; 10-13; 57-71.
Taylor et al., "Human immunoglobulin transgenes undergo rearrangement, somatic mutation and class switching in mice that lack endogenous IgM", Int Immunol. Apr. 1994;6(4):579-91.
Theocharis et al., "Characterization of in vivo mutated T cell clones from patients with systemic lupus erythematosus", Clin. Immunol. Immunopathol. 74(2):135-42 (1995).
Tsang et al.,"Reactive oxygen species mediate doxorubicin induced p53-independent apoptosis", Life Sci. Sep. 5, 2003;73(16):2047-58.
Vuist et al., "Potentiation by interleukin 2 of Burkitt's lymphoma therapy with anti-pan B (anti-CD19) monoclonal antibodies in a mouse xenotransplantation model", Cancer Res. 49(14):3783-8 (1989).
Wilson et al., "cDNA cloning of the B cell membrane protein CD22: a mediator of B—B cell interactions", J Exp Med. Jan. 1, 1991;173(1):137-46.
Wilson et al., "Genomic structure and chromosomal mapping of the human CD22 gene", J Immunol. Jun. 1, 1993;150(11):5013-24.
Wosnik et al., "Rapid construction of large synthetic genes: total chemical synthesis of two different versions of the bovine prochymosin gene", Gene. 1987;60(1):115-27.
Wurflein et al., "Evaluating antibodies for their capacity to induce cell-mediated lysis of malignant B cells", Cancer Res. Jul. 15, 1998;58(14):3051-8.
Anbalagan et al., "Peptidomimetic Src/pretubulin inhibitor KX-01 alone and in combination with paclitaxel suppresses growth, metastasis in human ER/PR/HER2-negative tumor xenografts", Mol Cancer Ther. Sep. 2012;11(9):1936-47.
Bennouna et al., "Therapeutic strategies for colorectal cancer in Europe and the United States: focus on chemotherapy for advanced colorectal cancer" Int. J. Clin. Oncol. (2002) 7:236-244.
Burkard et al., "Validating cancer drug targets through chemical genetics", Biochim Biophys Acta. Dec. 2010;1806(2):251-7.
Burke et al., "Design, synthesis, and biological evaluation of antibody-drug conjugates comprised of potent camptothecin analogues", Bioconjug Chem. Jun. 2009;20(6):1242-50.
Burnham et al., "Invasion of HeLa cells by group B *Streptococcus* requires the phosphoinositide-3-kinase signalling pathway and modulates phosphorylation of host-cell Akt and glycogen synthase kinase-3", Microbiology. Dec. 2007;153(Pt 12):4240-52.
Cao et al., "Bispecific Antibodies as Novel Bioconjugates" Bioconj. Chem. Nov.-Dec. 1998;9(6):635-44.
Cardillo et al., "Humanized anti-Trop-2 IgG-SN-38 conjugate for effective treatment of diverse epithelial cancers: preclinical studies in human cancer xenograft models and monkeys", Clin Cancer Res. May 15, 2011;17(10):3157-69.
Carter et al., Chemotherapy of Cancer; 2nd Edition; John Wiley & Sons, New York, 1981; Appendix C.
Chari et al., "Immunoconjugates Containing Novel Maytansinoids: Promising Anticancer Drugs" Cancer Res. Jan. 1, 1992;52(1):127-31.
Feldmann et al., "Design of effective immunotherapy for human autoimmunity", Nature. Jun. 2, 2005;435(7042):612-9.

Fukuda et al., "Evaluation of novel platinum complexes, inhibitors of topoisomerase I and II in non-small cell lung cancer (NSCLC) sublines resistant to cisplatin", Anticancer Res. Mar.-Apr. 1995;15(2):393-8.
Garcia-Giron et al., "Phase II trial of fortnightly irinotecan (CPT-11) in the treatment of colorectal cancer patients resistant to previous fluoropyrimidine-based chemotherapy", Clin Transl Oncol. Jul. 2005;7(6):244-9.
Gomez-Manzano et al., "Delta-24 increases the expression and activity of topoisomerase I and enhances the antiglioma effect of irinotecan", Clin Cancer Res. Jan. 15, 2006;12(2):556-62.
Govindan et al., "Milatuzumab-SN-38 conjugates for the treatment of CD74+ cancers", Mol Cancer Ther. Jun. 2013;12(6):968-78.
Gueritte-Voegelein et al., "Relationships between the Structure of Taxol Analogues and Their Antimitotic Activity" J. Med. Chem. 1991, 34, 992-998.
Guillemard et al., "Taxane-Antibody Conjugates Afford Potent Cytotoxicity, Enhanced Solubility, and Tumor Target Selectivity" Cancer Res. 61, 694-699, Jan. 15, 2001.
Gura, T., "Systems for identifying new drugs are often faulty", Science. Nov. 7, 1997;278(5340):1041-2.
Hatzakis et al., "Synthesis and single enzyme activity of a clicked lipase-BSA hetero-dimer" Chem. Commun., 2006, 2012-2014.
He et al., "Synthesis and biological evaluation of bis and monocarbonate prodrugs of 10-hydroxycamptothecins", Bioorg Med Chem. Aug. 1, 2004;12(15):4003-8.
Heindel et al., "A Novel Heterobifunctional Linker for Formyl to Thiol Coupling" Bioconjugate Chem. 1991, 2, 427-430.
Horwitz et al., "Antiviral action of camptothecin", Antimicrob Agents Chemother. Nov. 1972;2(5):395-401.
Huang et al., "The Rana catesbeiana rcr Gene Encoding a Cytotoxic Ribonuclease" J. Biol. Chem. 273(11):6395-6401 (1998).
Kaiser, J., "Cancer. First pass at cancer genome reveals complex landscape", Science. Sep. 8, 2006;313(5792):1370.
King et al., "Monoclonal Antibody Conjugates of Doxorubicin Prepared with Branched Linkers: A Novel Method for Increasing the Potency of Doxorubicin Immunoconjugates" Bioconjugate Chem. 1999, 10, 279-288.
Kreitman et al., "Pseudomonas Exotoxin-based Immunotoxins Containing the Antibody LL2 or LL2-Fab' Induce Regression of Subcutaneous Human B-Cell Lymphoma in Mice" Cancer Res. 53, 819-825, Feb. 15, 1993.
Krontiris and Capizzi, Internal Medicine, Chapters 71-72, pp. 699-729; 4th Edition, Jay Stein (Ed.), Elsevier Science, 1994.
Kufe et al., Non-Intercalating Topoisomerase-Targeting Drugs, Holland-Frei Cancer Medicine, Hamilton (ON), BC Decker (2003).
Kufe et al., Topoisomerase Biology, 6th Ed., Holland-Frei Cancer Medicine, Hamilton (ON), BC Decker (2003).
Mahato et al., "Prodrugs for improving tumor targetability and efficiency", Adv Drug Deliv Rev. Jul. 18, 2011;63(8):659-70.
Matsumura, Y., Preclinical and clinical studies of NK012, an SN-38-incorporating polymeric micelles, which is designed based on EPR effect, Adv Drug Deliv Rev. Mar. 18, 2011;63(3):184-92.
Miller et al., "Development of Taxoids with Enhanced Toxicity and Solubility" Poster Presentation, 224th ACS Nat. Meeting, Aug. 18-22, 2002, Boston, MA.
Mine Safety and Health Administration (Special Hazards of Acetylene, Sep. 16, 2011).
Moon et al., "Antibody Conjugates of 7-Ethyl-10-hydroxycamptothecin (SN-38) for Targeted Cancer Chemotherapy" J. Med. Chem. 2008, 51, 6916-6926.
Newton et al., "Potent and specific antitumor effects of an anti-CD22-targeted cytotoxic ribonuclease: potential for the treatment of non-Hodgkin lymphoma" Blood, 97(2):528-35 (2001).
Paul, W., ed., Fundamental Immunology, 3rd Ed., Raven Press, New York, 1993, p. 292-295.
Perez et al., "Inhibition by the anti-mitotic drug doxorubicin of platelet-activating-factor-induced late eosinophil accumulation in rats" Eur. J. Pharmacol. Sep. 4, 1998;356(2-3):239-43.
Reddy et al., "Elimination of Fc Receptor-Dependent Effector Functions of a Modified IgG4 Monoclonal Antibody to Human CD4", J. Immunol. 164:1925-1933 (2000).

(56) References Cited

OTHER PUBLICATIONS

Rowlinson-Busza et al., "Targeted delivery of biologic and other antineoplastic agents" Curr. Opin. Oncol. Dec. 1992;4(6):1142-1148.
Sharkey et al., "Epratuzumab-SN-38: a new antibody-drug conjugate for the therapy of hematologic malignancies", Mol Cancer Ther. Jan. 2012;11(1):224-34.
Sharkey et al., "Combination radioimmunotherapy and chemoimmunotherapy involving different or the same targets improves therapy of human pancreatic carcinoma xenograft models", Mol Cancer Ther. Jun. 2011;10(6):1072-81.
Shih et al., "The Processing and Fate of Antibodies and Their Radiolabels Bound to the Surface of Tumor Cells In Vitro: A Comparison of Nine Radiolabels" J. Nucl. Med. 1994; 35:899-908.
Shih et al., "In vitro and in vivo reactivity of an internalizing antibody, RS7, with human breast cancer", Cancer Res. Dec. 1, 1995;55(23 Suppl):5857s-5863s.
Stanford University Environmental Health and Safety (Information on Azide Compounds, Dec. 2, 2008).
Suzawa et al., "Synthesis of a Novel Duocarmycin Derivative DU-257 and its Application to Immunoconjugate Using Poly(ethylene glycol)-dipeptidyl Linker Capable of Tumor Specific Activation" Bioorg. Med. Chem. 8(8):2175-84 (2000).
Suzawa et al., "Enhanced tumor cell selectivity of adriamycin-monoclonal antibody conjugate via a poly(ethylene glycol)-based cleavable linker" J. Control. Release 79:229-242 (2002).
Trail et al., "Carcinoma Reactive Doxorubicin (DOX) Conjugates: Comparison of BR64-DOX Conjugates Prepared With Disulfide or Thioether Linkers", Proc. Amer. Assoc. Cancer Res., vol. 34, Mar. 1993, #2858, p. 479.
Talmadge et al., "Murine models to evaluate novel and conventional therapeutic strategies for cancer", Am J Pathol. Mar. 2007;170(3):793-804.
Thurber et al., "Antibody tumor penetration: transport opposed by systemic and antigen-mediated clearance", Adv Drug Deliv Rev. Sep. 2008;60(12):1421-34.
Van Noort and Amor, "Cell Biology of Autoimmune Disease", vol. 178, pp. 127-206; International Rev. of Cytology, 1998.
Walker et al., "Synthesis of an Immunoconjugate of Camptothecin" Bioorg. Med. Chem. Lett. 12(2):217-219 (2002).
Ausubel et al., (eds.), Current Protocols in Molecular Biology, pp. 8.2.8-8.2.13, John Wiley & Sons, Inc. (1990).
Ausubel et al., (eds.), Short Protocols in Molecular Biology, pp. 8.8-8.10, John Wiley & Sons, Inc. (1995).
Baines et al., "Purification of Immunoglobulin G (IgG)", Methods in Molecular Biology, vol. 10, pp. 79-104, Manson et al., (eds.), The Human Press (1992).
Bambot et al., "Efficient total gene synthesis of 1.35-kb hybrid alpha-lytic protease gene using the polymerase chain reaction", PCR Methods Appl. Feb. 1993;2(3):266-71.
Baum et al., "Initial clinical results with technetium-99m-labeled LL2 monoclonal antibody fragment in the radioimmunodetection of B-cell lymphomas", Cancer Feb. 1, 1994;73(3 Suppl):896-9.
Beers et al., The Merck Manual of Diagnosis and Therapy, Ch. 180, p. 1474-1476; 17th Ed., Whitehouse Station, NJ, Merck Research Labs (1999).
Belisle et al., "Epitope specificity of the anti-B-cell lymphoma monoclonal antibody, LL2", Proc Am Assoc Cancer Res 1993; 34:481, Abstr #2873.
Bendig, M., "Humanization of Rodent Monoclonal Antibodies by CDR Grafting", Academic Press Inc., New York, NY, vol. 8, (1995), pp. 83-93.
Bhat et al., "Human antilipid A monoclonal antibodies bind to human B cells and the i antigen on cord red blood cells", J Immunol. Nov. 1, 1993;151(9):5011-21.
Carter et al., "Humanization of an anti-p185HER2 antibody for human cancer therapy", Proc. Natl. Acad. Sci. USA 89(10):4285-9 (1992).

Coligan et al., (Eds.), Current Protocols in Immunology, vol. 1, pp. 2.5.1-2.6.7; pp. 2.7.1.-2.7.12; pp. 2.8.1-2.8.10; pp. 2.9.1-2.9.3; pp. 2.10.-2.10.4; John Wiley & Sons, Inc., 1991.
Coloma et al., "Design and production of novel tetravalent bispecific antibodies", Nat. Biotechnol. 15(2):159-63(1997).
Dillon et al., "Use of Polymerase Chain Reaction for the Rapid Construction of Synthetic Genes", Methods in Molecular Biology, vol. 15: PCR Protocols: Current Methods and Applications, White (Ed.), pp. 263-268, Humana Press, Inc. (1993).
Ellis et al., "Engineered anti-CD38 monoclonal antibodies for immunotherapy of multiple myeloma", J Immunol. Jul. 15, 1993;155(2):925-37.
Flavell et al., "Systemic therapy with 3BIT, a triple combination cocktail of anti-CD19, -CD22, and -CD38-saporin immunotoxins, is curative of human B-cell lymphoma in severe combined immunodeficient mice", Cancer Res. 57:4824-9 (1997).
Foy et al., "In vivo CD40-gp39 interactions are essential for thymus-dependent humoral immunity. II. Prolonged suppression of the humoral immune response by an antibody to the ligand for CD40, gp39", J Exp Med. Nov. 1, 1993;178(5):1567-75.
French et al., "Response of B-cell lymphoma to a combination of bispecific antibodies and saporin", Leuk. Res. 20(7):607-17 (1996).
Ghetie et al., "Evaluation of ricin A chain-containing immunotoxins directed against CD19 and CD22 antigens on normal and malignant human B-cells as potential reagents for in vivo therapy", Cancer Res. 48(9):2610-7 (1988).
Goldenberg et al., "Targeting, dosimetry, and radioimmunotherapy of B-cell lymphomas with iodine-131-labeled LL2 monoclonal antibody", J Clin Oncol. Apr. 1991;9(4):548-64.
Goldenberg, D. M., "New Developments in Monoclonal Antibodies for Cancer Detection and Therapy", CA Cancer J. Clin. 44(1):43-64 (1994).
Goldenberg et al., "Epratuzumab (Humanized Anti-CD22 MAb) Conjugated with SN-38, a New Antibody-Drug Conjugate (ADC) for the Treatment of Hematologic Tumors: Preclinical Studies Alone and in Combination with Veltuzumab, a Humanized Anti-CD20 MAb", Blood (ASH Annual Meeting Abstracts) 2010 116: Abstract 3941.
Gondo et al., "HLA class II antigen associated invariant chain gene expression in malignant lymphoma", Br. J. Haematol. 67(4):413-7 (1987).
Green et al., "Antigen-specific human monoclonal antibodies from mice engineered with human lg heavy and light chain YACs", Nature Genetics 7:13-21 (1994).
Gussow et al., "Humanization of monoclonal antibodies", Methods Enzymol. 1991;203:99-121.
Hansen et al., "Internalization and catabolism of radiolabelled antibodies to the MHC class-II invariant chain by B-cell lymphomas", Biochem. J. 1996, 320:293-300.
Hashida et al., "More useful maleimide compounds for the conjugation of Fab' to horseradish peroxidase through thiol groups in the hinge", J Appl Biochem. Feb.-Apr. 1984;6(1-2):56-63.
Hekman et al., "Initial experience with treatment of human B cell lymphoma with anti-CD19 monoclonal antibody", Cancer Immunol. Immunother. 1991;32(6):364-72.
Hess et al., "Specificity of effector T lymphocytes in autologous graft-versus-host disease: role of the major histocompatibility complex class II invariant chain peptide", Blood 89(6):2203-9 (1997).
Hildebrandt et al., "Expression of CD 21, CD 22, and the mouse erythrocyte receptor on peripheral B lymphocytes in rheumatoid arthritis", Ann Rheum Dis. Jul. 1988;47(7):588-94.
Imuran patient information leaflet, GlaxoSmithKline 7076598/5093, Oct. 2004.
Inaoki et al., "CD19-regulated signaling thresholds control peripheral tolerance and autoantibody production in B lymphocytes", J Exp Med. Dec. 1, 1997;186(11):1923-31.
Jones et al., "Replacing the complementarity-determining regions in a human antibody with those from a mouse" Nature 321(6069):522-5 (1986).
Juweid et al., "99Tcm-LL1: a potential new bone marrow imaging agent", Nucl. Med. Commun. 18(2):142-8 (1997).

(56) References Cited

OTHER PUBLICATIONS

Juweid et al., "Treatment of non-Hodgkin's lymphoma with radiolabeled murine, chimeric, or humanized LL2, an anti-CD22 monoclonal antibody", Cancer Res. 55(23 Suppl):5899s-5907s (1995).
Kaminski et al., "Radioimmunotherapy of B-cell lymphoma with [131I]anti-B1 (anti-CD20) antibody", N. Engl. J. Med. 329(7):459-65 (1993).
Kiener et al., "Stimulation of CD40 with purified soluble gp39 induces proinflammatory responses in human monocytes", J Immunol. Nov. 15, 1995;155(10):4917-25.
Kiesel et al., "Removal of cells from a malignant B-cell line from bone marrow with immunomagnetic beads and with complement and immunoglobulin switch variant mediated cytolysis", Leuk. Res. 11(12):1119-25 (1987).
Kohler et al., "Continuous cultures of fused cells secreting antibody of predefined specificity", Nature 256:495-7(1975).
Kreitman et al., "Pseudomonas exotoxin-based immunotoxins containing the antibody LL2 or LL2-Fab' induce regression of subcutaneous human B-cell lymphoma in mice", Cancer Res. 53(4):819-25 (1993).
Leonard et al., "Epratuzumab, a new Anti-CD22, humanized, monoclonal antibody for the therapy of non-Hodgkin's lymphoma (NHL): phase I/II trial results", Blood 94:92a-93a, Abstract # 404, (1999).
Leung et al., "Chimerization and humanization of a B-cell Lymphoma specific antibody, LL2", Proc Am Assoc Cancer Res 1993; 34:481, Abstr #2872.
Leung et al., "Chimerization of LL2, a Rapidly Internalizing Antibody Specific for B Cell Lymphoma", Hybridoma 13(6):469-476 (1994).
Leung et al., "Construction and characterization of a humanized, internalizing, b-cell (CD22)-specific, leukemia/lymphma antibody, LL2", Mol. Immunol. 32(17/18):1413-1427 (1995).
Levine et al., "IgM antibody-related polyneuropathies: B-cell depletion chemotherapy using Rituximab", Neurology 52(8):1701-4 (1999).
Li et al., "The epitope specificity and tissue reactivity of four murine monoclonal anti-CD22 antibodies", Cell Immunol. 118(1):85-99 (1989).
Lonberg et al., "Antigen-specific human antibodies from mice comprising four distinct genetic modifications", Nature 368:856-9 (1994).
Longo, D. L., "Immunotherapy for non-Hodgkin's lymphoma", Curr. Opin. Oncol. 8(5):353-9 (1996).
Losman et al., "Baboon anti-idiotype antibodies mimic a carcinoembryonic antigen epitope", Int J Cancer. Aug. 15, 1990;46(2):310-4.
Lundberg, B., "Preparation of drug-carrier emulsions stabilized with phosphatidylcholine-surfactant mixtures", J. Pharm. Sci. 83(1):72-5 (1994).
Lundberg et al., "Submicron lipid emulsions containing amphipathic polyethylene glycol for use as drug-carriers with prolonged circulation time", Int. J. Pharm. 134:119-127 (1996).
Bardia et al., "Safety and efficacy of anti-Trop-2 antibody drug conjugate, sacituzumab govitecan (IMMU-132), in heavily pre-treated patients with TNBC", Poster presented at San Antonio Breast Cancer Symposium, Dec. 10, 2015, San Antonio, TX.
Bardia et al., "Safety and tumor responses of the anti-Trop-2 antibody drug conjugate, sacituzumab govitecan (IMMU-132), in refractory, metastatic, triple-negative breast cancer (TNBC): An ongoing Phase II trial", Poster presented at AACR-NCI-EORTC International Conference: Molecular Targets and Cancer Therapeutics, Nov. 8, 2015, Boston, MA.
Basu et al., "The epithelial/carcinoma antigen EGP-1, recognized by monoclonal antibody RS7-3G11, is phosphorylated on serine 303", Int J Cancer. Aug. 9, 1995;62(4):472-9.
Basu et al., "Epithelial glycoprotein EGP-1 recognized by MAb RS7-3G11 is phosphorylated on serine 303", Proc. Amer. Assoc. Cancer Res. 36: 439 (Abstr. #2621), 1995.
Camidge et al., "Therapy of Advanced Metastatic Lung Cancers with an Anti-Trop-2-SN-38 Antibody-Drug Conjugate, IMMU-132: Interim Phase II Clinical Results", Oral presentation at 16th World Conference on Lung Cancer (WCLC), Sep. 7, 2015, Denver, CO.
Cardillo et al., "A novel immunotoxin comprising quadruple RNase tethered to an internalizing anti-TROP-2 humanized MAb shows potent cytotoxicity against diverse solid tumors in vitro", Proc. Amer. Assoc. Cancer Res. Annual Meeting, 51:1296 (Abstr. #5346), 2010.
Cardillo et al., "Combining an anti-Trop-2 antibody-SN-38 conjugate (sacituzumab govitecan) with microtubule inhibitors (paclitaxel and eribulin mesylate) or PARP inhibitor (olaparib) significantly improves therapeutic outcome in experimental triple-negative breast cancer (TNBC)", Mol Cancer Ther 2015;14(12 Suppl 2):Abstract nr C166.
Cardillo et al., "Synthetic lethality in TNBC mediated by an anti-Trop-2 antibody-drug conjugate, sacituzumab govitecan (IMMU-132), when combined with paclitaxel or the PARP inhibitor, olaparib", Poster presented at San Antonio Breast Cancer Symposium, Dec. 10, 2015, San Antonio, TX.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31, Epub May 8, 2015.
Chang et al., "In vitro and in vivo evaluation of a novel recombinant immunotoxin of ranpirnase fused to a humanized anti-EGP-1 antobody, HRS7, for the potential treatment of prostate and lung cancers", Proc. Amer. Assoc. Cancer Res. Annual Meeting, 48: (Abstr. #4795), 2007.
Goldenberg et al., Tolerability in mice, monkeys, and rabbits of new antibody (MAb)-drug (SN-38) immunoconjugates. Proc. Amer. Assoc. Cancer Res. 102nd Annual Meeting, 52: 865 (Abstr. #3619), 2011.
Goldenberg et al., "SN-38 antibody-drug conjugates as a novel platform for solid cancer therapy: preclinical science", American Association for Cancer Research (AACR) 2014 Annual Meeting, Abstr. #2904, Apr. 7, 2014.
Goldenberg et al., "Characterization of an anti-Trop-2-SN-38 antibody-drug conjugate (IMMU-132) with potent activity against solid cancers", American Society of Clinical Oncology (ASCO) 50th Annual Meeting. J Clin Oncol 32:5s, 2014 (suppl; abstr #3107), 2014.
Goldenberg et al., "IMMU-132, a potential new antibody-drug conjugate (ADC) for the treatment of triple-negative breast cancer (TNBC): Preclinical and initial clinical results", Poster P5-19-08 presented at San Antonio Breast Cancer Symposium, Dec. 9-13, 2014.
Goldenberg et al., "Trop-2 is a novel target for solid cancer therapy with sacituzumab govitecan (IMMU-132), an antibody-drug conjugate (ADC)", Oncotarget. Jun. 18, 2015. [Epub ahead of print].
Govidan et al., "Optimal cleavable linker for antibody-SN-38 conjugates for cancer therapy: Impact of linker's stability on efficacy", Proc. Amer. Assoc. Cancer Res. 103rd Annual Meeting, 53: 611 (Abstr. #2526), 2012.
Govidan et al., "Preclinical therapy of breast cancer with a radioiodinated humanized anti-EGP-1 monoclonal antibody: advantage of a residualizing iodine radiolabel", Breast Cancer Res Treat Mar. 2004;84(2):173-82.
Govindan et al., "Conjugation of SN-38 to an anti-EGP-1 MAB, HRS7, via a cleavable linker shows selective therapeutic activity in a preclinical model of non-small cell lung cancer (NSCLC)", Proc. Eleventh Conf. on Cancer Therapy, Cancer Biotherapy & Radiopharmaceuticals, 21(4):401 (Abstr. #56), 2006.
Govindan et al., "Therapy of human colonic and lung cancer xenografts with SN-38 conjugates of anti-CEACAM5 and anti-EGP-1 humanized monoclonal antibodies", Proc. AACR Molecular Targets and Cancer Therapeutics, 347-348 (Abstr. #C287), 2007.
Govindan et al., "Efficacious therapies of two human pancreatic cancer xenografts and an aggressive human lymphoma xenograft with redesigned antibody-SN-38 conjugates", Proc. Amer. Assoc. Cancer Res. Annual Meeting, 51:591 (Abstr. #2438), 2010.
Guarino et al., "Therapy of advanced metastatic lung cancer with an anti-Trop-2-SN-38 antibody-drug conjugate (ADC), sacituzumab

(56) References Cited

OTHER PUBLICATIONS govitecan (IMMU-132): Phase I/II clinical experience", J Clin Oncol 33, 2015 (suppl; abstr 2504), Retrieved from http://meetinglibrary.asco.org/content/148373-156.
Liu et al., "Novel immunoRNases comprising multiple copies of ranpimase display potent cytotoxicity in human breast cancer cell lines expressing Trop-2", Proc. Amer. Assoc. Cancer Res. 103rd Annual Meeting, 53: 1124 (Abstr. #4636), 2012.
NCT01270698 (Jan. 3, 2011, pp. 1-4).
NCT01605318 (May 22, 2012, pp. 1-4).
Ocean et al., "Interim results of IMMU-132 (sacituzumab govitecan), an anti-trop-2 antibody-drug conjugate (ADC) in patients with metastatic gastrointestinal (GI) cancers", Poster presented at ESMO's 17th World Congress on Gastrointestinal Cancer, Jul. 4, 2015.
Picozzi et al., "IMMU-132, a new antibody-drug conjugate (ADC), evaluated in patients with advanced, metastatic, pancreatic ductal adenocarcinoma (mPC): Results of a Phase I/II trial", Poster presented at American Association for Cancer Research (AACR) Special Conference on Pancreatic Cancer:Innovations in Research and Treatment, Abstr. #B99, May 18-21, 2014.
Sharkey et al., "Enhanced Delivery of SN-38 to Human Tumor Xenografts with an Anti-Trop-2-SN-38 Antibody Conjugate (Sacituzumab Govitecan)", Clin Cancer Res. Jun. 23, 2015. pii: clincanres.0670.2015. [Epub ahead of print].
Shih et al., "Radioimmunodetection and radioimmunotherapy of xenografted human breast cancer with monoclonal antibody RS7", J. Immunother. 16: 169 (Abstr. #85), 1994.
Starodub et al., "Advanced solid cancer therapy with a novel antibody-drug conjugate (ADC), sacituzumab govitecan (IMMU-132): key preclinical and clinical results", Abstract CT236. Presented at American Association for Cancer Research (AACR) 2015 Annual Meeting, Philadelphia, PA, Apr. 20, 2015.
Starodub et al., "Safety, efficacy, and pharmacokinetics of a new humanized anti-Trop-2 antibody-SN-38 conjugate (IMMU-132) for the treatment of diverse epithelial cancers: Phase I clinical experience", AACR-NCI-EORTC International Conference on Molecular Targets and Cancer Therapeutics Meeting. (Abstr. #C67), Oct. 22, 2013.
Starodub et al., "SN-38 antibody-drug conjugate (ADC) targeting Trop-2, IMMU-132, as a novel platform for the therapy of diverse metastatic solid cancers: Initial clinical results", American Association for Cancer Research (AACR) 2014 Annual Meeting, Abstr. #CT206, Apr. 7, 2014.
Starodub et al., "Therapy of gastrointestinal malignancies with an anti-Trop-2-SN-38 antibody drug conjugate (ADC) (sacituzumab govitecan): Phase I/II clinical experience", 2015 American Society of Clinical Oncology (ASCO) Annual Meeting, J Clin Oncol 33, 2015 (suppl; abstr 3546), Board 38, Jun. 1, 2015.
Starodub et al., "First-in-Human Trial of a Novel Anti-Trop-2 Antibody-SN-38 Conjugate, Sacituzumab Govitecan, for the Treatment of Diverse Metastatic Solid Tumors", Clin Cancer Res. May 5, 2015. [Epub ahead of print].
Starodub et al., "Phase I/II trial of IMMU-132 (isactuzumab govitecan), an anti-Trop-2-SN-38 antibody drug conjugate (ADC): Results in patients with metastatic gastrointestinal (GI) cancers", J Clin Oncol 33, 2015 (suppl 3; abstr 703), Retrieved from http://meetinglibrary.asco.org/content/140198-158.
Stein et al., "Therapy of a breast cancer xenograft using humanized RS7 labeled with residualizing iodine", Proc. Amer. Assoc. Cancer Res. 43: 88 (Abstr. #413), 2002.
Stein et al., "Radioimmunotherapy of lung cancer with MAb RS7-3G11", Proc. Amer. Assoc. Cancer Res. 33: 318 (Abstr. #1897), 1992.
Stein et al., "Radioimmunotherapy with MAb RS7-3G11 in an animal model", Antib. Immunoconj. Radiopharm. 5: 358 (Abstr. #100), 1992.
Stein et al., "Specificity and properties of MAb RS7-3G11 and the antigen defined by this pancarcinoma monoclonal antibody", Int J Cancer. Dec. 2, 1993;55(6):938-46.
Stein et al., "Comparative biodistribution and radioimmunotherapy of monoclonal antibody RS7 and its F(ab')2 in nude mice bearing human tumor xenografts", Cancer. Feb. 1, 1994;73(3 Suppl):816-23.
Stein et al., "Murine monoclonal antibodies raised against human non-small cell carcinoma of the lung: specificity and tumor targeting", Cancer Res. Feb. 15, 1990;50(4):1330-6.
Stein et al., "Effects of radiolabeling monoclonal antibodies with a residualizing iodine radiolabel on the accretion of radioisotope in tumors", Cancer Res. Jul. 15, 1995;55(14):3132-9.
Stein et al., "Successful therapy of a human lung cancer xenograft using MAb RS7 labeled with residualizing radioiodine", Rev Oncol Hematol. Jul.-Aug. 2001;39(1-2):173-80.
Stein et al., "Assessment of combined radioimmunotherapy and chemotherapy for treatment of medullary thyroid cancer", Clin Cancer Res. 5(10 Suppl):3199s-206s, 1999.
Stein et al., Characterization of the epithelial/carcinoma antigen recognized by MAb RS7. Proc. Amer. Assoc. Cancer Res. 35: 501 (Abstr. #2986), 1994.
Stein et al., A novel tumor-associated antigen defined by MAb RS7-3G11: Characterization and internalization properties. Proc. Amer. Assoc. Cancer Res. 33: 341, 1992.
Stein et al., "Characterization of cluster 13: the epithelial/carcinoma antigen recognized by MAb RS7", Int J Cancer Suppl. 1994;8:98-102.
Stein et al., "Targeting and therapy of human non small cell carcinoma of the lung xenografts using 131 I labeled monoclonal antibody RS7 3G11", Proc. Amer. Assoc. Cancer Res. 32: 260, 1991.
Van Rij et al., "Imaging of prostate cancer with immuno-PET and immuno-SPECT using a radiolabeled anti-EGP-1 monoclonal antibody", J Nucl Med. 52(10):1601-7, 2011.
Van Rij et al., "Pretargeting of prostate cancer with an internalizing anti-EGP-1 × anti-HSG bispecific antibody", Annual Congress of the European Association of Nuclear Medicine, Birmingham, UK, Eur J Nucl Med Mol Imaging 38 (Suppl 2):S212 (Abstr. #OP582), 2011.
Vanama et al., Construction, characterization, and mammalian expression of an immunotoxin consisting of ranpirnase (Rap) fused to a humanized anti-EGP-1 antibody, hRS7, as a potential therapeutic for prostate cancer. Proc. Amer. Assoc. Cancer Res., 96th Annual Meeting, 160 (Abstr. #679), 2005.
Bardia et al., "IMMU-132, a new antibody-drug conjugate (ADC) against Trop-2, as a novel therapeutic for patients with relapsed/refractory, metastatic, triple-negative breast cancer (TNBC): Results from Phase I/II clinical trial (NCT01631552)", Poster, San Antonio Breast Cancer Symposium, Dec. 9-13, 2014.
Bardia et al., "Therapy of refractory/relapsed metastatic triple-negative breast cancer (TNBC) with an anti-Trop-2-SN-38 antibody-drug conjugate (ADC), sacituzumab govitecan (IMMU-132): Phase I/II clinical experience", J Clin Oncol 33, 2015 (suppl; abstr 1016), Retrieved from http://meetinglibrary.asco.org/content/150673-156.
Dang et al., "Hypoxia-inducible factor-1 target genes as indicators of tumor vessel response to vascular endothelial growth factor inhibition", Cancer Res. Mar. 15, 2008;68(6):1872-80.
Declaration under 37 C.F.R. 1.132 by David M. Goldenberg, filed in U.S. Appl. No. 13/948,732, filed Jun. 20, 2014.
Declaration under 37 C.F.R. 1.132 by David M. Goldenberg, filed in U.S. Appl. No. 14/204,698, filed Jan. 7, 2015.
Dotan et al., "A new anti-CEA-SN-38 antibody-drug conjugate (ADC), IMMU-130, is active in controlling metastatic colorectal cancer (mCRC) in patients (pts) refractory or relapsing after irinotecan-containing chemotherapies: Initial results of a phase I/II study", J Clin Oncol 33, 2015 (suppl; abstr 2505), Retrieved from http://meetinglibrary.asco.org/content/148390-156.
Faltas et al., "Sacituzumab Govitecan, a Novel Antibody-Drug Conjugate, in Patients With Metastatic Platinum-Resistant Urothelial Carcinoma", Clin Genitourin Cancer. Feb. 2016;14(1):e75-9.
Goldenberg et al., "Selective in vivo therapeutic efficacies of SN-38 conjugates of an anti-CEACAM5 antibody in preclinical models of human colon carcinoma", Presentation, ASCO 2009 Gastrointestinal Cancers Symposium, San Francisco, CA, Jan. 15-17, 2009.

(56) References Cited

OTHER PUBLICATIONS

Goldenberg, D.M., "Challenging the Dogmas: Clinical Efficacy of SN-38-Conjugated Antibodies in Solid Tumors", 26th EORTC-NCI-AACR Symposium on Molecular Targets and Cancer Therapeutics, Barcelona, Spain, Nov. 18-21, 2014.
Goldenberg, D.M., "SN-38 Conjugates for Therapy of Advanced Solid Cancers", 5th Annual World ADC Summit in San Diego, CA, Oct. 26-29, 2014.
Goldenberg et al., "Therapy of human solid tumor xenografts with CD74-targeted milatuzumab-SN-38 immunoconjugates", Poster, 2012 ASCO Annual Meeting, Chicago, IL, Jun. 1-5, 2012.
Goldenberg et al., "Improved Therapeutic Index of IMMU-132 ADC vs. Irinotecan in Preclinical Studies", Presentation, AACR Annual Meeting, San Diego, CA, Apr. 5-9, 2014.
Goldenberg et al., "Tolerability in mice, monkeys, and rabbits of new antibody (MAb)-drug (SN-38) immunoconjugates", Proceedings of the 102nd Annual Meeting of the American Association for Cancer Research; Apr. 2-6, 2011; Orlando, FL. Cancer Res 2011;71(8 Suppl):Abstract # 3619.
Gorman, G., "Focused on Therapy: Cancer, Autoimmune & Other Serious Diseases", Presentation, Oppenheimer 23rd Annual Healthcare Conference, NYC, Dec. 12, 2012.
Govindan et al., "Targeted therapy of human colonic, lung, and pancreatic cancer xenografts, growing in nude mice, with potent antibody conjugates of SN-38", Poster, AACR 100th Annual Meeting, Denver, CO, Apr. 18-22, 2009.
Govindan et al., "Efficacious therapies of two human pancreatic cancer xenografts and an aggressive human lymphoma xenograft with redesigned antibody-SN-38 conjugates", Poster, AACR 101st Annual Meeting, Washington, DC, Apr. 17-21, 2010.
Govindan et al., "Improving the Therapeutic Index in Cancer Therapy by Using Antibody-Drug Conjugates Designed with a Moderately Cytotoxic Drug", Mol Pharm. Nov. 25, 2014. [Epub ahead of print].
Govindan et al., "Optimal cleavable linker for antibody-SN-38 conjugates for cancer therapy: Impact of linker's stability on efficacy", Poster, AACR 103rd Annual Meeting, Chicago, IL, Mar. 31-Apr. 4, 2012.
Govindan et al., "CEACAM5-targeted therapy of human colonic and pancreatic cancer xenografts with potent labetuzumab-SN-38 immunoconjugates", Clin Cancer Res. Oct. 1, 2009;15(19):6052-61.
Govindan et al., "IMMU-130, a unique antibody-drug conjugate (ADC) of SN-38 targeting CEACAM5 antigen: Preclinical basis for clinical activity in metastatic colorectal cancer (mCRC)", J Clin Oncol 33, 2015 (suppl 3; abstr 625), Retrieved from http://meetinglibrary.asco.org/content/139777-158.
Karacay et al., "Combining antibody-targeted radiation (radioimmunotherapy) and antibody-SN-38 conjugates (ADC) improves pancreatic cancer therapy", Poster, AACR 101st Annual Meeting, Washington, DC, Apr. 17-21, 2010.
Moon et al., "Cross-linker evaluation in the design of antibody-SN-38 conjugates for cancer therapy", Poster, AACR 101st Annual Meeting, Washington, DC, Apr. 17-21, 2010.
Reagan-Shaw et al., "Dose translation from animal to human studies revisited", FASEB J. Mar. 2008;22(3):659-61.
Segal et al., "IMMU-130, an SN-38 antibody-drug conjugate (ADC) targeting CEACAM5, is therapeutically active in metastatic colorectal cancer (mCRC): Initial clinical results of two Phase I studies", Presentation, AACR Annual Meeting, San Diego, CA, Apr. 5-9, 2014.
Segal et al., "IMMU-130, an SN-38 antibody-drug conjugate (ADC) targeting CEACAM5, is therapeutically active in metastatic colorectal cancer (mCRC): Initial clinical results of two Phase I studies", 2014 AACR Meeting Apr. 5-9, 2-14, San Diego, CA (Abstract No. CT211).
Seruga et al., "Failures in Phase III: Causes and Consequences", Clin Cancer Res. Oct. 15, 2015;21(20):4552-60.
Starodub et al., "IMMU-132, an SN-38 antibody-drug conjugate (ADC) targeting Trop-2, as a novel platform for the therapy of diverse metastatic solid cancers: Clinical results", Poster, the 2014 Annual Meeting of the American Society of Clinical Oncology (ASCO), May 30-Jun. 3, 2014.
Tahara et al., "The Use of Olaparib (AZD2281) Potentiates SN-38 Cytotoxicity in Colon Cancer Cells by Indirect Inhibition of Rad51-Mediated Repair of DNA Double-Strand Breaks", Mol Cancer Ther; 13(5); 1170-80 (2014).
Bambury et al., "The safety and efficacy of single-agent pemetrexed in platinum-resistant advanced urothelial carcinoma: a large single-institution experience", Oncologist. May 2015;20(5):508-15.
Bardia et al., "Efficacy and Safety of Anti-Trop-2 Antibody Drug Conjugate Sacituzumab Govitecan (IMMU-132) in Heavily Pre-treated Patients With Metastatic Triple-Negative Breast Cancer", J Clin Oncol. Jul. 1, 2017;35(19):2141-2148.
Beer et al., "Southwest Oncology Group phase II study of irinotecan in patients with advanced transitional cell carcinoma of the urothelium that progressed after platinum-based chemotherapy", Clin Genitourin Cancer. Mar. 2008;6(1):36-9.
Bellmunt et al., "Phase III trial of vinflunine plus best supportive care compared with best supportive care alone after a platinum-containing regimen in patients with advanced transitional cell carcinoma of the urothelial tract", J Clin Oncol. Sep. 20, 2009;27(27):4454-61.
Birchard et al., "Early changes in tumor size in patients treated for advanced stage nonsmall cell lung cancer do not correlate with survival", Cancer. Feb. 1, 2009;115(3):581-6.
Chaudhary et al., "A phase II study of gemcitabine and irinotecan in patients with locally advanced or metastatic bladder cancer", Am J Clin Oncol. Apr. 2014;37(2):188-93.
Clininal Trial NCT01631552 (Jun. 28, 2012, pp. 1-5).
Da Roit et al., "Ibrutinib interferes with the cell-mediated anti-tumor activities of therapeutic CD20 antibodies: implications for combination therapy", Haematologica. Jan. 2015; 100(1): 77-86.
Furuse et al., "Phase II study of vinorelbine in heavily previously treated small cell lung cancer. Japan Lung Cancer Vinorelbine Study Group", Oncology. Mar.-Apr. 1996;53(2):169-72.
Galsky et al., "Phase II trial of pemetrexed as second-line therapy in patients with metastatic urothelial carcinoma", Invest New Drugs. Jun. 2007;25(3):265-70.
Gray et al., "Therapy of Small Cell Lung Cancer (SCLC) with a Topoisomerase-1-inhibiting Antibody-Drug Conjugate (ADC) Targeting Trop-2, Sacituzumab Govitecan", Clin Cancer Res. Oct. 1, 2017;23(19):5711-5719.
Hagmann et al., "Second-Line Therapy of Small-Cell Lung Cancer: Topotecan Compared to a Combination Treatment with Adriamycin, Cyclophosphamide and Vincristine (ACO)—a Single Center Experience", J Cancer. Sep. 15, 2015;6(11):1148-54.
Heist et al., "Therapy of Advanced Non-Small-Cell Lung Cancer With an SN-38-Anti-Trop-2 Drug Conjugate, Sacituzumab Govitecan", J Clin Oncol. Aug. 20, 2017;35(24):2790-2797.
Horita et al., "Topotecan for Relapsed Small-cell Lung Cancer: Systematic Review and Meta-Analysis of 1347 Patients", Sci Rep. Oct. 21, 2015;5:15437.
Inoeu et al., "Randomized phase II trial comparing amrubicin with topotecan in patients with previously treated small-cell lung cancer: North Japan Lung Cancer Study Group Trial 0402", J Clin Oncol. Nov. 20, 2008;26(33):5401-6.
Jalal et al., "Pemetrexed in second line and beyond small cell lung cancer: a Hoosier Oncology Group phase II study", J Thorac Oncol. Jan. 2009;4(1):93-6.
Jotte et al., "Randomized phase II trial of single-agent amrubicin or topotecan as second-line treatment in patients with small-cell lung cancer sensitive to first-line platinum-based chemotherapy", J Clin Oncol. Jan. 20, 2011;29(3):287-93.
Liu et al., "A randomized phase 2 study of combination cediranib and olaparib versus olaparib alone as recurrence therapy in platinum-sensitive ovarian cancer", Lancet Oncol. Oct. 2014; 15(11): 1207-1214.
Loehrer et al., "A randomized comparison of cisplatin alone or in combination with methotrexate, vinblastine, and doxorubicin in patients with metastatic urothelial carcinoma: a cooperative group study", J Clin Oncol. Jul. 1992;10(7):1066-73.

(56) References Cited

OTHER PUBLICATIONS

Logothetis et al., "A prospective randomized trial comparing MVAC and CISCA chemotherapy for patients with metastatic urothelial tumors", J Clin Oncol. Jun. 1990;8(6):1050-5.
Ocean et al., "Sacituzumab govitecan (IMMU-132), an anti-Trop-2-SN-38 antibody-drug conjugate for the treatment of diverse epithelial cancers: Safety and pharmacokinetics", Cancer. Oct. 1, 2017;123(19):3843-3854.
Pallis et al., "A multicenter randomized phase II study of the irinotecan/gemcitabine doublet versus irinotecan monotherapy in previously treated patients with extensive stage small-cell lung cancer", Lung Cancer. Aug. 2009;65(2):187-91.
Petrylak et al., "Randomized phase II study of docetaxel with or without ramucirumab (IMC-1121B) or icrucumab (IMC-18F1) in patients with urothelial transitional cell carcinoma (TCC) following progression on first-line platinum-based therapy", J Clin Oncol. 2012;30 (abstract TPS4675).
Sandler, AB., "Irinotecan in small-cell lung cancer: the US experience", Oncology (Williston Park). Jan. 2001;15(1 Suppl 1):11-2.
Smit et al., "A phase II study of paclitaxel in heavily pretreated patients with small-cell lung cancer", Br J Cancer. 1998; 77(2): 347-351.
Sonpavde et al., "Improved prognostic classification of patients receiving salvage systemic therapy for advanced urothelial carcinoma", J Clin Oncol. 2015; 33(7):311.
Stepan et al., "Expression of Trop2 cell surface glycoprotein in normal and tumor tissues: potential implications as a cancer therapeutic target", J Histochem Cytochem. Jul. 2011;59(7):701-10.
Sweeney et al., "Phase II study of pemetrexed for second-line treatment of transitional cell cancer of the urothelium", J Clin Oncol. Jul. 20, 2006;24(21):3451-7.
Tagawa et al., "Sacituzumab govitecan (IMMU-132) for patients with pretreated metastatic urothelial uancer (UC): interim results", Annals of Oncology (2017) 28 (suppl_5): v295-v329.
The FDA Guidance of clinical trial protocol for dosage determination (Feb. 1999, pp. 1-31).
Van Der Lee et al., "Single-agent gemcitabine in patients with resistant small-cell lung cancer", Ann Oncol. Apr. 2001;12(4):557-61.
Von Der Maase et al., "Long-term survival results of a randomized trial comparing gemcitabine plus cisplatin, with methotrexate, vinblastine, doxorubicin, plus cisplatin in patients with bladder cancer", J Clin Oncol. Jul. 20, 2005;23(21):4602-8.
Von Pawel, J., "The role of topotecan in treating small cell lung cancer: second-line treatment", Lung Cancer. Aug. 2003;41 Suppl 4:S3-8.
ADC Could Benefit Some with Breast Cancer, Cancer Discov. May 2019;9(5):570.
An ADC for Triple-Negative Breast Cancer, Cancer Discov. Jan. 2016;6(1):OF8.
Bardia et al., "Sacituzumab Govitecan-hziy in Triple-Negative Breast Cancer. Reply", N Engl J Med. Jun. 13, 2019;380(24):2382.
Bardia et al., "Sacituzumab Govitecan-hziy in Refractory Metastatic Triple-Negative Breast Cancer", N Engl J Med. Feb. 21, 2019;380(8):741-751.
Burk, TK, "Sacituzumab govitecan activity in advanced breast cancer", Lancet Oncol. May 2017;18(5):e246.
Cardillo et al., "IMMU-140, a Novel SN-38 Antibody-Drug Conjugate Targeting HLA-DR, Mediates Dual Cytotoxic Effects in Hematologic Cancers and Malignant Melanoma", Mol Cancer Ther. Jan. 2018;17(1):150-160.
Cardillo et al., "Synthetic Lethality Exploitation by an Anti-Trop-2-SN-38 Antibody-Drug Conjugate, IMMU-132, Plus PARP Inhibitors in BRCA1/2-wild-type Triple-Negative Breast Cancer", Clin Cancer Res. Jul. 1, 2017;23(13):3405-3415.
Cardillo et al., "Sacituzumab Govitecan (IMMU-132), an Anti-Trop-2/SN-38 Antibody-Drug Conjugate: Characterization and Efficacy in Pancreatic, Gastric, and Other Cancers", Bioconjug Chem. May 20, 2015;26(5):919-31.
Chang et al., "Combining ABCG2 Inhibitors with IMMU-132, an Anti-Trop-2 Antibody Conjugate of SN-38, Overcomes Resistance to SN-38 in Breast and Gastric Cancers", Mol Cancer Ther. Aug. 2016;15(8):1910-9.
Dong et al., "Antibody-drug conjugates of 7-ethyl-10-hydroxycamptothecin: Sacituzumab govitecan and labetuzumab govitecan", Eur J Med Chem. Apr. 1, 2019;167:583-593.
Dotan et al., "Phase I/II Trial of Labetuzumab Govitecan (Anti-CEACAM5/SN-38 Antibody-Drug Conjugate) in Patients With Refractory or Relapsing Metastatic Colorectal Cancer", J Clin Oncol. Oct. 10, 2017;35(29):3338-3346.
Goldenberg et al., "The emergence of trophoblast cell-surface antigen 2 (TROP-2) as a novel cancer target", Oncotarget. Jun. 22, 2018;9(48):28989-29006.
Goldenberg et al., "Antibody-drug conjugates targeting TROP-2 and incorporating SN-38: A case study of anti-TROP-2 sacituzumab govitecan", MAbs. Jul. 18, 2019:1-9.
Han et al., "Sacituzumab Govitecan (IMMU-132) in treatment-resistant uterine serous carcinoma: A case report", Gynecol Oncol Rep. May 23, 2018;25:37-40.
Kaplon et al., "Antibodies to watch in 2019", MAbs. Feb.-Mar. 2019;11(2):219-238.
Kaplon et al., "Antibodies to watch in 2018", MAbs. Feb.-Mar. 2018;10(2):183-203.
Lu et al., "Advances in antibody therapeutics targeting small-cell lung cancer", Adv Clin Exp Med. Sep. 2018;27(9):1317-1323.
Nagayama et al., "Antibody-Drug Conjugates for the Treatment of Solid Tumors: Clinical Experience and Latest Developments", Target Oncol. Dec. 2017;12(6):719-739.
Ozaki et al., "Sacituzumab Govitecan-hziy in Triple-Negative Breast Cancer", N Engl J Med. Jun. 13, 2019;380(24):2382.
Ponde et al., "Antibody-Drug Conjugates in Breast Cancer: a Comprehensive Review", Curr Treat Options Oncol. Apr. 1, 2019;20(5):37.
Sahota et al., "Sacituzumab govitecan: an antibody-drug conjugate", Expert Opin Biol Ther. Aug. 2017;17(8):1027-1031.
Sharkey et al., Selective and Concentrated Accretion of SN-38 with a CEACAM5-Targeting Antibody-Drug conjugate (ADC), Labetuzumab Govitecan (IMMU-130), Mol Cancer Ther. Jan. 2018;17(1):196-203.
Shvartsur et al., "Trop2 and its overexpression in cancers: regulation and clinical/therapeutic implications", Genes Cancer. Mar. 2015;6(3-4):84-105.
Stirrups, R., "Sacituzumab govitecan-hziy for triple-negative breast cancer", Lancet Oncol. Apr. 2019;20(4):e194.
Tray et al., "Antibody-drug conjugates in triple negative breast cancer", Future Oncol. Oct. 2018;14(25):2651-2661.
Vlachostergios et al., "Antibody-Drug Conjugates in Bladder Cancer", Bladder Cancer. Jul. 30, 2018;4(3):247-259.
Vranic et al., "Potential Novel Therapy Targets in Neuroendocrine Carcinomas of the Breast", Clin Breast Cancer. Apr. 2019;19(2):131-136.
Zangardi et al., "Sacituzumab for the treatment of triple-negative breast cancer: the poster child of future therapy?", Expert Opin Investig Drugs. Feb. 2019;28(2):107-112.

\* cited by examiner

| Agent | SN-38/IgG Substitution Ratio | Free SN-38 (%) | Human Serum Half-Life (h) | Cell Binding: Kd (nM) (95% C.I.) | Cytotoxicity: IC$_{50}$ (nM) (95% C.I.) |
|---|---|---|---|---|---|
| hRS7-CL2-SN-38 | 6.2 | 0.7 | 22.1 | 1.19 (0.89 to 149) | 4.12 (2.88 to 5.89) |
| hRS7-CL2A-SN-38 | 6.1 | 0.6 | 20.3 | 1.09 (0.97 to 1.21) | 4.24 (2.99 to 6.01) |

```
                          SEQUENCE LISTING

<160> NUMBER OF SEQ ID NOS: 9

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Ser Gln Asp Val Ser Ile Ala Val Ala
1               5                   10

<210> SEQ ID NO 2
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Ala Ser Tyr Arg Tyr Thr
1               5

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gln Gln His Tyr Ile Thr Pro Leu Thr
1               5

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Tyr Gly Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Trp Ile Asn Thr Tyr Thr Gly Glu Pro Thr Tyr Thr Asp Asp Phe Lys
```

-continued

```
1               5                   10                  15
Gly

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Gly Gly Phe Gly Ser Ser Tyr Trp Tyr Phe Asp Val
1               5                   10

<210> SEQ ID NO 7
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Ala Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270
```

Asn Tyr Lys Thr Thr Pro Val Leu Asp Ser Asp Gly Ser Phe Phe
            275                 280                 285

Leu Tyr Ser Lys Leu Thr Val Asp Lys Ser Arg Trp Gln Gln Gly Asn
        290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 8
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Val Leu Asp Ser Asp Gly Ser Phe Phe
        275                 280                 285

```
Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Ala Leu Ala Leu
1
```

US 10,744,129 B2

THERAPY OF SMALL-CELL LUNG CANCER (SCLC) WITH A TOPOISOMERASE-I INHIBITING ANTIBODY-DRUG CONJUGATE (ADC) TARGETING TROP-2

RELATED APPLICATIONS

This application is a continuation-in-part of U.S. patent application Ser. No. 15/820,708, filed Nov. 22, 2017, which was a continuation-in-part of U.S. patent application Ser. No. 15/069,208, filed Mar. 14, 2016, which was a continuation-in-part of U.S. patent application Ser. No. 14/667,982 (now issued U.S. Pat. No. 9,493,573), filed Mar. 25, 2015, which was a divisional of U.S. application Ser. No. 13/948,732 (now U.S. Pat. No. 9,028,833), filed Jul. 23, 2013, which claimed the benefit under 35 U.S.C. 119(e) of U.S. Provisional Patent Applications 61/736,684, filed Dec. 13, 2012, and 61/749,548, filed Jan. 7, 2013. Application Ser. No. 15/069,208 claimed the benefit under 35 U.S.C. 119(e) of U.S. Provisional Patent Applications 62/133,654, filed Mar. 16, 2015, 62/133,729, filed Mar. 16, 2015, 62/138,092, filed Mar. 25, 2015, 62/156,608, filed May 4, 2015, and 62/241,881, filed Oct. 15, 2015. Application Ser. No. 15/069,208 claimed the benefit under 35 U.S.C. 119(e) of U.S. Provisional Patent Application 62/428,655, filed Dec. 1, 2016. The present application claims the benefit under 35 U.S.C. 119(e) of U.S. Provisional Patent Application 62/463,316, filed Feb. 24, 2017. The text of each priority application is incorporated herein by reference in its entirety.

GOVERNMENT SUPPORT

This invention was made with government support under Grant Number CA171388 awarded by the National Institutes of Health. The government has certain rights in the invention.

SEQUENCE LISTING

The instant application contains a Sequence Listing which has been submitted in ASCII format via EFS-Web and is hereby incorporated by reference in its entirety. Said ASCII copy, created on Feb. 14, 2018, is named IMM370US1_SL.txt and is 8,305 bytes in size.

FIELD OF THE INVENTION

This invention relates to compositions and methods of use of anti-Trop-2 antibody-drug conjugates (ADCs), for treating small cell lung cancer (SCLC). Preferably, the ADC is an anti-Trop-2-SN-38 conjugate, such as sacituzumab govitecan. More preferably, a linker such as CL2A may be used to attach the drug to the antibody or antibody fragment. However, other linkers, other known cytotoxic drugs, and other known methods of conjugating drugs to antibodies may be utilized. Most preferably, the antibody or antigen-binding fragment thereof is a humanized RS7 antibody. The antibody or fragment may be attached to 1-12, 1-6, 1-5, 6-8 or 7-8 copies of drug moiety or drug-linker moiety per antibody or fragment. The ADCs are of use for therapy of SCLC patients who are either chemosensitive to or chemoresistant to first-line platinum-containing chemotherapy. In certain embodiments, the ADCs may be of use for first-line therapy of SCLC. Surprisingly, the ADCs are of use in SCLC patients who either relapsed from or fail to respond to topotecan therapy, despite it also being an inhibitor of topoisomerase I. The ADCs are similarly active in second line vs. later stages of metastatic SCLC (mSCLC). The ADCs may be used alone or as a combination therapy, along with one or more therapeutic modalities selected from the group consisting of surgery, radiation therapy, chemotherapy, immunomodulators, cytokines, chemotherapeutic agents, pro-apoptotic agents, anti-angiogenic agents, cytotoxic agents, drugs, toxins, radionuclides, RNAi, siRNA, a second antibody or antibody fragment, and an immunoconjugate. In preferred embodiments, the combination of ADC and other therapeutic modality exhibits a synergistic effect and is more effective to induce cancer cell death than either ADC or other therapeutic modality alone, or the sum of the effects of ADC and other therapeutic modality administered individually. Surprisingly, subcutaneous administration of the anti-Trop-2 ADC does not result in unacceptable localized toxicity at the site of administration and in alternative embodiments the ADC may be administered intravenously or subcutaneously.

RELATED ART

Small-cell lung cancer (SCLC), originating from neuroendocrine progenitor cells, comprises approximately 15% of all lung cancers, yet has one of the lowest 5-year survival rates at 6% (Alvarado-Luna et al., 2016, Transl Lung Cancer Res 5:26-38; Siegel et al., 2017, CA Cancer J Clin 67:7-30). This is because it is highly aggressive, with about two-thirds of patients having metastatic disease at diagnosis (Fruh et al., 2013, Ann Oncol 24(6):vi99-105). Whereas first-line therapy of stage IV SCLC is palliative yet has a high initial response rate of 60-75%, the outcome usually is poor, with a median progression-free survival (PFS) of only 5.5 months and a median overall survival (OS) of <10 months (Foster et al., 2011, Cancer 117:1262-71; Wolfson et al., 2011, Int J Radiat Oncol Biol Phys 81:77-84) with platinum-based chemotherapy (Fruh et al., 2013, Ann Oncol 24(6):vi99-105).

Responses to second-line therapy have been poorer, such as <10%, and with a median survival of only 4 or 5 months after second- or third-line chemotherapy (Hurwitz et al., 2009, Oncologist 14:986-94; Schneider, 2008, J Natl Compr Canc Netw 6:323-31), especially when there is resistance to first-line treatment (i.e., response duration <3 months). The only approved drug in this setting, since 1998, is topotecan, indicated for recurrent patients who were sensitive (duration of response exceeding 3 months) to a platinum-based therapy (O'Brien et al., 2006, J Clin Oncol 24:5441-7; Perez-Soler et al., 1996, J Clin Oncol 14:2785-90). However, irinotecan, taxanes, vinorelbine, and gemcitabine also are given frequently to patients with chemosensitive recurrent disease (Furuse et al., 1996, Oncology 53:169-72; Smit et al., 1998, Br J Cancer 77:347-51; Sandler, 2001, Oncology (Williston Park) 15:11-2; van der Lee et al., 2001, Ann Oncol 12:557-61).

A review of recent randomized phase II and III clinical trials including topotecan in a control arm showed 13 to 17% responses in second line (Inoue et al., 2008, J Clin Oncol 26:5401-6; Jotte et al., 2011, J Clin Oncol 29:287-93; Horita et al., 2015, Sci Rep 5:15437), but with as much as a 20% response rate among patients with chemosensitive disease, and only 4% for those who were chemoresistant (von Pawel, 2003, Lung Cancer 41 (Suppl 4):S3-8). However, these responses and/or disease stabilization in second line do not translate into improved survival. For example, Hagmann and colleagues (Hagmann et al., 2015, J Cancer 6:1148-5418) reported a 22.5% response with topotecan, and a median PFS of 2.4 months and a median OS of 5 months. In a third-line setting, no objective responses were achieved, while a median PFS of 1.3 months and a median OS of 2.5 months was reported (Hagmann et al., 2015, J Cancer 6:1148-5418). Other established single-agent chemotherapies or retreatment with platinum plus etoposide combinations also have been disappointing, yielding similar survival outcomes as topotecan alone (Hagmann et al., 2015, J Cancer 6:1148-5418). Irinotecan has shown very low or no responses and a median time to progression (TTP) of 1.7 months, while a median OS of 4.6 months also has been reported (Pallis et al., 2009, Lung Cancer 65:187-91). Gemcitabine has not given any objective response, and resulted in a median TTP of 6 weeks and a median OS of 6.4 months, while pemetrexed achieved 2 responses among 43 patients (ORR, 4%) (Jalal et al., 2009, J Thorac Oncol 4:93-6). Thus, progress in the management of patients with SCLC, especially those with extensive disease, has been disappointing over the past 20 years. Nearly all patients relapse early and die within a year.

A need exists for more efficacious treatment for patients with SCLC of first-line or later stages. A particular need exists for better therapies for patients who are resistant to standard chemotherapies, such as platinum-containing chemotherapy, topotecan or irinotecan.

SUMMARY

The present invention concerns improved methods and compositions for treating SCLC, either first-line or else second-line or later. The methods and compositions are of particular use in treating SCLC patients who are resistant to standard chemotherapies, such as with platinum-based or camptothecin compounds like irinotecan and topotecan. The subject methods involve treatment with an anti-Trop-2 ADC, preferably with an anti-Trop-2-SN-38 ADC. In more preferred embodiments, a linker such as a CL2A linker is used to attach the antibody moeity to the drug moiety. Most preferably, the anti-Trop-2 is a humanized RS7 (hRS7) antibody or antigen-binding antibody fragment. The instant methods and compositions provide substantially improved treatment over the standard of care for SCLC, with greater efficacy and only manageable toxicities when used at preferred dosages discussed in detail below.

In various embodiments, the ADC may be used alone or as a combination therapy with one or more other therapeutic modalities, such as surgery, radiation therapy, chemotherapy, immunomodulators, cytokines, chemotherapeutic agents, pro-apoptotic agents, anti-angiogenic agents, cytotoxic agents, drugs, toxins, radionuclides, RNAi, siRNA, a second antibody or antibody fragment, or an immunoconjugate. Preferably, the combination of ADC and other therapeutic modality is more efficacious than either alone, or the sum of the effects of individual treatments.

In a specific embodiment, an anti-Trop-2 antibody may be a humanized RS7 antibody (see, e.g., U.S. Pat. No. 7,238, 785, the Figures and Examples section of which are incorporated herein by reference), comprising the light chain CDR sequences CDR1 (KASQDVSIAVA, SEQ ID NO:1); CDR2 (SASYRYT, SEQ ID NO:2); and CDR3 (QQHYIT-PLT, SEQ ID NO:3) and the heavy chain CDR sequences CDR1 (NYGMN, SEQ ID NO:4); CDR2 (WINTYTGEP-TYTDDFKG, SEQ ID NO:5) and CDR3 (GGFGSSY-WYFDV, SEQ ID NO:6). However, as discussed below other anti-Trop-2 antibodies are known and may be used in the subject ADCs. A number of cytotoxic drugs of use for cancer treatment are well-known in the art and any such known drug may be conjugated to the antibody of interest.

In a more preferred embodiment, the drug conjugated to the antibody is a camptothecin, most preferably SN-38 (see, e.g., U.S. Pat. No. 9,028,833, the Figures and Examples section incorporated herein by reference).

The antibody moiety may be a monoclonal antibody, an antigen-binding antibody fragment, a bispecific or other multivalent antibody, or other antibody-based molecule. The antibody can be of various isotypes, preferably human IgG1, IgG2, IgG3 or IgG4, more preferably comprising human IgG1 hinge and constant region sequences. The antibody or fragment thereof can be a chimeric, a humanized, or a human antibody, as well as variations thereof, such as half-IgG4 antibodies (referred to as "unibodies"), as described by van der Neut Kolfschoten et al. (*Science* 2007; 317:1554-1557). More preferably, the antibody or fragment thereof may be designed or selected to comprise human constant region sequences that belong to specific allotypes, which may result in reduced immunogenicity when the ADC is administered to a human subject. Preferred allotypes for administration include a non-G1m1 allotype (nG1m1), such as G1m3, G1m3,1, G1m3,2 or G1m3,1,2. More preferably, the allotype is selected from the group consisting of the nG1m1, G1m3, nG1m1,2 and Km3 allotypes (Jefferies and Lefranc, 2009, mAbs 1(4):1-7).

The drug to be conjugated to the antibody or antibody fragment may be selected from the group consisting of an anthracycline, a camptothecin, a tubulin inhibitor, a maytansinoid, a calicheamycin, an auristatin, a nitrogen mustard, an ethylenimine derivative, an alkyl sulfonate, a nitrosourea, a triazene, a folic acid analog, a taxane, a COX-2 inhibitor, a pyrimidine analog, a purine analog, an antibiotic, an enzyme inhibitor, an epipodophyllotoxin, a platinum coordination complex, a *vinca* alkaloid, a substituted urea, a methyl hydrazine derivative, an adrenocortical suppressant, a hormone antagonist, an antimetabolite, an alkylating agent, an antimitotic, an anti-angiogenic agent, a tyrosine kinase inhibitor, an mTOR inhibitor, a heat shock protein (HSP90) inhibitor, a proteosome inhibitor, an HDAC inhibitor, a pro-apoptotic agent, and a combination thereof.

Specific drugs of use may be selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatinum, COX-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, DM1, DM3, DM4, doxorubicin, 2-pyrrolinodoxorubicine (2-PDox), a pro-drug form of 2-PDox (pro-2-PDox), cyanomorpholino doxorubicin, doxorubicin glucuronide, endostatin, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, monomethylauristatin F (MMAF), monomethylauristatin D (MMAD), monomethylauristatin E (MMAE), navelbine, neratinib, nilotinib, nitrosurea, olaparib, plicomycin, procarbazine, paclitaxel, PCI-32765, pentostatin, PSI-341, raloxifene, semustine, SN-38, sorafenib, streptozocin, SU11248, sunitinib, tamoxifen, temazolomide, transplatinum, thalidomide, thioguanine, thiotepa, teniposide, topotecan, uracil mustard, vatalanib, vinorelbine, vinblastine, vincristine, vinca alkaloids and ZD1839. Preferably, the drug is SN-38.

Preferred optimal dosing of the subject ADCs may include a dosage of between 4 mg/kg and 18 mg/kg, preferably given either weekly, twice weekly or every other week. The optimal dosing schedule may include treatment cycles of two consecutive weeks of therapy followed by one, two, three or four weeks of rest, or alternating weeks of therapy and rest, or one week of therapy followed by two, three or four weeks of rest, or three weeks of therapy followed by one, two, three or four weeks of rest, or four weeks of therapy followed by one, two, three or four weeks of rest, or five weeks of therapy followed by one, two, three, four or five weeks of rest, or administration once every two weeks, once every three weeks or once a month. Treatment may be extended for any number of cycles, preferably at least 2, at least 4, at least 6, at least 8, at least 10, at least 12, at least 14, or at least 16 cycles. Exemplary dosages of use may include 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg and 24 mg/kg. Preferred dosages are 4, 6, 8, 9, 10, 12, 14, 16 or 18 mg/kg. More preferred dosages are 6-12, 6-8, 7-8, 8-10, 10-12 or 8-12 mg/kg. The person of ordinary skill will realize that a variety of factors, such as age, general health, specific organ function or weight, as well as effects of prior therapy on specific organ systems (e.g., bone marrow) may be considered in selecting an optimal dosage of ADC, and that the dosage and/or frequency of administration may be increased or decreased during the course of therapy. The dosage may be repeated as needed, with evidence of tumor shrinkage observed after as few as 4 to 8 doses. The optimized dosages and schedules of administration disclosed herein show unexpected superior efficacy and reduced toxicity in human subjects, which could not have been predicted from animal model studies. Surprisingly, the superior efficacy allows treatment of tumors that were previously found to be resistant to one or more standard anti-cancer therapies. More surprisingly, the treatment has been found effective in tumors that were previously resistant to camptothecins, such as irinotecan, the parent compound of SN-38.

The ADCs are of use for therapy of cancers, such as SCLC and mSCLC. Such use may be first-line, second-line, or at later stages of cancer progression. The compositions and methods of use are efficacious in camptothecin-resistant as well as camptothecin sensitive cancers. Generally, the anti-Trop-2 ADCs are of use for treating any cancer that expresses the Trop-2 antigen. However, in a preferred specific embodiment, the cancer is SCLC or mSCLC.

DETAILED DESCRIPTION

Definitions

Figure 1:
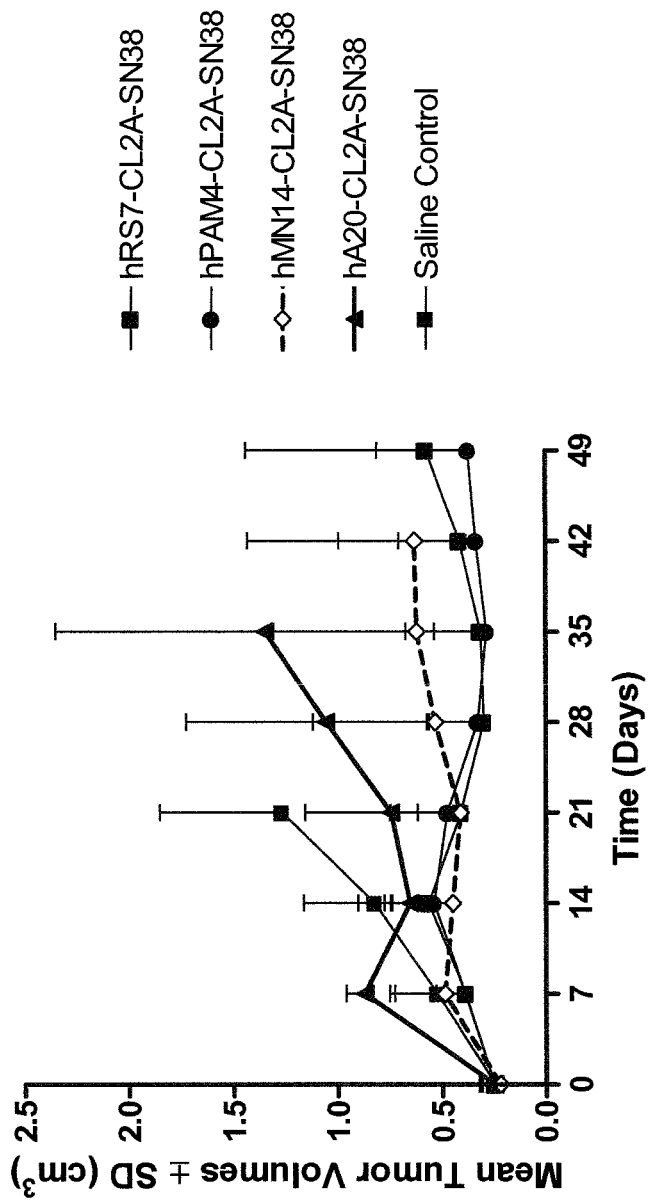
FIG. 1. Preclinical in vivo therapy of athymic nude mice, bearing Capan 1 human pancreatic carcinoma, with SN-38 conjugates of hRS7 (anti-Trop-2), hPAM4 (anti-MUC5ac), hMN-14 (anti-CEACAM5) or non-specific control hA20 (anti-CD20).

Unless otherwise specified, "a" or "an" means one or more.

As used herein, "about" means plus or minus 10%. For example, "about 100" would include any number between 90 and 110.

An antibody, as described herein, refers to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

An antibody fragment is a portion of an antibody such as F(ab')$_2$, Fab', Fab, Fv, sFv and the like. Antibody fragments may also include single domain antibodies and IgG4 half-molecules, as discussed below. Regardless of structure, an antibody fragment binds with the same antigen that is recognized by the full-length antibody. The term "antibody fragment" also includes isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins").

A chimeric antibody is a recombinant protein that contains the variable domains including the complementarity determining regions (CDRs) of an antibody derived from one species, preferably a rodent antibody, while the constant domains of the antibody molecule are derived from those of a human antibody. For veterinary applications, the constant domains of the chimeric antibody may be derived from that of other species, such as a cat or dog.

A humanized antibody is a recombinant protein in which the CDRs from an antibody from one species; e.g., a rodent antibody, are transferred from the heavy and light variable chains of the rodent antibody into human heavy and light variable domains (e.g., framework region sequences). The constant domains of the antibody molecule are derived from those of a human antibody. In certain embodiments, a limited number of framework region amino acid residues from the parent (rodent) antibody may be substituted into the human antibody framework region sequences.

A human antibody is, e.g., an antibody obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous murine heavy chain and light chain loci. The transgenic mice can synthesize human antibodies specific for particular antigens, and the mice can be used to produce human antibody-secreting hybridomas. Methods for obtaining human antibodies from transgenic mice are described by Green et al., Nature Genet. 7:13 (1994), Lonberg et al., Nature 368:856 (1994), and Taylor et al., Int. Immun. 6:579 (1994). A fully human antibody also can be constructed by genetic or chromosomal transfection methods, as well as phage display technology, all of which are known in the art. See for example, McCafferty et al., Nature 348:552-553 (1990) for the production of human antibodies and fragments thereof in vitro, from immunoglobulin variable domain gene repertoires from unimmunized donors. In this technique, antibody variable domain genes are cloned in-frame into either a major or minor coat protein gene of a filamentous bacteriophage, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. In this way, the phage mimics some of the properties of the B cell. Phage display can be performed in a variety of formats, for review, see e.g. Johnson and Chiswell, Current Opinion in Structural Biology 3:5564-571 (1993). Human antibodies may also be generated by in vitro activated B cells. See U.S. Pat. Nos. 5,567,610 and 5,229,275, the Examples section of which are incorporated herein by reference.

A therapeutic agent is a compound, molecule or atom which is administered separately, concurrently or sequentially with an antibody moiety or conjugated to an antibody moiety, i.e., antibody or antibody fragment, or a subfragment, and is useful in the treatment of a disease. Examples of therapeutic agents include antibodies, antibody fragments, drugs, toxins, nucleases, hormones, immunomodulators, pro-apoptotic agents, anti-angiogenic agents, boron compounds, photoactive agents or dyes and radioisotopes. Therapeutic agents of use are described in more detail below.

An immunoconjugate is an antibody, antibody fragment or fusion protein conjugated to at least one therapeutic and/or diagnostic agent.

A multispecific antibody is an antibody that can bind simultaneously to at least two targets that are of different structure, e.g., two different antigens, two different epitopes on the same antigen, or a hapten and/or an antigen or epitope. Multispecific, multivalent antibodies are constructs that have more than one binding site, and the binding sites are of different specificity.

A bispecific antibody is an antibody that can bind simultaneously to two different targets. Bispecific antibodies (bsAb) and bispecific antibody fragments (bsFab) may have at least one arm that specifically binds to, for example, a tumor-associated antigen and at least one other arm that specifically binds to a targetable conjugate that bears a therapeutic or diagnostic agent. A variety of bispecific fusion proteins can be produced using molecular engineering.

Anti-Trop-2 Antibodies

The subject ADCs may include an antibody or fragment thereof that binds to Trop-2. In a specific preferred embodiment, the anti-Trop-2 antibody may be a humanized RS7 antibody (see, e.g., U.S. Pat. No. 7,238,785, incorporated herein by reference in its entirety), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYDDFKG, SEQ ID NO:5) and CDR3 (GGFGSSYWYFDV, SEQ ID NO:6).

The RS7 antibody was a murine IgG$_1$ raised against a crude membrane preparation of a human primary squamous cell lung carcinoma. (Stein et al., Cancer Res. 50: 1330, 1990) The RS7 antibody recognizes a 46-48 kDa glycoprotein, characterized as cluster 13. (Stein et al., Int. J. Cancer Supp. 8:98-102, 1994) The antigen was designated as EGP-1 (epithelial glycoprotein-1), but is also referred to as Trop-2.

Trop-2 is a type-I transmembrane protein and has been cloned from both human (Fornaro et al., Int J Cancer 1995; 62:610-8) and mouse cells (Sewedy et al., Int J Cancer 1998; 75:324-30). In addition to its role as a tumor-associated calcium signal transducer (Ripani et al., Int J Cancer 1998; 76:671-6), the expression of human Trop-2 was shown to be necessary for tumorigenesis and invasiveness of colon cancer cells, which could be effectively reduced with a polyclonal antibody against the extracellular domain of Trop-2 (Wang et al., Mol Cancer Ther 2008; 7:280-5).

The growing interest in Trop-2 as a therapeutic target for solid cancers (Cubas et al., Biochim Biophys Acta 2009; 1796:309-14) is attested by further reports that documented the clinical significance of overexpressed Trop-2 in breast (Huang et al., Clin Cancer Res 2005; 11:4357-64), colorectal (Ohmachi et al., Clin Cancer Res 2006; 12:3057-63; Fang et al., Int J Colorectal Dis 2009; 24:875-84), and oral squamous cell (Fong et al., Modern Pathol 2008; 21:186-91) carcinomas. The latest evidence that prostate basal cells expressing high levels of Trop-2 are enriched for in vitro and in vivo stem-like activity is particularly noteworthy (Goldstein et al., Proc Natl Acad Sci USA 2008; 105:20882-7).

Flow cytometry and immunohistochemical staining studies have shown that the RS7 MAb detects antigen on a variety of tumor types, with limited binding to normal human tissue (Stein et al., 1990). Trop-2 is expressed primarily by carcinomas such as carcinomas of the lung, stomach, urinary bladder, breast, ovary, uterus, and prostate. Localization and therapy studies using radiolabeled murine RS7 MAb in animal models have demonstrated tumor targeting and therapeutic efficacy (Stein et al., 1990; Stein et al., 1991).

Strong RS7 staining has been demonstrated in tumors from the lung, breast, bladder, ovary, uterus, stomach, and prostate. (Stein et al., Int. J. Cancer 55:938, 1993) The lung cancer cases comprised both squamous cell carcinomas and adenocarcinomas. (Stein et al., Int. J. Cancer 55:938, 1993) Both cell types stained strongly, indicating that the RS7 antibody does not distinguish between histologic classes of non-small-cell carcinoma of the lung.

The RS7 MAb is rapidly internalized into target cells (Stein et al., 1993). The internalization rate constant for RS7 MAb is intermediate between the internalization rate constants of two other rapidly internalizing MAbs, which have been demonstrated to be useful for immunotoxin production. (Id.) It is well documented that internalization of immunotoxin conjugates is a requirement for anti-tumor activity. (Pastan et al., Cell 47:641, 1986) Internalization of drug immunoconjugates has been described as a major factor in anti-tumor efficacy. (Yang et al., Proc. Nat'l Acad. Sci. USA 85: 1189, 1988) Thus, the RS7 antibody exhibits several important properties for therapeutic applications.

While the hRS7 antibody is preferred, other anti-Trop-2 antibodies are known and/or publicly available and in alternative embodiments may be utilized in the subject ADCs. While humanized or human antibodies are preferred for reduced immunogenicity, in alternative embodiments a chimeric antibody may be of use. As discussed below, methods of antibody humanization are well known in the art and may be utilized to convert an available murine or chimeric antibody into a humanized form.

Anti-Trop-2 antibodies are commercially available from a number of sources and include LS-C126418, LS-C178765, LS-C126416, LS-C126417 (LifeSpan BioSciences, Inc., Seattle, Wash.); 10428-MM01, 10428-MM02, 10428-R001, 10428-R030 (Sino Biological Inc., Beijing, China); MR54 (eBioscience, San Diego, Calif.); sc-376181, sc-376746, Santa Cruz Biotechnology (Santa Cruz, Calif.); MM0588-49D6, (Novus Biologicals, Littleton, Colo.); ab79976, and ab89928 (ABCAM®, Cambridge, Mass.).

Other anti-Trop-2 antibodies have been disclosed in the patent literature. For example, U.S. Publ. No. 2013/0089872 discloses anti-Trop-2 antibodies K5-70 (Accession No. FERM BP-11251), K5-107 (Accession No. FERM BP-11252), K5-116-2-1 (Accession No. FERM BP-11253), T6-16 (Accession No. FERM BP-11346), and T5-86 (Accession No. FERM BP-11254), deposited with the International Patent Organism Depositary, Tsukuba, Japan. U.S. Pat. No. 5,840,854 disclosed the anti-Trop-2 monoclonal antibody BR110 (ATCC No. HB11698). U.S. Pat. No. 7,420,040 disclosed an anti-Trop-2 antibody produced by hybridoma cell line AR47A6.4.2, deposited with the IDAC (International Depository Authority of Canada, Winnipeg, Canada) as accession number 141205-05. U.S. Pat. No. 7,420,041 disclosed an anti-Trop-2 antibody produced by hybridoma cell line AR52A301.5, deposited with the IDAC as accession number 141205-03. U.S. Publ. No. 2013/0122020 disclosed anti-Trop-2 antibodies 3E9, 6G11, 7E6, 15E2, 18B1. Hybridomas encoding a representative antibody were deposited with the American Type Culture Collection (ATCC), Accession Nos. PTA-12871 and PTA-12872. U.S. Pat. No. 8,715,662 discloses anti-Trop-2 antibodies produced by hybridomas deposited at the AID-ICLC (Genoa, Italy) with deposit numbers PD 08019, PD 08020 and PD 08021. U.S. Patent Application Publ. No. 20120237518 discloses anti-Trop-2 antibodies 77220, KM4097 and KM4590. U.S. Pat. No. 8,309,094 (Wyeth) discloses antibodies A1 and A3, identified by sequence listing. The Examples section of each patent or patent application cited above in this paragraph is incorporated herein by reference. Non-patent publication Lipinski et al. (1981, Proc Natl. Acad Sci USA, 78:5147-50) disclosed anti-Trop-2 antibodies 162-25.3 and 162-46.2.

Numerous anti-Trop-2 antibodies are known in the art and/or publicly available. As discussed below, methods for preparing antibodies against known antigens were routine in the art. The sequence of the human Trop-2 protein was also known in the art (see, e.g., GenBank Accession No. CAA54801.1). Methods for producing humanized, human or chimeric antibodies were also known. The person of ordinary skill, reading the instant disclosure in light of general knowledge in the art, would have been able to make and use the genus of anti-Trop-2 antibodies in the subject ADCs.

Use of anti-Trop-2 antibodies has been disclosed for immunotherapeutics other than ADCs. The murine IgG2a antibody edrecolomab (PANOREX®) has been used for treatment of colorectal cancer, although the murine antibody is not well suited for human clinical use (Baeuerle & Gires, 2007, Br. J Cancer 96:417-423). Low-dose subcutaneous administration of ecrecolomab was reported to induce humoral immune responses against the vaccine antigen (Baeuerle & Gires, 2007). Adecatumumab (MT201), a fully human anti-Trop-2 antibody, has been used in metastatic breast cancer and early-stage prostate cancer and is reported to act through ADCC and CDC activity (Baeuerle & Gires, 2007). MT110, a single-chain anti-Trop-2/anti-CD3 bispecific antibody construct has reported efficacy against ovarian cancer (Baeuerle & Gires, 2007). Catumaxomab, a hybrid mouse/rat antibody with binding affinity for Trop-2, CD3 and Fc receptor, was reported to be active against ovarian cancer (Baeuerle & Gires, 2007). Proxinium, an immunotoxin comprising anti-Trop-2 single-chain antibody fused to *Pseudomonas* exotoxin, has been tested in head-and-neck and bladder cancer (Baeuerle & Gires, 2007). None of these studies contained any disclosure of the use of anti-Trop-2 antibody-drug conjugates.

Camptothecin Conjugates

Non-limiting methods and compositions for preparing immunoconjugates comprising a camptothecin therapeutic agent attached to an antibody or antigen-binding antibody fragment are described below. In preferred embodiments, the solubility of the drug is enhanced by placing a defined polyethyleneglycol (PEG) moiety (i.e., a PEG containing a defined number of monomeric units) between the drug and the antibody, wherein the defined PEG is a low molecular weight PEG, preferably containing 1-30 monomeric units, more preferably containing 1-12 monomeric units, most preferably containing 6-8 monomeric units.

Preferably, a first linker connects the drug at one end and may terminate with an acetylene or an azide group at the other end. This first linker may comprise a defined PEG moiety with an azide or acetylene group at one end and a different reactive group, such as carboxylic acid or hydroxyl group, at the other end. Said bifunctional defined PEG may be attached to the amine group of an amino alcohol, and the hydroxyl group of the latter may be attached to the hydroxyl group on the drug in the form of a carbonate. Alternatively, the non-azide(or acetylene) moiety of said defined bifunctional PEG is optionally attached to the N-terminus of an L-amino acid or a polypeptide, with the C-terminus attached to the amino group of amino alcohol, and the hydroxy group of the latter is attached to the hydroxyl group of the drug in the form of carbonate or carbamate, respectively.

A second linker, comprising an antibody-coupling group and a reactive group complementary to the azide (or acetylene) group of the first linker, namely acetylene (or azide), may react with the drug-(first linker) conjugate via acetylene-azide cycloaddition reaction to furnish a final bifunctional drug product that is useful for conjugating to disease-targeting antibodies. The antibody-coupling group is preferably either a thiol or a thiol-reactive group.

Methods for selective regeneration of the 10-hydroxyl group in the presence of the C-20 carbonate in preparations of drug-linker precursor involving CPT analogs such as SN-38 are provided below. Other protecting groups for reactive hydroxyl groups in drugs such as the phenolic hydroxyl in SN-38, for example t-butyldimethylsilyl or t-butyldiphenylsilyl, may also be used, and these are deprotected by tetrabutylammonium fluoride prior to linking of the derivatized drug to an antibody-coupling moiety. The 10-hydroxyl group of CPT analogs is alternatively protected as an ester or carbonate, other than 'BOC', such that the bifunctional CPT is conjugated to an antibody without prior deprotection of this protecting group. The protecting group is readily deprotected under physiological pH conditions after the bioconjugate is administered.

In the acetylene-azide coupling, referred to as 'click chemistry', the azide part may be on L2 with the acetylene part on L3. Alternatively, L2 may contain acetylene, with L3 containing azide. 'Click chemistry' refers to a copper (+1)-catalyzed cycloaddition reaction between an acetylene moiety and an azide moiety (Kolb H C and Sharpless K B, *Drug Discov Today* 2003; 8: 1128-37), although alternative forms of click chemistry are known and may be used. Click chemistry takes place in aqueous solution at near-neutral pH conditions, and is thus amenable for drug conjugation. The advantage of click chemistry is that it is chemoselective, and complements other well-known conjugation chemistries such as the thiol-maleimide reaction.

An exemplary preferred embodiment is directed to a conjugate of a drug derivative and an antibody of the general formula (1) shown below.

$$\text{MAb-[L2]-[L1]-[AA]}_m\text{-[A']-Drug} \quad (1)$$

where MAb is a disease-targeting antibody; L2 is a component of the cross-linker comprising an antibody-coupling moiety and one or more of acetylene (or azide) groups; L1 comprises a defined PEG with azide (or acetylene) at one end, complementary to the acetylene (or azide) moiety in L2, and a reactive group such as carboxylic acid or hydroxyl group at the other end; AA is an L-amino acid; m is an integer with values of 0, 1, 2, 3, or 4; and A' is an additional spacer, selected from the group of ethanolamine, 4-hydroxybenzyl alcohol, 4-aminobenzyl alcohol, or substituted or unsubstituted ethylenediamine. The L amino acids of 'AA' are selected from alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. If the A' group contains hydroxyl, it is linked to the hydroxyl group or amino group of the drug in the form of a carbonate or carbamate, respectively.

In a preferred embodiment of formula 1, A' is a substituted ethanolamine derived from an L-amino acid, wherein the carboxylic acid group of the amino acid is replaced by a hydroxymethyl moiety. A' may be derived from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine.

In an example of the conjugate of the preferred embodiment of formula 1, m is 0, A' is L-valinol, and the drug is exemplified by SN-38. In another example of formula 1, m is 1 and represented by a derivatized L-lysine, A' is L-valinol, and the drug is exemplified by SN-38. In this embodiment, an amide bond is first formed between the carboxylic acid of an amino acid such as lysine and the amino group of valinol, using orthogonal protecting groups for the lysine amino groups. The protecting group on the N-terminus of lysine is removed, keeping the protecting group on the side chain of lysine intact, and the N-terminus is coupled to the carboxyl group on the defined PEG with azide (or acetylene) at the other end. The hydroxyl group of valinol is then attached to the 20-chloroformate derivative of 10-hydroxy-protected SN-38, and this intermediate is coupled to an L2 component carrying the antibody-binding moiety as well as the complementary acetylene (or azide) group involved in the click cycloaddition chemistry. Finally, removal of protecting groups at both lysine side chain and SN-38 gives the product of this example.

While not wishing to be bound by theory, the small MW SN-38 product, namely valinol-SN-3 8 carbonate, generated after intracellular proteolysis, has the additional pathway of liberation of intact SN-38 through intramolecular cyclization involving the amino group of valinol and the carbonyl of the carbonate.

In another preferred embodiment, A' of the general formula 1 is A-OH, whereby A-OH is a collapsible moiety such as 4-aminobenzyl alcohol or a substituted 4-aminobenzyl alcohol substituted with a $C_1$-$C_{10}$ alkyl group at the benzylic position, and the latter, via its amino group, is attached to an L-amino acid or a polypeptide comprising up to four L-amino acid moieties; wherein the N-terminus is attached to a cross-linker terminating in the antibody-binding group.

In another example of a preferred embodiment, the A-OH of A' of general formula 1 is derived from a substituted 4-aminobenzyl alcohol, and 'AA' is comprised of a single L-amino acid with m=1 in the general formula 1, and the drug is exemplified with SN-38. Single amino acid of AA may be selected from any one of the following L-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, and valine. The substituent R on 4-aminobenzyl alcohol moiety (A-OH embodiment of A') is hydrogen or an alkyl group selected from C1-C10 alkyl groups. An example of this formula, wherein the single amino acid AA is L-lysine and R=H, and the drug is exemplified by SN-38 is referred to as MAb-CL2A-SN-38 (shown below). The structure differs from the linker MAb-CL2-SN-3 8 in the substitution of a single lysine residue for a Phe-Lys dipeptide found in the CL2 linker. The Phe-Lys dipeptide was designed as a cathepsin B cleavage site for lysosomal enzyme, which was considered to be important for intracellular release of bound drug. Surprisingly, despite the elimination of the cathepsin-cleavage site, immunoconjugates comprising a CL2A linker are apparently more efficacious in vivo than those comprising a CL2 linker.

tions of MAb's lysine groups are well known in the art (Wong in *Chemistry of protein conjugation and cross-linking*, CRC Press, Inc., Boca Raton, Fla. (1991), pp 20-22). Alternatively, mild reduction of interchain disulfide bonds on the antibody (Willner et al., *Bioconjugate Chem.* 4:521-527 (1993)) using reducing agents such as dithiothreitol (DTT) can generate 7-to-10 thiols on the antibody; which has the advantage of incorporating multiple drug moieties in the interchain region of the MAb away from the antigen-binding region. In a more preferred embodiment, attachment of SN-38 to reduced disulfide sulfhydryl groups results in formation of an antibody-SN-38 immunoconjugate with 6 to 8 SN-38 moieties covalently attached per antibody molecule. Other methods of providing cysteine residues for attachment of drugs or other therapeutic agents are known, such as the use of cysteine engineered antibodies (see U.S. Pat. No. 7,521,541, the Examples section of which is incorporated herein by reference.)

In alternative preferred embodiments, the chemotherapeutic moiety is selected from the group consisting of doxorubicin (DOX), epirubicin, morpholinodoxorubicin (morpholino-DOX), cyanomorpholino-doxorubicin (cyanomorpholino-DOX), 2-pyrrolino-doxorubicin (2-PDOX), Pro-2PDOX, CPT, 10-hydroxy camptothecin, SN-38, topotecan, lurtotecan, 9-aminocamptothecin, 9-nitrocamptothecin, taxanes, geldanamycin, ansamycins, and epothilones.

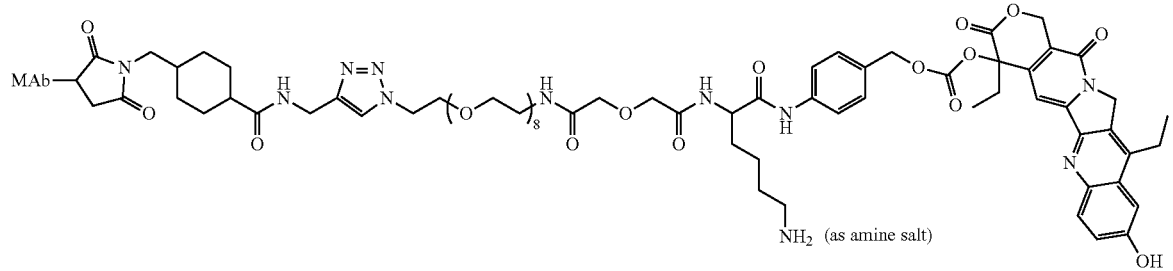

MAb-CL2A-SN-38

In a preferred embodiment, AA comprises a polypeptide moiety, preferably a di, tri or tetrapeptide, that is cleavable by intracellular peptidase. Examples are: Ala-Leu, Leu-Ala-Leu, and Ala-Leu-Ala-Leu (SEQ ID NO: 9) (Trouet et al., 1982).

In another preferred embodiment, the L1 component of the conjugate contains a defined polyethyleneglycol (PEG) spacer with 1-30 repeating monomeric units. In a further preferred embodiment, PEG is a defined PEG with 1-12 repeating monomeric units. The introduction of PEG may involve using heterobifunctionalized PEG derivatives which are available commercially. The heterobifunctional PEG may contain an azide or acetylene group.

In a preferred embodiment, L2 has a plurality of acetylene (or azide) groups, ranging from 2-40, but preferably 2-20, and more preferably 2-5, and a single antibody-binding moiety. In a representative example, the 'L2' component is appended to 2 acetylenic groups, resulting in the attachment of two azide-appended SN-38 molecules. The bonding to MAb may involve a succinimide.

In preferred embodiments, when the bifunctional drug contains a thiol-reactive moiety as the antibody-binding group, the thiols on the antibody are generated on the lysine groups of the antibody using a thiolating reagent. Methods for introducing thiol groups onto antibodies by modifica- In a more preferred embodiment, the chemotherapeutic moiety is SN-38. Preferably, in the conjugates of the preferred embodiments, the antibody links to at least one chemotherapeutic moiety; preferably 1 to about 12 chemotherapeutic moieties; most preferably about 6 to about 8 chemotherapeutic moieties.

Furthermore, in a preferred embodiment, the linker component 'L2' comprises a thiol group that reacts with a thiol-reactive residue introduced at one or more lysine side chain amino groups of said antibody. In such cases, the antibody is pre-derivatized with a thiol-reactive group such as a maleimide, vinylsulfone, bromoacetamide, or iodoacetamide by procedures well described in the art.

In the context of this work, a process was surprisingly discovered by which CPT drug-linkers can be prepared wherein CPT additionally has a 10-hydroxyl group. This process involves, but is not limited to, the protection of the 10-hydroxyl group as a t-butyloxycarbonyl (BOC) derivative, followed by the preparation of the penultimate intermediate of the drug-linker conjugate. Usually, removal of the BOC group requires treatment with strong acid such as trifluoroacetic acid (TFA). Under these conditions, the CPT 20-O-linker carbonate, containing protecting groups to be removed, is also susceptible to cleavage, thereby giving rise to unmodified CPT. In fact, the rationale for using a mildly removable methoxytrityl (MMT) protecting group for the lysine side chain of the linker molecule, as enunciated in the art, was precisely to avoid this possibility (Walker et al., 2002). It was discovered that selective removal of phenolic BOC protecting group is possible by carrying out reactions for short durations, optimally 3-to-5 minutes. Under these conditions, the predominant product was that in which the 'BOC' at 10-hydroxyl position was removed, while the carbonate at '20' position was intact.

An alternative approach involves protecting the CPT analog's 10-hydroxy position with a group other than 'BOC', such that the the final product is ready for conjugation to antibodies without a need for deprotecting the 10-OH protecting group. The 10-hydroxy protecting group, which converts the 10-OH into a phenolic carbonate or a phenolic ester, is readily deprotected by physiological pH conditions or by esterases after in vivo administration of the conjugate. The faster removal of a phenolic carbonate at the 10 position vs. a tertiary carbonate at the 20 position of 10-hydroxycamptothecin under physiological condition has been described by He et al. (He et al., *Bioorganic & Medicinal Chemistry* 12: 4003-4008 (2004)). A 10-hydroxy protecting group on SN-38 can be 'COR' where R can be a substituted alkyl such as "$N(CH_3)_2$—$(CH_2)_n$—" where n is 1-10 and wherein the terminal amino group is optionally in the form of a quaternary salt for enhanced aqueous solubility, or a simple alkyl residue such as "$CH_3$—$(CH_2)_n$—" where n is 0-10, or it can be an alkoxy moiety such as "$CH_3$—$(CH_2)$ n-O—" where n is 0-10, or "$N(CH_3)_2$—$(CH_2)_n$—O—" where n is 2-10, or "$R_1O$—$(CH_2$—$CH_2$—$O)_n$—$CHCH_2$—$CH_2$—O—" where $R_1$ is ethyl or methyl and n is an integer with values of 0-10. These 10-hydroxy derivatives are readily prepared by treatment with the chloroformate of the chosen reagent, if the final derivative is to be a carbonate. Typically, the 10-hydroxy-containing camptothecin such as SN-38 is treated with a molar equivalent of the chloroformate in dimethylformamide using triethylamine as the base. Under these conditions, the 20-OH position is unaffected. For forming 10-O-esters, the acid chloride of the chosen reagent is used.

In a preferred process of the preparation of a conjugate of a drug derivative and an antibody of the general formula 1, wherein the descriptors L2, L1, AA and A-X are as described in earlier sections, the bifunctional drug moiety, [L2]-[L1]-[AA]$_m$-[A-X]-Drug is first prepared, followed by the conjugation of the bifunctional drug moiety to the antibody (indicated herein as "MAb").

In a preferred process of the preparation of a conjugate of a drug derivative and an antibody of the general formula 1, wherein the descriptors L2, L1, AA and A-OH are as described in earlier sections, the bifunctional drug moiety is prepared by first linking A-OH to the C-terminus of AA via an amide bond, followed by coupling the amine end of AA to a carboxylic acid group of L1. If AA is absent (i.e. m=0), A-OH is directly attached to L1 via an amide bond. The cross-linker, [L1]-[AA]$_m$-[A-OH], is attached to drug's hydroxyl or amino group, and this is followed by attachment to the L1 moiety, by taking recourse to the reaction between azide (or acetylene) and acetylene (or azide) groups in L1 and L2 via click chemistry.

In one embodiment, the antibody is a monoclonal antibody (MAb). In other embodiments, the antibody may be a multivalent and/or multispecific MAb. The antibody may be a murine, chimeric, humanized, or human monoclonal antibody, and said antibody may be in intact, fragment (Fab, Fab', F(ab)$_2$, F(ab')$_2$), or sub-fragment (single-chain constructs) form, or of an IgG1, IgG2a, IgG3, IgG4, IgA isotype, or submolecules therefrom.

Antibody Preparation

Techniques for preparing monoclonal antibodies against virtually any target antigen, such as Trop-2, are well known in the art. See, for example, Köhler and Milstein, *Nature* 256: 495 (1975), and Coligan et al. (eds.), CURRENT PROTOCOLS IN IMMUNOLOGY, VOL. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., "Purification of Immunoglobulin G (IgG)," in METHODS IN MOLECULAR BIOLOGY, VOL. 10, pages 79-104 (The Humana Press, Inc. 1992).

Various techniques, such as production of chimeric or humanized antibodies, may involve procedures of antibody cloning and construction. The antigen-binding $V_\kappa$ (variable light chain) and $V_H$ (variable heavy chain) sequences for an antibody of interest may be obtained by a variety of molecular cloning procedures, such as RT-PCR, 5'-RACE, and cDNA library screening. The V genes of a MAb from a cell that expresses a murine MAb can be cloned by PCR amplification and sequenced. To confirm their authenticity, the cloned $V_L$ and $V_H$ genes can be expressed in cell culture as a chimeric Ab as described by Orlandi et al., (*Proc. Natl. Acad. Sci.*, USA, 86: 3833 (1989)). Based on the V gene sequences, a humanized MAb can then be designed and constructed as described by Leung et al. (*Mol. Immunol.*, 32: 1413 (1995)).

cDNA can be prepared from any known hybridoma line or transfected cell line producing a murine MAb by general molecular cloning techniques (Sambrook et al., Molecular Cloning, A laboratory manual, $2^{nd}$ Ed (1989)). The $V_\kappa$ sequence for the MAb may be amplified using the primers VK1BACK and VK1FOR (Orlandi et al., 1989) or the extended primer set described by Leung et al. (*BioTechniques*, 15: 286 (1993)). The $V_H$ sequences can be amplified using the primer pair VH1BACK/VH1FOR (Orlandi et al., 1989) or the primers annealing to the constant region of murine IgG described by Leung et al. (Hybridoma, 13:469 (1994)). Humanized V genes can be constructed by a combination of long oligonucleotide template syntheses and PCR amplification as described by Leung et al. (*Mol. Immunol.*, 32: 1413 (1995)).

PCR products for Vκ can be subcloned into a staging vector, such as a pBR327-based staging vector, VKpBR, that contains an Ig promoter, a signal peptide sequence and convenient restriction sites. PCR products for $V_H$ can be subcloned into a similar staging vector, such as the pBluescript-based VHpBS. Expression cassettes containing the Vκ and $V_H$ sequences together with the promoter and signal peptide sequences can be excised from VKpBR and VHpBS and ligated into appropriate expression vectors, such as pKh and pG1g, respectively (Leung et al., Hybridoma, 13:469 (1994)). The expression vectors can be co-transfected into an appropriate cell and supernatant fluids monitored for production of a chimeric, humanized or human MAb. Alternatively, the Vκ and $V_H$ expression cassettes can be excised and subcloned into a single expression vector, such as pdHL2, as described by Gillies et al. (*J. Immunol. Methods* 125:191 (1989) and also shown in Losman et al., *Cancer*, 80:2660 (1997)).

In an alternative embodiment, expression vectors may be transfected into host cells that have been pre-adapted for transfection, growth and expression in serum-free medium. Exemplary cell lines that may be used include the Sp/EEE, Sp/ESF and Sp/ESF-X cell lines (see, e.g., U.S. Pat. Nos. 7,531,327; 7,537,930 and 7,608,425; the Examples section of each of which is incorporated herein by reference). These exemplary cell lines are based on the Sp2/0 myeloma cell line, transfected with a mutant Bcl-EEE gene, exposed to methotrexate to amplify transfected gene sequences and pre-adapted to serum-free cell line for protein expression.

Chimeric Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. General techniques for cloning murine immunoglobulin variable domains are disclosed, for example, in Orlandi et al., *Proc. Nat'l Acad. Sci. USA* 6: 3833 (1989). Techniques for constructing chimeric antibodies are well known to those of skill in the art. As an example, Leung et al., *Hybridoma* 13:469 (1994), produced an LL2 chimera by combining DNA sequences encoding the $V_κ$ and $V_H$ domains of murine LL2, an anti-CD22 monoclonal antibody, with respective human K and $IgG_1$ constant region domains.

Humanized Antibodies

The subject ADCs may include an antibody or fragment thereof that binds to Trop-2. In a specific preferred embodiment, the anti-Trop-2 antibody may be a humanized RS7 antibody (see, e.g., U.S. Pat. No. 7,238,785, incorporated herein by reference in its entirety), comprising the light chain CDR sequences CDR1 (KASQDVSIAVA, SEQ ID NO:1); CDR2 (SASYRYT, SEQ ID NO:2); and CDR3 (QQHYITPLT, SEQ ID NO:3) and the heavy chain CDR sequences CDR1 (NYGMN, SEQ ID NO:4); CDR2 (WINTYTGEPTYTDDFKG, SEQ ID NO:5) and CDR3 (GGF-GSSYWYFDV, SEQ ID NO:6).

Techniques for producing humanized MAbs are well known in the art (see, e.g., Jones et al., *Nature* 321: 522 (1986), Riechmann et al., *Nature* 332: 323 (1988), Verhoeyen et al., *Science* 239: 1534 (1988), Carter et al., *Proc. Nat'l Acad. Sci. USA* 89: 4285 (1992), Sandhu, *Crit. Rev. Biotech.* 12: 437 (1992), and Singer et al., *J. Immun.* 150: 2844 (1993)). A chimeric or murine monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. As simply transferring mouse CDRs into human FRs often results in a reduction or even loss of antibody affinity, additional modification might be required in order to restore the original affinity of the murine antibody. This can be accomplished by the replacement of one or more human residues in the FR regions with their murine counterparts to obtain an antibody that possesses good binding affinity to its epitope. See, for example, Tempest et al., *Biotechnology* 9:266 (1991) and Verhoeyen et al., *Science* 239: 1534 (1988). Preferred residues for substitution include FR residues that are located within 1, 2, or 3 Angstroms of a CDR residue side chain, that are located adjacent to a CDR sequence, or that are predicted to interact with a CDR residue.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26; Brekke and Loset, 2003, *Curr. Opin. Pharmacol.* 3:544-50). A fully human antibody also can be constructed by genetic or chromosomal transfection methods, as well as phage display technology, all of which are known in the art. See for example, McCafferty et al., *Nature* 348:552-553 (1990). Such fully human antibodies are expected to exhibit even fewer side effects than chimeric or humanized antibodies and to function in vivo as essentially endogenous human antibodies.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.). Recombinant Fab were cloned from the μ, γ and κ chain antibody repertoires and inserted into a phage display library (Id.). RNAs were converted to cDNAs and used to make Fab cDNA libraries using specific primers against the heavy and light chain immunoglobulin sequences (Marks et al., 1991, *J. Mol. Biol.* 222:581-97). Library construction was performed according to Andris-Widhopf et al. (2000, In: *Phage Display Laboratory Manual*, Barbas et al. (eds), $1^{st}$ edition, Cold Spring Harbor Laboratory Press, Cold Spring Harbor, N.Y. pp. 9.1 to 9.22). The final Fab fragments were digested with restriction endonucleases and inserted into the bacteriophage genome to make the phage display library. Such libraries may be screened by standard phage display methods, as known in the art. Phage display can be performed in a variety of formats, for their review, see e.g. Johnson and Chiswell, *Current Opinion in Structural Biology* 3:5564-571 (1993).

Human antibodies may also be generated by in vitro activated B-cells. See U.S. Pat. Nos. 5,567,610 and 5,229,275, incorporated herein by reference in their entirety. The skilled artisan will realize that these techniques are exemplary and any known method for making and screening human antibodies or antibody fragments may be utilized.

In another alternative, transgenic animals that have been genetically engineered to produce human antibodies may be used to generate antibodies against essentially any immunogenic target, using standard immunization protocols. Methods for obtaining human antibodies from transgenic mice are disclosed by Green et al., *Nature Genet.* 7:13 (1994), Lonberg et al., *Nature* 368:856 (1994), and Taylor et al., *Int. Immun.* 6:579 (1994). A non-limiting example of such a system is the XENOMOUSE® (e.g., Green et al., 1999, *J. Immunol. Methods* 231:11-23, incorporated herein by reference) from Abgenix (Fremont, Calif.). In the XENO- MOUSE® and similar animals, the mouse antibody genes have been inactivated and replaced by functional human antibody genes, while the remainder of the mouse immune system remains intact.

The XENOMOUSE® was transformed with germline-configured YACs (yeast artificial chromosomes) that contained portions of the human IgH and Igkappa loci, including the majority of the variable region sequences, along with accessory genes and regulatory sequences. The human variable region repertoire may be used to generate antibody producing B-cells, which may be processed into hybridomas by known techniques. A XENOMOUSE® immunized with a target antigen will produce human antibodies by the normal immune response, which may be harvested and/or produced by standard techniques discussed above. A variety of strains of XENOMOUSE® are available, each of which is capable of producing a different class of antibody. Transgenically produced human antibodies have been shown to have therapeutic potential, while retaining the pharmacokinetic properties of normal human antibodies (Green et al., 1999). The skilled artisan will realize that the claimed compositions and methods are not limited to use of the XENOMOUSE® system but may utilize any transgenic animal that has been genetically engineered to produce human antibodies.

Known Antibodies and Target Antigens

As discussed above, in preferred embodiments the ADCs are of use for treatment of cancer. In certain embodiments, the target cancer may express one or more target tumor-associated antigens (TAAs). Particular antibodies that may be of use for therapy of cancer include, but are not limited to, LL1 (anti-CD74), LL2 or RFB4 (anti-CD22), veltuzumab (hA20, anti-CD20), rituxumab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as Trop-2)), PAM4 or KC4 (both anti-mucin), MN-14 (anti-carcinoembryonic antigen (CEA, also known as CD66e or CEACAM5), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20); panitumumab (anti-EGFR); tositumomab (anti-CD20); PAM4 (aka clivatuzumab, anti-mucin) and trastuzumab (anti-ErbB2). Preferably, the antibody is an hRS7 antibody.

Such anti-TAA antibodies are known in the art (e.g., U.S. Pat. Nos. 5,686,072; 5,874,540; 6,107,090; 6,183,744; 6,306,393; 6,653,104; 6,730,300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239; and U.S. Patent Application Publ. No. 20050271671; 20060193865; 20060210475; 20070087001; the Examples section of each incorporated herein by reference.) Specific known antibodies of use include hPAM4 (U.S. Pat. No. 7,282,567), hA20 (U.S. Pat. No. 7,151,164), hA19 (U.S. Pat. No. 7,109,304), hIMMU-31 (U.S. Pat. No. 7,300,655), hLL1 (U.S. Pat. No. 7,312,318), hLL2 (U.S. Pat. No. 5,789,554), hMu-9 (U.S. Pat. No. 7,387,772), hL243 (U.S. Pat. No. 7,612,180), hMN-14 (U.S. Pat. No. 6,676,924), hMN-15 (U.S. Pat. No. 8,287,865), hR1 (U.S. Pat. No. 9,441,043), hRS7 (U.S. Pat. No. 7,238,785), hMN-3 (U.S. Pat. No. 7,541,440), AB-PG1-XG1-026 (U.S. patent application Ser. No. 11/983,372, deposited as ATCC PTA-4405 and PTA-4406) and D2/B (WO 2009/130575) the text of each recited patent or application is incorporated herein by reference with respect to the Figures and Examples sections.

Other useful tumor-associated antigens that may be targeted include carbonic anhydrase IX, B7, CCL19, CCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD47, CD52, CD54, CD55, CD59, CD64, CD67, CD70, CD74, CD79a, CD80, CD83, CD95, CD126, CD133, CD138, CD147, CD154, CEACAM5, CEACAM6, CTLA-4, alpha-fetoprotein (AFP), VEGF (e.g., AVASTIN®, fibronectin splice variant), ED-B fibronectin (e.g., L19), EGP-1 (Trop-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO-β, HMGB-1, hypoxia inducible factor (HIF), HM1.24, HER-2/neu, histone H2B, histone H3, histone H4, insulin-like growth factor (ILGF), IFN-γ, IFN-α, IFN-β, IFN-λ, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (PlGF), PSA (prostate-specific antigen), PSMA, PAM4 antigen, PD-1 receptor, PD-L1, NCA-95, NCA-90, A3, A33, Ep-CAM, KS-1, Le(y), mesothelin, S100, tenascin, TAC, Tn antigen, Thomas-Friedenreich antigens, tumor necrosis antigens, tumor angiogenesis antigens, TNF-α, TRAIL receptor (R1 and R2), Trop-2, VEGFR, RANTES, T101, as well as cancer stem cell antigens, complement factors C3, C3a, C3b, C5a, C5, and an oncogene product.

Cancer stem cells, which are ascribed to be more therapy-resistant precursor malignant cell populations (Hill and Perris, *J. Natl. Cancer Inst.* 2007; 99:1435-40), have antigens that can be targeted in certain cancer types, such as CD133 in prostate cancer (Maitland et al., *Ernst Schering Found. Sympos. Proc.* 2006; 5:155-79), non-small-cell lung cancer (Donnenberg et al., *J. Control Release* 2007; 122(3): 385-91), and glioblastoma (Beier et al., *Cancer Res.* 2007; 67(9):4010-5), and CD44 in colorectal cancer (Dalerba et al., *Proc. Natl. Acad. Sci. USA* 2007; 104(24)10158-63), pancreatic cancer (Li et al., *Cancer Res.* 2007; 67(3):1030-7), and in head and neck squamous cell carcinoma (Prince et al., *Proc. Natl. Acad. Sci. USA* 2007; 104(3)973-8). Another useful target for breast cancer therapy is the LIV-1 antigen described by Taylor et al. (*Biochem. J.* 2003; 375: 51-9).

Checkpoint inhibitor antibodies have been used in cancer therapy. Immune checkpoints refer to inhibitory pathways in the immune system that are responsible for maintaining self-tolerance and modulating the degree of immune system response to minimize peripheral tissue damage. However, tumor cells can also activate immune system checkpoints to decrease the effectiveness of immune response against tumor tissues. Exemplary checkpoint inhibitor antibodies against cytotoxic T-lymphocyte antigen 4 (CTLA4, also known as CD152), programmed cell death protein 1 (PD1, also known as CD279) and programmed cell death 1 ligand 1 (PD-L1, also known as CD274), may be used in combination with one or more other agents to enhance the effectiveness of immune response against disease cells, tissues or pathogens. Exemplary anti-PD1 antibodies include lambrolizumab (MK-3475, MERCK), nivolumab (BMS-936558, BRISTOL-MYERS SQUIBB), AMP-224 (MERCK), and pidilizumab (CT-011, CURETECH LTD.). Anti-PD1 antibodies are commercially available, for example from ABCAM® (AB137132), BIOLEGEND® (EH12.2H7, RMP1-14) and AFFYMETRIX EBIOSCIENCE (J105, J116, MIH4). Exemplary anti-PD-L1 antibodies include MDX-1105 (MEDAREX), MEDI4736 (MEDIMMUNE) MPDL3280A (GENENTECH) and BMS-936559 (BRISTOL-MYERS SQUIBB). Anti-PD-L1 antibodies are also commercially available, for example from AFFYMETRIX EBIOSCIENCE (MIH1). Exemplary anti-CTLA4 antibodies include ipilimumab (Bristol-Myers Squibb) and tremelimumab (PFIZER). Anti-PD1 antibodies are commercially available, for example from ABCAM® (AB134090), SINO BIOLOGICAL INC. (11159-H03H, 11159-H08H), and THERMO SCIENTIFIC PIERCE (PA5-29572, PA5-23967, PA5-26465, MA1-12205, MA1-35914). Ipilimumab has recently received FDA approval for treatment of metastatic melanoma (Wada et al., 2013, J Transl Med 11:89).

Macrophage migration inhibitory factor (MIF) is an important regulator of innate and adaptive immunity and apoptosis. It has been reported that CD74 is the endogenous receptor for MIF (Leng et al., 2003, *J Exp Med* 197:1467-76). The therapeutic effect of antagonistic anti-CD74 antibodies on MIF-mediated intracellular pathways may be of use for treatment of a broad range of disease states, such as cancers of the bladder, prostate, breast, lung, and colon (e.g., Meyer-Siegler et al., 2004, *BMC Cancer* 12:34; Shachar & Haran, 2011, *LeukLymphoma* 52:1446-54). Milatuzumab (hLL1) is an exemplary anti-CD74 antibody of therapeutic use for treatment of MIF-mediated diseases.

Various other antibodies of use are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; 7,642,239 and U.S. Patent Application Publ. No. 20060193865; each incorporated herein by reference.)

Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including tumor-associated antigens, have been deposited at the ATCC and/or have published variable region sequences and are available for use in the claimed methods and compositions. See, e.g., U.S. Pat. Nos. 7,312,318; 7,282,567; 7,151,164; 7,074,403; 7,060,802; 7,056,509; 7,049,060; 7,045,132; 7,041,803; 7,041,802; 7,041,293; 7,038,018; 7,037,498; 7,012,133; 7,001,598; 6,998,468; 6,994,976; 6,994,852; 6,989,241; 6,974,863; 6,965,018; 6,964,854; 6,962,981; 6,962,813; 6,956,107; 6,951,924; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 6,881,405; 6,878,812; 6,875,580; 6,872,568; 6,867,006; 6,864,062; 6,861,511; 6,861,227; 6,861,226; 6,838,282; 6,835,549; 6,835,370; 6,824,780; 6,824,778; 6,812,206; 6,793,924; 6,783,758; 6,770,450; 6,767,711; 6,764,688; 6,764,681; 6,764,679; 6,743,898; 6,733,981; 6,730,307; 6,720,155; 6,716,966; 6,709,653; 6,693,176; 6,692,908; 6,689,607; 6,689,362; 6,689,355; 6,682,737; 6,682,736; 6,682,734; 6,673,344; 6,653,104; 6,652,852; 6,635,482; 6,630,144; 6,610,833; 6,610,294; 6,605,441; 6,605,279; 6,596,852; 6,592,868; 6,576,745; 6,572,856; 6,566,076; 6,562,618; 6,545,130; 6,544,749; 6,534,058; 6,528,625; 6,528,269; 6,521,227; 6,518,404; 6,511,665; 6,491,915; 6,488,930; 6,482,598; 6,482,408; 6,479,247; 6,468,531; 6,468,529; 6,465,173; 6,461,823; 6,458,356; 6,455,044; 6,455,040; 6,451,310; 6,444,206' 6,441,143; 6,432,404; 6,432,402; 6,419,928; 6,413,726; 6,406,694; 6,403,770; 6,403,091; 6,395,276; 6,395,274; 6,387,350; 6,383,759; 6,383,484; 6,376,654; 6,372,215; 6,359,126; 6,355,481; 6,355,444; 6,355,245; 6,355,244; 6,346,246; 6,344,198; 6,340,571; 6,340,459; 6,331,175; 6,306,393; 6,254,868; 6,187,287; 6,183,744; 6,129,914; 6,120,767; 6,096,289; 6,077,499; 5,922,302; 5,874,540; 5,814,440; 5,798,229; 5,789,554; 5,776,456; 5,736,119; 5,716,595; 5,677,136; 5,587,459; 5,443,953, 5,525,338. These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art.

Antibody Allotypes

Immunogenicity of therapeutic antibodies is associated with increased risk of infusion reactions and decreased duration of therapeutic response (Baert et al., 2003, N Engl J Med 348:602-08). The extent to which therapeutic antibodies induce an immune response in the host may be determined in part by the allotype of the antibody (Stickler et al., 2011, Genes and Immunity 12:213-21). Antibody allotype is related to amino acid sequence variations at specific locations in the constant region sequences of the antibody. The allotypes of IgG antibodies containing a heavy chain γ-type constant region are designated as Gm allotypes (1976, J Immunol 117:1056-59).

For the common IgG1 human antibodies, the most prevalent allotype is G1m1 (Stickler et al., 2011, Genes and Immunity 12:213-21). However, the G1m3 allotype also occurs frequently in Caucasians (Stickler et al., 2011). It has been reported that G1m1 antibodies contain allotypic sequences that tend to induce an immune response when administered to non-G1m1 (nG1m1) recipients, such as G1m3 patients (Stickler et al., 2011). Non-G1m1 allotype antibodies are not as immunogenic when administered to G1m1 patients (Stickler et al., 2011).

The human G1m1 allotype comprises the amino acids aspartic acid at Kabat position 356 and leucine at Kabat position 358 in the CH3 sequence of the heavy chain IgG1. The nG1m1 allotype comprises the amino acids glutamic acid at Kabat position 356 and methionine at Kabat position 358. Both G1m1 and nG1m1 allotypes comprise a glutamic acid residue at Kabat position 357 and the allotypes are sometimes referred to as DEL and EEM allotypes. A non-limiting example of the heavy chain constant region sequences for G1m1 and nG1m1 allotype antibodies is shown below for the exemplary antibodies rituximab (SEQ ID NO:7) and veltuzumab (SEQ ID NO:8).

Rituximab heavy chain variable region sequence
(SEQ ID NO: 7)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKAEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Veltuzumab heavy chain variable region
(SEQ ID NO: 8)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK

Jefferis and Lefranc (2009, mAbs 1:1-7) reviewed sequence variations characteristic of IgG allotypes and their effect on immunogenicity. They reported that the G1m3 allotype is characterized by an arginine residue at Kabat position 214, compared to a lysine residue at Kabat 214 in the G1m17 allotype. The nG1m1,2 allotype was characterized by glutamic acid at Kabat position 356, methionine at Kabat position 358 and alanine at Kabat position 431. The G1m1,2 allotype was characterized by aspartic acid at Kabat position 356, leucine at Kabat position 358 and glycine at Kabat position 431. In addition to heavy chain constant region sequence variants, Jefferis and Lefranc (2009) reported allotypic variants in the kappa light chain constant region, with the Km1 allotype characterized by valine at Kabat position 153 and leucine at Kabat position 191, the Km1,2 allotype by alanine at Kabat position 153 and leucine at Kabat position 191, and the Km3 allotype characterized by alanine at Kabat position 153 and valine at Kabat position 191.

With regard to therapeutic antibodies, veltuzumab and rituximab are, respectively, humanized and chimeric IgG1 antibodies against CD20, of use for therapy of a wide variety of hematological malignancies and/or autoimmune diseases. Table 1 compares the allotype sequences of rituximab vs. veltuzumab. As shown in Table 1, rituximab (G1m17,1) is a DEL allotype IgG1, with an additional sequence variation at Kabat position 214 (heavy chain CHI) of lysine in rituximab vs. arginine in veltuzumab. It has been reported that veltuzumab is less immunogenic in subjects than rituximab (see, e.g., Morchhauser et al., 2009, J Clin Oncol 27:3346-53; Goldenberg et al., 2009, Blood 113:1062-70; Robak & Robak, 2011, BioDrugs 25:13-25), an effect that has been attributed to the difference between humanized and chimeric antibodies. However, the difference in allotypes between the EEM and DEL allotypes likely also accounts for the lower immunogenicity of veltuzumab.

TABLE 1

Allotypes of Rituximab vs. Veltuzumab

| | | Heavy chain position and associated allotypes | | | |
|---|---|---|---|---|---|
| | Complete allotype | 214 (allotype) | 356/358 (allotype) | 431 (allotype) | |
| Rituximab | G1m17,1 | K | 17 | D/L | 1 | A | — |
| Veltuzumab | G1m3 | R | 3 | E/M | — | A | — |

In order to reduce the immunogenicity of therapeutic antibodies in individuals of nG1m1 genotype, it is desirable to select the allotype of the antibody to correspond to the G1m3 allotype, characterized by arginine at Kabat 214, and the nG1m1,2 null-allotype, characterized by glutamic acid at Kabat position 356, methionine at Kabat position 358 and alanine at Kabat position 431. Surprisingly, it was found that repeated subcutaneous administration of G1m3 antibodies over a long period of time did not result in a significant immune response. In alternative embodiments, the human IgG4 heavy chain in common with the G1m3 allotype has arginine at Kabat 214, glutamic acid at Kabat 356, methionine at Kabat 359 and alanine at Kabat 431. Since immunogenicity appears to relate at least in part to the residues at those locations, use of the human IgG4 heavy chain constant region sequence for therapeutic antibodies is also a preferred embodiment. Combinations of G1m3 IgG1 antibodies with IgG4 antibodies may also be of use for therapeutic administration.

Nanobodies

Nanobodies are single-domain antibodies of about 12-15 kDa in size (about 110 amino acids in length). Nanobodies can selectively bind to target antigens, like full-size antibodies, and have similar affinities for antigens. However, because of their much smaller size, they may be capable of better penetration into solid tumors. The smaller size also contributes to the stability of the nanobody, which is more resistant to pH and temperature extremes than full size antibodies (Van Der Linden et al., 1999, Biochim Biophys Act 1431:37-46). Single-domain antibodies were originally developed following the discovery that camelids (camels, alpacas, llamas) possess fully functional antibodies without light chains (e.g., Hamsen et al., 2007, Appl Microbiol Biotechnol 77:13-22). The heavy-chain antibodies consist of a single variable domain ($V_{HH}$) and two constant domains ($C_H2$ and $C_H3$). Like antibodies, nanobodies may be developed and used as multivalent and/or bispecific constructs. Humanized forms of nanobodies are in commercial development that are targeted to a variety of target antigens, such as IL-6R, vWF, TNF, RSV, RANKL, IL-17A & F and IgE (e.g., ABLYNX®, Ghent, Belgium), with potential clinical use in cancer and other disorders (e.g., Saerens et al., 2008, Curr Opin Pharmacol 8:600-8; Muyldermans, 2013, Ann Rev Biochem 82:775-97; Ibanez et al., 2011, J Infect Dis 203:1063-72).

The plasma half-life of nanobodies is shorter than that of full-size antibodies, with elimination primarily by the renal route. Because they lack an Fc region, they do not exhibit complement dependent cytotoxicity.

Nanobodies may be produced by immunization of camels, llamas, alpacas or sharks with target antigen, following by isolation of mRNA, cloning into libraries and screening for antigen binding. Nanobody sequences may be humanized by standard techniques (e.g., Jones et al., 1986, Nature 321: 522, Riechmann et al., 1988, Nature 332: 323, Verhoeyen et al., 1988, Science 239: 1534, Carter et al., 1992, Proc. Nat'l Acad. Sci. USA 89: 4285, Sandhu, 1992, Crit. Rev. Biotech. 12: 437, Singer et al., 1993, J. Immun. 150: 2844). Humanization is relatively straight-forward because of the high homology between camelid and human FR sequences.

In various embodiments, the subject ADCs may comprise nanobodies for targeted delivery of conjugated drug to targeted cancer cells. Nanobodies of use are disclosed, for example, in U.S. Pat. Nos. 7,807,162; 7,939,277; 8,188,223; 8,217,140; 8,372,398; 8,557,965; 8,623,361 and 8,629,244, the Examples section of each incorporated herein by reference.)

Antibody Fragments

Antibody fragments are antigen binding portions of an antibody, such as F(ab')$_2$, Fab', F(ab)$_2$, Fab, Fv, sFv, scFv and the like. Antibody fragments which recognize specific epitopes can be generated by known techniques. F(ab')$_2$ fragments, for example, can be produced by pepsin digestion of the antibody molecule. These and other methods are described, for example, by Goldenberg, U.S. Pat. Nos. 4,036,945 and 4,331,647 and references contained therein. Also, see Nisonoff et al., Arch Biochem. Biophys. 89: 230 (1960); Porter, Biochem. J. 73: 119 (1959), Edelman et al., in METHODS IN ENZYMOLOGY VOL. 1, page 422 (Academic Press 1967), and Coligan at pages 2.8.1-2.8.10 and 2.10.-2.10.4. Alternatively, Fab' expression libraries can be constructed (Huse et al., 1989, Science, 246:1274-1281) to allow rapid and easy identification of monoclonal Fab' fragments with the desired specificity.

A single chain Fv molecule (scFv) comprises a VL domain and a VH domain. The VL and VH domains associate to form a target binding site. These two domains are further covalently linked by a peptide linker (L). A scFv molecule is denoted as either VL-L-VH if the VL domain is the N-terminal part of the scFv molecule, or as VH-L-VL if the VH domain is the N-terminal part of the scFv molecule. Methods for making scFv molecules and designing suitable peptide linkers are described in U.S. Pat. No. 4,704,692, U.S. Pat. No. 4,946,778, R. Raag and M. Whitlow, "Single Chain Fvs." FASEB Vol 9:73-80 (1995) and R. E. Bird and B. W. Walker, Single Chain Antibody Variable Regions, TIBTECH, Vol 9: 132-137 (1991).

Other antibody fragments, for example single domain antibody fragments, are known in the art and may be used in the claimed constructs. Single domain antibodies (VHH) may be obtained, for example, from camels, alpacas or llamas by standard immunization techniques. (See, e.g., Muyldermans et al., TIBS 26:230-235, 2001; Yau et al., J Immunol Methods 281:161-75, 2003; Maass et al., J Immunol Methods 324:13-25, 2007). The VHH may have potent antigen-binding capacity and can interact with novel epitopes that are inaccessible to conventional VH-VL pairs. (Muyldermans et al., 2001). Alpaca serum IgG contains about 50% camelid heavy chain only IgG antibodies (HCAbs) (Maass et al., 2007). Alpacas may be immunized with known antigens, such as TNF-α, and VHHs can be isolated that bind to and neutralize the target antigen (Maass et al., 2007). PCR primers that amplify virtually all alpaca VHH coding sequences have been identified and may be used to construct alpaca VHH phage display libraries, which can be used for antibody fragment isolation by standard biopanning techniques well known in the art (Maass et al., 2007).

An antibody fragment can also be prepared by proteolytic hydrolysis of a full-length antibody or by expression in E. coli or another host of the DNA coding for the fragment. An antibody fragment can be obtained by pepsin or papain digestion of full-length antibodies by conventional methods. For example, an antibody fragment can be produced by enzymatic cleavage of antibodies with pepsin to provide an approximate 100 kD fragment denoted F(ab')$_2$. This fragment can be further cleaved using a thiol reducing agent, and optionally a blocking group for the sulfhydryl groups resulting from cleavage of disulfide linkages, to produce an approximate 50 Kd Fab' monovalent fragment. Alternatively, an enzymatic cleavage using papain produces two monovalent Fab fragments and an Fc fragment directly.

Other methods of cleaving antibodies, such as separation of heavy chains to form monovalent light-heavy chain fragments, further cleavage of fragments, or other enzymatic, chemical or genetic techniques may also be used, so long as the fragments bind to the antigen that is recognized by the intact antibody.

Bispecific and Multispecific Antibodies

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. Lancet. 1990; 355:368-371). A preferred bispecific antibody is an anti-CD3×anti-Trop-2 antibody. In alternative embodiments, an anti-CD3 antibody or fragment thereof may be attached to an antibody or fragment against a B-cell associated antigen, such as anti-CD3×anti-CD19, anti-CD3× anti-CD20, anti-CD3×anti-CD22, anti-CD3×anti-HLA-DR or anti-CD3×anti-CD74. In certain embodiments, the techniques and compositions for therapeutic agent conjugation disclosed herein may be used with bispecific or multispecific antibodies as the targeting moieties.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein and Cuello, Nature, 1983; 305:537-540).

Another method for producing bispecific antibodies uses heterobifunctional cross-linkers to chemically tether two different monoclonal antibodies (Staerz, et al. Nature, 1985; 314:628-631; Perez, et al. Nature, 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. Proc Natl Acad Sci USA. 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte, et al. Proc Natl Acad Sci USA. 1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed in U.S. Pat. No. 4,946, 778 and U.S. Pat. No. 5,132,405, the Examples section of each of which is incorporated herein by reference. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,521,056; 7,527,787; 7,534,866; 7,550,143; 7,666,400; 7,858,070; 7,871,622; 7,906,121; 7,906,118; 8,163,291; 7,901,680; 7,981,398; 8,003,111 and 8,034,352, the Examples section of each of which incorporated herein by reference). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods.

Conjugation Protocols

Antibodies or fragments thereof may be conjugated to one or more therapeutic or diagnostic agents. The therapeutic agents do not need to be the same but can be different, e.g. a drug and a radioisotope. For example, $^{131}$I can be incorporated into a tyrosine of an antibody or fusion protein and a drug attached to an epsilon amino group of a lysine residue. Therapeutic and diagnostic agents also can be attached, for example to reduced SH groups and/or to carbohydrate side chains. Many methods for making covalent or non-covalent conjugates of therapeutic or diagnostic agents with antibodies or fusion proteins are known in the art and any such known method may be utilized.

A therapeutic or diagnostic agent can be attached at the hinge region of a reduced antibody component via disulfide bond formation. Alternatively, such agents can be attached using a heterobifunctional cross-linker, such as N-succinyl 3-(2-pyridyldithio)propionate (SPDP). Yu et al., Int. J. Cancer 56: 244 (1994). General techniques for such conjugation are well-known in the art. See, for example, Wong, CHEMISTRY OF PROTEIN CONJUGATION AND CROSS-LINKING (CRC Press 1991); Upeslacis et al., "Modification of Antibodies by Chemical Methods," in MONOCLONAL ANTIBODIES: PRINCIPLES AND APPLICATIONS, Birch et al. (eds.), pages 187-230 (Wiley-Liss, Inc. 1995); Price, "Production and Characterization of Synthetic Peptide-Derived Antibodies," in MONOCLONAL ANTIBODIES: PRODUCTION, ENGINEERING AND CLINICAL APPLICATION, Ritter et al. (eds.), pages 60-84 (Cambridge University Press 1995). Alternatively, the therapeutic or diagnostic agent can be conjugated via a carbohydrate moiety in the Fc region of the antibody. The carbohydrate group can be used to increase the loading of the same agent that is bound to a thiol group, or the carbohydrate moiety can be used to bind a different therapeutic or diagnostic agent.

Methods for conjugating peptides to antibody components via an antibody carbohydrate moiety are well-known to those of skill in the art. See, for example, Shih et al., Int. J. Cancer 41: 832 (1988); Shih et al., Int. J. Cancer 46: 1101 (1990); and Shih et al., U.S. Pat. No. 5,057,313, incorporated herein in their entirety by reference. The general method involves reacting an antibody component having an oxidized carbohydrate portion with a carrier polymer that has at least one free amine function. This reaction results in an initial Schiff base (imine) linkage, which can be stabilized by reduction to a secondary amine to form the final conjugate.

The Fc region may be absent if the antibody used as the antibody component of the immunoconjugate is an antibody fragment. However, it is possible to introduce a carbohydrate moiety into the light chain variable region of a full length antibody or antibody fragment. See, for example, Leung et al., J. Immunol. 154: 5919 (1995); Hansen et al., U.S. Pat. No. 5,443,953 (1995), Leung et al., U.S. Pat. No. 6,254,868, incorporated herein by reference in their entirety. The engineered carbohydrate moiety is used to attach the therapeutic or diagnostic agent.

An alternative method for attaching carrier moieties to a targeting molecule involves use of click chemistry reactions. The click chemistry approach was originally conceived as a method to rapidly generate complex substances by joining small subunits together in a modular fashion. (See, e.g., Kolb et al., 2004, Angew Chem Int Ed 40:3004-31; Evans, 2007, Aust J Chem 60:384-95.) Various forms of click chemistry reaction are known in the art, such as the Huisgen 1,3-dipolar cycloaddition copper catalyzed reaction (Tornoe et al., 2002, J Organic Chem 67:3057-64), which is often referred to as the "click reaction." Other alternatives include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising an azide moiety, the azide reacts with the activated alkyne to form a 1,4-disubstituted 1,2,3-triazole. The copper catalyzed reaction occurs at room temperature and is sufficiently specific that purification of the reaction product is often not required. (Rostovstev et al., 2002, Angew Chem Int Ed 41:2596; Tomoe et al., 2002, J Org Chem 67:3057.) The azide and alkyne functional groups are largely inert towards biomolecules in aqueous medium, allowing the reaction to occur in complex solutions. The triazole formed is chemically stable and is not subject to enzymatic cleavage, making the click chemistry product highly stable in biological systems. Although the copper catalyst is toxic to living cells, the copper-based click chemistry reaction may be used in vitro for immunoconjugate formation.

A copper-free click reaction has been proposed for covalent modification of biomolecules. (See, e.g., Agard et al., 2004, J Am Chem Soc 126:15046-47.) The copper-free reaction uses ring strain in place of the copper catalyst to promote a [3+2] azide-alkyne cycloaddition reaction (Id.) For example, cyclooctyne is an 8-carbon ring structure comprising an internal alkyne bond. The closed ring structure induces a substantial bond angle deformation of the acetylene, which is highly reactive with azide groups to form a triazole. Thus, cyclooctyne derivatives may be used for copper-free click reactions (Id.)

Another type of copper-free click reaction was reported by Ning et al. (2010, Angew Chem Int Ed 49:3065-68), involving strain-promoted alkyne-nitrone cycloaddition. To address the slow rate of the original cyclooctyne reaction, electron-withdrawing groups are attached adjacent to the triple bond (Id.) Examples of such substituted cyclooctynes include difluorinated cyclooctynes, 4-dibenzocyclooctynol and azacyclooctyne (Id.) An alternative copper-free reaction involved strain-promoted alkyne-nitrone cycloaddition to give N-alkylated isoxazolines (Id.) The reaction was reported to have exceptionally fast reaction kinetics and was used in a one-pot three-step protocol for site-specific modification of peptides and proteins (Id.) Nitrones were prepared by the condensation of appropriate aldehydes with N-methylhydroxylamine and the cycloaddition reaction took place in a mixture of acetonitrile and water (Id.) These and other known click chemistry reactions may be used to attach carrier moieties to antibodies in vitro.

Agard et al. (2004, J Am Chem Soc 126:15046-47) demonstrated that a recombinant glycoprotein expressed in CHO cells in the presence of peracetylated N-azidoacetylmannosamine resulted in the bioincorporation of the corresponding N-azidoacetyl sialic acid in the carbohydrates of the glycoprotein. The azido-derivatized glycoprotein reacted specifically with a biotinylated cyclooctyne to form a biotinylated glycoprotein, while control glycoprotein without the azido moiety remained unlabeled (Id.) Laughlin et al. (2008, Science 320:664-667) used a similar technique to metabolically label cell-surface glycans in zebrafish embryos incubated with peracetylated N-azidoacetylgalactosamine. The azido-derivatized glycans reacted with difluorinated cyclooctyne (DIFO) reagents to allow visualization of glycans in vivo.

The Diels-Alder reaction has also been used for in vivo labeling of molecules. Rossin et al. (2010, Angew Chem Int Ed 49:3375-78) reported a 52% yield in vivo between a tumor-localized anti-TAG72 (CC49) antibody carrying a trans-cyclooctene (TCO) reactive moiety and an $^{111}$In-labeled tetrazine DOTA derivative. The TCO-labeled CC49 antibody was administered to mice bearing colon cancer xenografts, followed 1 day later by injection of $^{111}$In-labeled tetrazine probe (Id.) The reaction of radiolabeled probe with tumor localized antibody resulted in pronounced radioactivity localization in the tumor, as demonstrated by SPECT imaging of live mice three hours after injection of radiolabeled probe, with a tumor-to-muscle ratio of 13:1 (Id.) The results confirmed the in vivo chemical reaction of the TCO and tetrazine-labeled molecules.

Alternative methods of chemical conjugation of such moieties to biomolecules are well known in the art, and any such known method may be utilized. General methods of immunoconjugate formation are disclosed, for example, in U.S. Pat. Nos. 4,699,784; 4,824,659; 5,525,338; 5,677,427; 5,697,902; 5,716,595; 6,071,490; 6,187,284; 6,306,393; 6,548,275; 6,653,104; 6,962,702; 7,033,572; 7,147,856; and 7,259,240, the Examples section of each incorporated herein by reference.

The preferred conjugation protocol is based on a thiol-maleimide, a thiol-vinylsulfone, a thiol-bromoacetamide, or a thiol-iodoacetamide reaction that is facile at neutral or acidic pH. This obviates the need for higher pH conditions for conjugations as, for instance, would be necessitated when using active esters. Further details of exemplary conjugation protocols are described below in the Examples section.

Therapeutic Treatment

In another aspect, the invention relates to a method of treating a subject, comprising administering to a subject a therapeutically effective amount of an antibody-drug conjugate (ADC) as described herein. Diseases that may be treated with the ADCs described herein include, but are not limited to B-cell malignancies (e.g., non-Hodgkin's lymphoma, mantle cell lymphoma, multiple myeloma, Hodgkin's lymphoma, diffuse large B cell lymphoma, Burkitt lymphoma, follicular lymphoma, acute lymphocytic leukemia, chronic lymphocytic leukemia, hairy cell leukemia) using, for example an anti-CD22 antibody such as the hLL2 MAb (epratuzumab, see U.S. Pat. No. 6,183,744), against another CD22 epitope (hRFB4) or antibodies against other B cell antigens, such as CD19, CD20, CD21, CD22, CD23, CD37, CD40, CD40L, CD52, CD74, CD80 or HLA-DR. Other diseases include, but are not limited to, adenocarcinomas of endodermally-derived digestive system epithelia, cancers such as breast cancer and non-small cell lung cancer, and other carcinomas, sarcomas, glial tumors, myeloid leukemias, etc. In particular, antibodies against an antigen, e.g., an oncofetal antigen, produced by or associated with a malignant solid tumor or hematopoietic neoplasm, e.g., a gastrointestinal, stomach, colon, esophageal, liver, lung, breast, pancreatic, liver, prostate, ovarian, testicular, brain, bone, urothelial or lymphatic tumor, a sarcoma or a melanoma, are advantageously used. Such therapeutics can be given once or repeatedly, depending on the disease state and tolerability of the conjugate, and can also be used optionally in combination with other therapeutic modalities, such as surgery, external radiation, radioimmunotherapy, immunotherapy, chemotherapy, antisense therapy, interference RNA therapy, gene therapy, and the like. Each combination will be adapted to the tumor type, stage, patient condition and prior therapy, and other factors considered by the managing physician.

As used herein, the term "subject" refers to any animal (i.e., vertebrates and invertebrates) including, but not limited to mammals, including humans. It is not intended that the term be limited to a particular age or sex. Thus, adult and newborn subjects, as well as fetuses, whether male or female, are encompassed by the term. Doses given herein are for humans, but can be adjusted to the size of other mammals, as well as children, in accordance with weight or square meter size.

In a preferred embodiment, therapeutic conjugates comprising an anti-Trop-2 antibody such as the hRS7 MAb can be used to treat carcinomas such as carcinomas of the esophagus, pancreas, lung, stomach, colon and rectum, urinary bladder, breast, ovary, uterus, kidney and prostate, as disclosed in U.S. Pat. Nos. 7,238,785; 7,517,964 and 8,084,583, the Examples section of which is incorporated herein by reference. An hRS7 antibody is a humanized antibody that comprises light chain complementarity-determining region (CDR) sequences CDR1 (KASQDVSIAVA, SEQ ID NO:1); CDR2 (SASYRYT, SEQ ID NO:2); and CDR3 (QQHYITPLT, SEQ ID NO:3) and heavy chain CDR sequences CDR1 (NYGMN, SEQ ID NO:4); CDR2 (WINTYTGEPTYTDDFKG, SEQ ID NO:5) and CDR3 (GGFGSSYWYFDV, SEQ ID NO:6)

In a preferred embodiment, the antibodies that are used in the treatment of human disease are human or humanized (CDR-grafted) versions of antibodies; although murine and chimeric versions of antibodies can be used. Same species IgG molecules as delivery agents are mostly preferred to minimize immune responses. This is particularly important when considering repeat treatments. For humans, a human or humanized IgG antibody is less likely to generate an anti-IgG immune response from patients. Antibodies such as hLL1 and hLL2 rapidly internalize after binding to internalizing antigen on target cells, which means that the chemotherapeutic drug being carried is rapidly internalized into cells as well. However, antibodies that have slower rates of internalization can also be used to effect selective therapy.

In another preferred embodiment, a therapeutic agent used in combination with the camptothecin conjugate of this invention may comprise one or more isotopes. Radioactive isotopes useful for treating diseased tissue include, but are not limited to—$^{111}$In, $^{177}$Lu, $^{212}$Bi, $^{213}$Bi, $^{211}$At, $^{62}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, $^{227}$Th and $^{211}$Pb. The therapeutic radionuclide preferably has a decay-energy in the range of 20 to 6,000 keV, preferably in the ranges 60 to 200 keV for an Auger emitter, 100-2,500 keV for a beta emitter, and 4,000-6,000 keV for an alpha emitter. Maximum decay energies of useful beta-particle-emitting nuclides are preferably 20-5,000 keV, more preferably 100-4,000 keV, and most preferably 500-2,500 keV. Also preferred are radionuclides that substantially decay with Auger-emitting particles. For example, Co-58, Ga-67, Br-80m, Tc-99m, Rh-103m, Pt-109, In-111, Sb-119, I-125, Ho-161, Os-189m and Ir-192. Decay energies of useful beta-particle-emitting nuclides are preferably <1,000 keV, more preferably <100 keV, and most preferably <70 keV. Also preferred are radionuclides that substantially decay with generation of alpha-particles. Such radionuclides include, but are not limited to: Dy-152, At-211, Bi-212, Ra-223, Rn-219, Po-215, Bi-211, Ac-225, Fr-221, At-217, Bi-213, Th-227 and Fm-255. Decay energies of useful alpha-particle-emitting radionuclides are preferably 2,000-10,000 keV, more preferably 3,000-8,000 keV, and most preferably 4,000-7,000 keV. Additional potential radioisotopes of use include $^{11}$C, $^{13}$N, $^{15}$O, $^{75}$Br, $^{198}$Au, $^{224}$Ac, $^{126}$I, $^{133}$I, $^{77}$Br, $^{113m}$In, $^{95}$Ru, $^{97}$Ru, $^{103}$Ru, $^{105}$Ru, $^{107}$Hg, $^{203}$Hg, $^{121m}$Te, $^{122m}$Te, $^{125m}$Te, $^{165}$Tm, $^{167}$Tm, $^{168}$Tm, $^{197}$Pt, $^{109}$Pd, $^{105}$Rh, $^{142}$Pr, $^{143}$Pr, $^{161}$Tb, $^{166}$Ho, $^{199}$Au, $^{57}$Co, $^{58}$Co, $^{51}$Cr, $^{59}$Fe, $^{75}$Se, $^{201}$Tl, $^{225}$Ac, $^{76}$Br, $^{169}$Yb, and the like.

Radionuclides and other metals may be delivered, for example, using chelating groups attached to an antibody or conjugate. Macrocyclic chelates such as NOTA, DOTA, and TETA are of use with a variety of metals and radiometals, most particularly with radionuclides of gallium, yttrium and copper, respectively. Such metal-chelate complexes can be made very stable by tailoring the ring size to the metal of interest. Other ring-type chelates, such as macrocyclic polyethers for complexing $^{223}$Ra, may be used.

Therapeutic agents of use in combination with the camptothecin conjugates described herein also include, for example, chemotherapeutic drugs such as vinca alkaloids, anthracyclines, epipodophyllotoxins, taxanes, antimetabolites, tyrosine kinase inhibitors, alkylating agents, antibiotics, Cox-2 inhibitors, antimitotics, antiangiogenic and proapoptotic agents, particularly doxorubicin, methotrexate, taxol, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in REMINGTON'S PHARMACEUTICAL SCIENCES, 19th Ed. (Mack Publishing Co. 1995), and in GOODMAN AND GILMAN'S THE PHARMACOLOGICAL BASIS OF THERAPEUTICS, 7th Ed. (MacMillan Publishing Co. 1985), as well as revised editions of these publications. Other suitable chemotherapeutic agents, such as experimental drugs, are known to those of skill in the art.

Exemplary drugs of use include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celecoxib, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839. Such agents may be part of the conjugates described herein or may alternatively be administered in combination with the described conjugates, either prior to, simultaneously with or after the conjugate. Alternatively, one or more therapeutic naked antibodies as are known in the art may be used in combination with the described conjugates. Exemplary therapeutic naked antibodies are described above.

In preferred embodiments, a therapeutic agent to be used in combination with a DNA-breaking antibody conjugate (e.g., an SN-38-ADC) is a microtubule inhibitor, such as a vinca alkaloid, a taxanes, a maytansinoid or an auristatin. Exemplary known microtubule inhibitors include paclitaxel, vincristine, vinblastine, mertansine, epothilone, docetaxel, discodermolide, combrestatin, podophyllotoxin, CI-980, phenylahistins, steganacins, curacins, 2-methoxy estradiol, E7010, methoxy benzenesuflonamides, vinorelbine, vinflunine, vindesine, dolastatins, spongistatin, rhizoxin, tasidotin, halichondrins, hemiasterlins, cryptophycin 52, MMAE and eribulin mesylate.

In an alternative preferred embodiment, a therapeutic agent to be used in combination with a DNA-breaking ADC, such as an SN-38-antibody conjugate, is a PARP inhibitor, such as olaparib, talazoparib (BMN-673), rucaparib, veliparib, CEP 9722, MK 4827, BGB-290, ABT-888, AG014699, BSI-201, CEP-8983 or 3-aminobenzamide.

In another alternative, a therapeutic agent used in combination with an antibody or immunoconjugate is a tyrosine kinase inhibitor, such as such as ibrutinib (PCI-32765), PCI-45292, CC-292 (AVL-292), ONO-4059, GDC-0834, LFM-A13 or RN486.

In yet another alternative, a therapeutic agent used in combination with an antibody or immunoconjugate is a PI3K inhibitor, such as idelalisib, Wortmannin, demethoxyviridin, perifosine, PX-866, IPI-145 (duvelisib), BAY 80-6946, BEZ235, RP6530, TGR1202, SF1126, INK1117, GDC-0941, BKM120, XL147, XL765, Palomid 529, GSK1059615, ZSTK474, PWT33597, IC87114, TG100-115, CAL263, PI-103, GNE477, CUDC-907, AEZS-136 or LY294002.

Therapeutic agents that may be used in concert with the camptothecin conjugates also may comprise toxins conjugated to targeting moieties. Toxins that may be used in this regard include ricin, abrin, ribonuclease (RNase), DNase I, ranpirnase, Staphylococcal enterotoxin-A, pokeweed antiviral protein, gelonin, diphtheria toxin, *Pseudomonas* exotoxin, and *Pseudomonas* endotoxin. (See, e.g., Pastan. et al., Cell (1986), 47:641, and Sharkey and Goldenberg, *CA Cancer J Clin*. 2006 July-August; 56(4):226-43.) Additional toxins suitable for use herein are known to those of skill in the art and are disclosed in U.S. Pat. No. 6,077,499.

Yet another class of therapeutic agent may comprise one or more immunomodulators. Immunomodulators of use may be selected from a cytokine, a stem cell growth factor, a lymphotoxin, a hematopoietic factor, a colony stimulating factor (CSF), an interferon (IFN), erythropoietin, thrombopoietin and a combination thereof. Specifically useful are lymphotoxins such as tumor necrosis factor (TNF), hematopoietic factors, such as interleukin (IL), colony stimulating factor, such as granulocyte-colony stimulating factor (G-CSF) or granulocyte macrophage-colony stimulating factor (GM-CSF), interferon, such as interferons-α, -β, -γ or -λ, and stem cell growth factor, such as that designated "S1 factor". Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and —II; erythropoietin (EPO); osteoinductive factors; interferons such as interferon-α, -β, -γ and -λ; colony stimulating factors (CSFs) such as macrophage-CSF (M-CSF); interleukins (ILs) such as IL-1, IL-1α, IL-2, IL-3, IL-4, IL-5, IL-6, IL-7, IL-8, IL-9, IL-10, IL-11, IL-12; IL-β, IL-14, IL-15, IL-16, IL-17, IL-18, IL-21, IL-25, LIF, kit-ligand or FLT-3, angiostatin, thrombospondin, endostatin, tumor necrosis factor and lymphotoxin (LT). As used herein, the term cytokine includes proteins from natural sources or from recombinant cell culture and biologically active equivalents of the native sequence cytokines.

Chemokines of use include RANTES, MCAF, MIP1-alpha, MIP1-Beta and IP-10.

The person of ordinary skill will realize that the subject immunoconjugates, comprising a camptothecin conjugated to an antibody or antibody fragment, may be used alone or in combination with one or more other therapeutic agents, such as a second antibody, second antibody fragment, second immunoconjugate, radionuclide, toxin, drug, chemotherapeutic agent, radiation therapy, chemokine, cytokine, immunomodulator, enzyme, hormone, oligonucleotide, RNAi or siRNA. Such additional therapeutic agents may be administered separately, in combination with, or attached to the subject antibody-drug immunoconjugates.

Formulation and Administration

Suitable routes of administration of the conjugates include, without limitation, oral, parenteral, subcutaneous, rectal, transmucosal, intestinal administration, intramuscular, intramedullary, intrathecal, direct intraventricular, intravenous, intravitreal, intraperitoneal, intranasal, or intraocular injections. The preferred routes of administration are parenteral. Alternatively, one may administer the compound in a local rather than systemic manner, for example, via injection of the compound directly into a solid tumor.

Immunoconjugates can be formulated according to known methods to prepare pharmaceutically useful compositions, whereby the immunoconjugate is combined in a mixture with a pharmaceutically suitable excipient. Sterile phosphate-buffered saline is one example of a pharmaceutically suitable excipient. Other suitable excipients are well-known to those in the art. See, for example, Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

In a preferred embodiment, the immunoconjugate is formulated in Good's biological buffer (pH 6-7), using a buffer selected from the group consisting of N-(2-acetamido)-2-aminoethanesulfonic acid (ACES); N-(2-acetamido)iminodiacetic acid (ADA); N,N-bis(2-hydroxyethyl)-2-aminoethanesulfonic acid (BES); 4-(2-hydroxyethyl)piperazine-1-ethanesulfonic acid (HEPES); 2-(N-morpholino) ethanesulfonic acid (MES); 3-(N-morpholino) propanesulfonic acid (MOPS); 3-(N-morpholinyl)-2-hydroxypropanesulfonic acid (MOPSO); and piperazine-N, N'-bis(2-ethanesulfonic acid) [Pipes]. More preferred buffers are MES or MOPS, preferably in the concentration range of 20 to 100 mM, more preferably about 25 mM. Most preferred is 25 mM MES, pH 6.5. The formulation may further comprise 25 mM trehalose and 0.01% v/v polysorbate 80 as excipients, with the final buffer concentration modified to 22.25 mM as a result of added excipients. The preferred method of storage is as a lyophilized formulation of the conjugates, stored in the temperature range of −20° C. to 2° C., with the most preferred storage at 2° C. to 8° C.

The immunoconjugate can be formulated for intravenous administration via, for example, bolus injection, slow infusion or continuous infusion. Preferably, the antibody of the present invention is infused over a period of less than about 4 hours, and more preferably, over a period of less than about 3 hours. For example, the first 25-50 mg could be infused within 30 minutes, preferably even 15 min, and the remainder infused over the next 2-3 hrs. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents. Alternatively, the active ingredient can be in powder form for constitution with a suitable vehicle, e.g., sterile pyrogen-free water, before use.

Additional pharmaceutical methods may be employed to control the duration of action of the therapeutic conjugate. Control release preparations can be prepared through the use of polymers to complex or adsorb the immunoconjugate. For example, biocompatible polymers include matrices of poly (ethylene-co-vinyl acetate) and matrices of a polyanhydride copolymer of a stearic acid dimer and sebacic acid. Sherwood et al., *Bio/Technology* 10: 1446 (1992). The rate of release of an immunoconjugate from such a matrix depends upon the molecular weight of the immunoconjugate, the amount of immunoconjugate within the matrix, and the size of dispersed particles. Saltzman et al., *Biophys. J.* 55: 163 (1989); Sherwood et al., supra. Other solid dosage forms are described in Ansel et al., PHARMACEUTICAL DOSAGE FORMS AND DRUG DELIVERY SYSTEMS, 5th Edition (Lea & Febiger 1990), and Gennaro (ed.), REMINGTON'S PHARMACEUTICAL SCIENCES, 18th Edition (Mack Publishing Company 1990), and revised editions thereof.

Generally, the dosage of an administered immunoconjugate for humans will vary depending upon such factors as the patient's age, weight, height, sex, general medical condition and previous medical history. It may be desirable to provide the recipient with a dosage of immunoconjugate that is in the range of from about 1 mg/kg to 24 mg/kg as a single intravenous infusion, although a lower or higher dosage also may be administered as circumstances dictate. A dosage of 1-20 mg/kg for a 70 kg patient, for example, is 70-1,400 mg, or 41-824 mg/m$^2$ for a 1.7-m patient. The dosage may be repeated as needed, for example, once per week for 4-10 weeks, once per week for 8 weeks, or once per week for 4 weeks. It may also be given less frequently, such as every other week for several months, or monthly or quarterly for many months, as needed in a maintenance therapy. Preferred dosages may include, but are not limited to, 1 mg/kg, 2 mg/kg, 3 mg/kg, 4 mg/kg, 5 mg/kg, 6 mg/kg, 7 mg/kg, 8 mg/kg, 9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 22 mg/kg and 24 mg/kg. Any amount in the range of 1 to 24 mg/kg may be used. However, in preferred embodiments, the dosage range may be 4 to 16 mg/kg, 6 to 12 mg/kg or 8 to 10 mg/kg.

The dosage is preferably administered multiple times, once or twice a week. A minimum dosage schedule of 4 weeks, more preferably 8 weeks, more preferably 16 weeks or longer may be used. The schedule of administration may comprise administration once or twice a week, on a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five week off; (vi) four weeks of therapy followed by one, two, three, four or five week off; (vii) five weeks of therapy followed by one, two, three, four or five week off; and (viii) monthly. The cycle may be repeated 4, 6, 8, 10, 12, 16 or 20 times or more.

Alternatively, an immunoconjugate may be administered as one dosage every 2 or 3 weeks, repeated for a total of at least 3 dosages. Or, twice per week for 4-6 weeks. If the dosage is lowered to approximately 200-300 mg/m$^2$ (340 mg per dosage for a 1.7-m patient, or 4.9 mg/kg for a 70 kg patient), it may be administered once or even twice weekly for 4 to 10 weeks. Alternatively, the dosage schedule may be decreased, namely every 2 or 3 weeks for 2-3 months. It has been determined, however, that even higher doses, such as 12 mg/kg once weekly or once every 2-3 weeks can be administered by slow i.v. infusion, for repeated dosing cycles. The dosing schedule can optionally be repeated at other intervals and dosage may be given through various parenteral routes, with appropriate adjustment of the dose and schedule.

In preferred embodiments, the immunoconjugates are of use for therapy of cancer. Examples of cancers include, but are not limited to, carcinoma, lymphoma, glioblastoma, melanoma, sarcoma, and leukemia, myeloma, or lymphoid malignancies. More particular examples of such cancers are noted below and include: squamous cell cancer (e.g., epithelial squamous cell cancer), Ewing sarcoma, Wilms tumor, astrocytomas, lung cancer including small-cell lung cancer, non-small cell lung cancer, adenocarcinoma of the lung and squamous carcinoma of the lung, cancer of the peritoneum, gastric or stomach cancer including gastrointestinal cancer, pancreatic cancer, glioblastoma multiforme, cervical cancer, ovarian cancer, liver cancer, bladder cancer, hepatoma, hepatocellular carcinoma, neuroendocrine tumors, medullary thyroid cancer, differentiated thyroid carcinoma, breast cancer, ovarian cancer, colon cancer, rectal cancer, endometrial cancer or uterine carcinoma, salivary gland carcinoma, kidney or renal cancer, prostate cancer, vulvar cancer, anal carcinoma, penile carcinoma, as well as head-and-neck cancer. The term "cancer" includes primary malignant cells or tumors (e.g., those whose cells have not migrated to sites in the subject's body other than the site of the original malignancy or tumor) and secondary malignant cells or tumors (e.g., those arising from metastasis, the migration of malignant cells or tumor cells to secondary sites that are different from the site of the original tumor).

Other examples of cancers or malignancies include, but are not limited to: Acute Childhood Lymphoblastic Leukemia, Acute Lymphoblastic Leukemia, Acute Lymphocytic Leukemia, Acute Myeloid Leukemia, Adrenocortical Carcinoma, Adult (Primary) Hepatocellular Cancer, Adult (Primary) Liver Cancer, Adult Acute Lymphocytic Leukemia, Adult Acute Myeloid Leukemia, Adult Hodgkin's Lymphoma, Adult Lymphocytic Leukemia, Adult Non-Hodgkin's Lymphoma, Adult Primary Liver Cancer, Adult Soft Tissue Sarcoma, AIDS-Related Lymphoma, AIDS-Related Malignancies, Anal Cancer, Astrocytoma, Bile Duct Cancer, Bladder Cancer, Bone Cancer, Brain Stem Glioma, Brain Tumors, Breast Cancer, Cancer of the Renal Pelvis and Ureter, Central Nervous System (Primary) Lymphoma, Central Nervous System Lymphoma, Cerebellar Astrocytoma, Cerebral Astrocytoma, Cervical Cancer, Childhood (Primary) Hepatocellular Cancer, Childhood (Primary) Liver Cancer, Childhood Acute Lymphoblastic Leukemia, Childhood Acute Myeloid Leukemia, Childhood Brain Stem Glioma, Childhood Cerebellar Astrocytoma, Childhood Cerebral Astrocytoma, Childhood Extracranial Germ Cell Tumors, Childhood Hodgkin's Disease, Childhood Hodgkin's Lymphoma, Childhood Hypothalamic and Visual Pathway Glioma, Childhood Lymphoblastic Leukemia, Childhood Medulloblastoma, Childhood Non-Hodgkin's Lymphoma, Childhood Pineal and Supratentorial Primitive Neuroectodermal Tumors, Childhood Primary Liver Cancer, Childhood Rhabdomyosarcoma, Childhood Soft Tissue Sarcoma, Childhood Visual Pathway and Hypothalamic Glioma, Chronic Lymphocytic Leukemia, Chronic Myelogenous Leukemia, Colon Cancer, Cutaneous T-Cell Lymphoma, Endocrine Pancreas Islet Cell Carcinoma, Endometrial Cancer, Ependymoma, Epithelial Cancer, Esophageal Cancer, Ewing's Sarcoma and Related Tumors, Exocrine Pancreatic Cancer, Extracranial Germ Cell Tumor, Extragonadal Germ Cell Tumor, Extrahepatic Bile Duct Cancer, Eye Cancer, Female Breast Cancer, Gaucher's Disease, Gallbladder Cancer, Gastric Cancer, Gastrointestinal Carcinoid Tumor, Gastrointestinal Tumors, Germ Cell Tumors, Gestational Trophoblastic Tumor, Hairy Cell Leukemia, Head and Neck Cancer, Hepatocellular Cancer, Hodgkin's Lymphoma, Hypergammaglobulinemia, Hypopharyngeal Cancer, Intestinal Cancers, Intraocular Melanoma, Islet Cell Carcinoma, Islet Cell Pancreatic Cancer, Kaposi's Sarcoma, Kidney Cancer, Laryngeal Cancer, Lip and Oral Cavity Cancer, Liver Cancer, Lung Cancer, Lymphoproliferative Disorders, Macroglobulinemia, Male Breast Cancer, Malignant Mesothelioma, Malignant Thymoma, Medulloblastoma, Melanoma, Mesothelioma, Metastatic Occult Primary Squamous Neck Cancer, Metastatic Primary Squamous Neck Cancer, Metastatic Squamous Neck Cancer, Multiple Myeloma, Multiple Myeloma/Plasma Cell Neoplasm, Myelodysplastic Syndrome, Myelogenous Leukemia, Myeloid Leukemia, Myeloproliferative Disorders, Nasal Cavity and Paranasal Sinus Cancer, Nasopharyngeal Cancer, Neuroblastoma, Non-Hodgkin's Lymphoma, Nonmelanoma Skin Cancer, Non-Small Cell Lung Cancer, Occult Primary Metastatic Squamous Neck Cancer, Oropharyngeal Cancer, Osteo-/Malignant Fibrous Sarcoma, Osteosarcoma/Malignant Fibrous Histiocytoma, Osteosarcoma/Malignant Fibrous Histiocytoma of Bone, Ovarian Epithelial Cancer, Ovarian Germ Cell Tumor, Ovarian Low Malignant Potential Tumor, Pancreatic Cancer, Paraproteinemias, Polycythemia vera, Parathyroid Cancer, Penile Cancer, Pheochromocytoma, Pituitary Tumor, Primary Central Nervous System Lymphoma, Primary Liver Cancer, Prostate Cancer, Rectal Cancer, Renal Cell Cancer, Renal Pelvis and Ureter Cancer, Retinoblastoma, Rhabdomyosarcoma, Salivary Gland Cancer, Sarcoidosis Sarcomas, Sezary Syndrome, Skin Cancer, Small Cell Lung Cancer, Small Intestine Cancer, Soft Tissue Sarcoma, Squamous Neck Cancer, Stomach Cancer, Supratentorial Primitive Neuroectodermal and Pineal Tumors, T-Cell Lymphoma, Testicular Cancer, Thymoma, Thyroid Cancer, Transitional Cell Cancer of the Renal Pelvis and Ureter, Transitional Renal Pelvis and Ureter Cancer, Trophoblastic Tumors, Ureter and Renal Pelvis Cell Cancer, Urethral Cancer, Uterine Cancer, Uterine Sarcoma, Vaginal Cancer, Visual Pathway and Hypothalamic Glioma, Vulvar Cancer, Waldenström's macroglobulinemia, Wilms' tumor, and any other hyperproliferative disease, besides neoplasia, located in an organ system listed above.

The methods and compositions described and claimed herein may be used to treat malignant or premalignant conditions and to prevent progression to a neoplastic or malignant state, including but not limited to those disorders described above. Such uses are indicated in conditions known or suspected of preceding progression to neoplasia or cancer, in particular, where non-neoplastic cell growth consisting of hyperplasia, metaplasia, or most particularly, dysplasia has occurred (for review of such abnormal growth conditions, see Robbins and Angell, Basic Pathology, 2d Ed., W. B. Saunders Co., Philadelphia, pp. 68-79 (1976)).

Dysplasia is frequently a forerunner of cancer, and is found mainly in the epithelia. It is the most disorderly form of non-neoplastic cell growth, involving a loss in individual cell uniformity and in the architectural orientation of cells. Dysplasia characteristically occurs where there exists chronic irritation or inflammation. Dysplastic disorders which can be treated include, but are not limited to, anhidrotic ectodermal dysplasia, anterofacial dysplasia, asphyxiating thoracic dysplasia, atriodigital dysplasia, bronchopulmonary dysplasia, cerebral dysplasia, cervical dysplasia, chondroectodermal dysplasia, cleidocranial dysplasia, congenital ectodermal dysplasia, craniodiaphysial dysplasia, craniocarpotarsal dysplasia, craniometaphysial dysplasia, dentin dysplasia, diaphysial dysplasia, ectodermal dysplasia, enamel dysplasia, encephalo-ophthalmic dysplasia, dysplasia epiphysialis hemimelia, dysplasia epiphysialis multiplex, dysplasia epiphysialis punctata, epithelial dysplasia, faciodigitogenital dysplasia, familial fibrous dysplasia of jaws, familial white folded dysplasia, fibromuscular dysplasia, fibrous dysplasia of bone, florid osseous dysplasia, hereditary renal-retinal dysplasia, hidrotic ectodermal dysplasia, hypohidrotic ectodermal dysplasia, lymphopenic thymic dysplasia, mammary dysplasia, mandibulofacial dysplasia, metaphysial dysplasia, Mondini dysplasia, monostotic fibrous dysplasia, mucoepithelial dysplasia, multiple epiphysial dysplasia, oculoauriculovertebral dysplasia, oculodentodigital dysplasia, oculovertebral dysplasia, odontogenic dysplasia, opthalmomandibulomelic dysplasia, periapical cemental dysplasia, polyostotic fibrous dysplasia, pseudoachondroplastic spondyloepiphysial dysplasia, retinal dysplasia, septo-optic dysplasia, spondyloepiphysial dysplasia, and ventriculoradial dysplasia.

Additional pre-neoplastic disorders which can be treated include, but are not limited to, benign dysproliferative disorders (e.g., benign tumors, fibrocystic conditions, tissue hypertrophy, intestinal polyps or adenomas, and esophageal dysplasia), leukoplakia, keratoses, Bowen's disease, Farmer's Skin, solar cheilitis, and solar keratosis. In preferred embodiments, the method of the invention is used to inhibit growth, progression, and/or metastasis of cancers, in particular those listed above.

Additional hyperproliferative diseases, disorders, and/or conditions include, but are not limited to, progression, and/or metastases of malignancies and related disorders such as leukemia (including acute leukemias; e.g., acute lymphocytic leukemia, acute myelocytic leukemia [including myeloblastic, promyelocytic, myelomonocytic, monocytic, and erythroleukemia]) and chronic leukemias (e.g., chronic myelocytic [granulocytic] leukemia and chronic lymphocytic leukemia), polycythemia vera, lymphomas (e.g., Hodgkin's disease and non-Hodgkin's disease), multiple myeloma, Waldenström's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, emangioblastoma, acoustic neuroma, oligodendroglioma, meningioma, melanoma, neuroblastoma, and retinoblastoma.

Autoimmune diseases that may be treated with immunoconjugates may include acute and chronic immune thrombocytopenias, dermatomyositis, Sydenham's chorea, myasthenia gravis, systemic lupus erythematosus, lupus nephritis, rheumatic fever, polyglandular syndromes, bullous pemphigoid, diabetes mellitus, Henoch-Schonlein purpura, poststreptococcal nephritis, erythema nodosum, Takayasu's arteritis, ANCA-associated vasculitides, Addison's disease, rheumatoid arthritis, multiple sclerosis, sarcoidosis, ulcerative colitis, erythema multiforme, IgA nephropathy, polyarteritis nodosa, ankylosing spondylitis, Goodpasture's syndrome, thromboangitis obliterans, Sjogren's syndrome, primary biliary cirrhosis, Hashimoto's thyroiditis, thyrotoxicosis, scleroderma, chronic active hepatitis, polymyositis/dermatomyositis, polychondritis, bullous pemphigoid, pemphigus vulgaris, Wegener's granulomatosis, membranous nephropathy, amyotrophic lateral sclerosis, tabes dorsalis, giant cell arteritis/polymyalgia, pernicious anemia, rapidly progressive glomerulonephritis, psoriasis or fibrosing alveolitis.

Kits

Various embodiments may concern kits containing components suitable for treating cancer in a patient. Exemplary kits may contain at least one drug-conjugated antibody as described herein. If the composition containing components for administration is not formulated for delivery via the alimentary canal, such as by oral delivery, a device capable of delivering the kit components through some other route may be included. One type of device, for applications such as parenteral delivery, is a syringe that is used to inject the composition into the body of a subject. Inhalation devices may also be used.

The kit components may be packaged together or separated into two or more containers. In some embodiments, the containers may be vials that contain sterile, lyophilized formulations of a composition that are suitable for reconstitution. A kit may also contain one or more buffers suitable for reconstitution and/or dilution of other reagents. Other containers that may be used include, but are not limited to, a pouch, tray, box, tube, or the like. Kit components may be packaged and maintained sterilely within the containers. Another component that can be included is instructions to a person using a kit for its use.

EXAMPLES

The examples below are illustrative of embodiments of the current invention and are not limiting to the scope of the claims.

Example 1. Targeted Therapy of GI Cancers with IMMU-132 (Sacituzumab Govitecan), an Anti-Trop-2-SN-38 Antibody Drug Conjugate (ADC)

Trop-2 is a tumor-associated glycoprotein highly prevalent in many epithelial cancers. Its elevated expression has been linked to more aggressive disease and a poor prognosis. A humanized mAb binding to the extracellular domain of Trop-2 was conjugated to SN-38 (IMMU-132; average drug:mAb ratio=7.6), the active principle of CPT-11. After potent activity in human tumor xenografts, a Phase I/II trial was initiated in patients (pts) with diverse solid tumors, including GI cancers.

Methods:

Patients with metastatic cancers were enrolled after failing standard therapy, starting at a dose of 8.0 mg/kg given on days 1 and 8 of a 3-week cycle. The MTD was determined to be 12 mg/kg; dose levels of 8 and 10 mg/kg were chosen for Phase II testing.

Results:

Sixty patients with advanced GI cancers were enrolled in a Phase I/II trial. In 29 CRC patients (9 treated at 10 mg/kg, 20 at 8 mg/kg), 1 had a PR (partial response) and 14 had SD (stable disease) as the best response by RECIST, with a time to progression (TTP) of 50+ wks for the PR (−65%) and a median of 21+ wks for the SD patients (5 continuing). Thirteen CRC patients had KRAS mutations, 7 showing SD with a median TTP of 19.1+ wks (range, 12.0-34.0; 3 continuing). Of 15 pancreatic cancer patients that were treated (5 at 8, 7 at 10, and 3 at 12 mg/kg), 7 had SD as best response for a median TTP of 15.0 wks. Among 11 patients with esophageal cancer (9 started at 8, 1 at 10, and 1 at 18 mg/kg), 8 had CT assessment, showing 1 PR with a TTP of 30+ wks, and 4 with SD of 17.4+, 21.9, 26.3, and 29.9 wks. Of 5 gastric cancer patients (2 at 8 and 3 at 10 mg/kg), only 3 have had CT assessment, all with SD (1 with 19% target lesion reduction and an ongoing TTP of 29+ wks).

Neutropenia was the principal dose-limiting toxicity, with fatigue, diarrhea, nausea, and vomiting as other commonly reported toxicities. However, the toxicity profile from 75 patients in the full trial showed only 17.3% and 2.7% Grade 3 and Grade 4 neutropenia, respectively, and just 6.7% Grade 3 diarrhea.

Conclusions:

IMMU-132 showed a high therapeutic index in patients with diverse relapsed metastatic GI cancers. It has a moderately-toxic drug conjugated to an internalizing, cancer-selective mAb, which can be given repeatedly over many months once weekly×2 in a 21-day cycle.

Example 2. Production and Use of Anti-Trop-2-SN-38 Antibody-Drug Conjugate

The humanized RS7 (hRS7) anti-Trop-2 antibody was produced as described in U.S. Pat. No. 7,238,785, the Figures and Examples section of which are incorporated herein by reference. SN-38 attached to a CL2A linker was produced and conjugated to hRS7 (anti-Trop-2), hPAM4 (anti-MUC5ac), hA20 (anti-CD20) or hMN-14 (anti-CEACAM5) antibodies according to U.S. Pat. No. 7,999,083 (Example 10 and 12 of which are incorporated herein by reference). The conjugation protocol resulted in a ratio of about 6 SN-38 molecules attached per antibody molecule.

Figure 2:
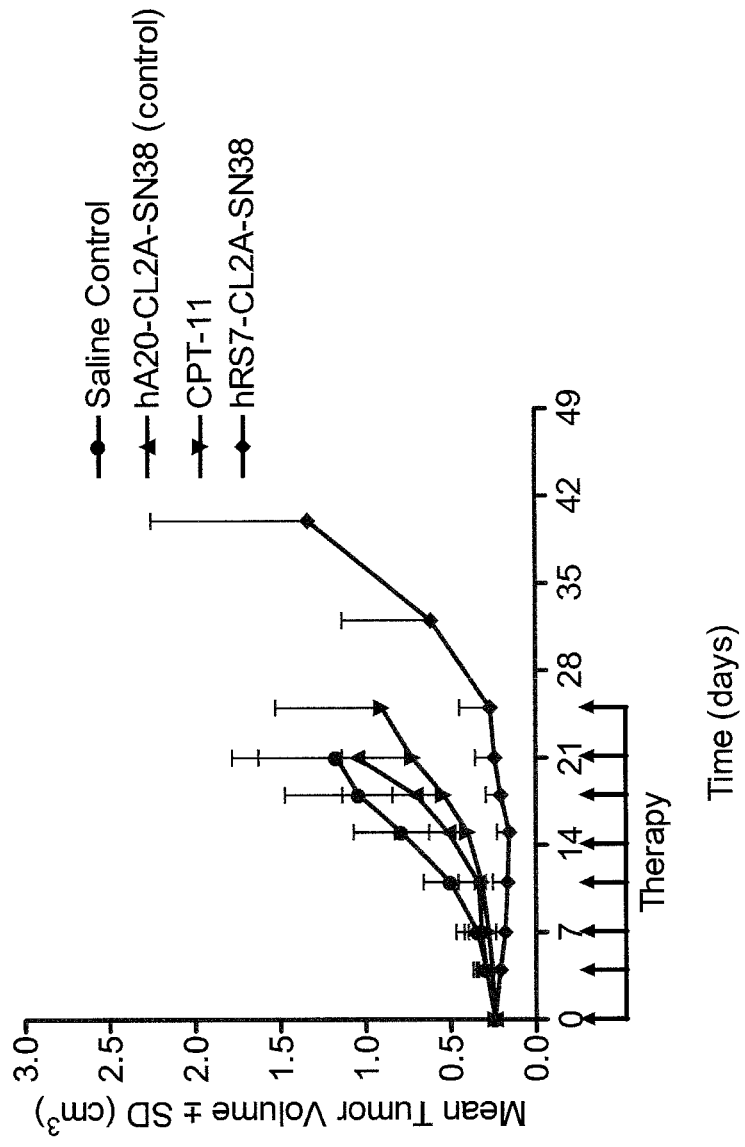
FIG. 2. Preclinical in vivo therapy of athymic nude mice, bearing BxPC3 human pancreatic carcinoma, with anti-TROP2-CL2A-SN-38 conjugates compared to controls.

Immune-compromised athymic nude mice (female), bearing subcutaneous human pancreatic or colon tumor xenografts were treated with either specific CL2A-SN-38 conjugate or control conjugate or were left untreated. The therapeutic efficacies of the specific conjugates were observed. FIG. 1 shows a Capan 1 pancreatic tumor model, wherein specific CL2A-SN-38 conjugates of hRS7 (anti-Trop-2), hPAM4 (anti-MUC-5ac), and hMN-14 (anti-CEACAM5) antibodies showed better efficacies than control hA20-CL2A-SN-38 conjugate (anti-CD20) and untreated control. Similarly in a BXPC3 model of human pancreatic cancer, the specific hRS7-CL2A-SN-38 showed better therapeutic efficacy than control treatments (FIG. 2).

Example 3. Efficacy of Anti-Trop-2-SN-38 ADC Against Diverse Epithelial Cancers In Vivo Abstract The purpose of this study was to evaluate the efficacy of an SN-38-anti-Trop-2 (hRS7) ADC against several human solid tumor types, and to assess its tolerability in mice and monkeys, the latter with tissue cross-reactivity to hRS7 similar to humans. Two SN-3 8 derivatives, CL2-SN-38 and CL2A-SN-38, were conjugated to the anti-Trop-2-humanized antibody, hRS7. The immunoconjugates were characterized in vitro for stability, binding, and cytotoxicity. Efficacy was tested in five different human solid tumor-xenograft models that expressed Trop-2 antigen. Toxicity was assessed in mice and in Cynomolgus monkeys.

The hRS7 conjugates of the two SN-38 derivatives were equivalent in drug substitution (~6), cell binding ($K_d$~1.2 nmol/L), cytotoxicity ($IC_{50}$~2.2 nmol/L), and serum stability in vitro ($t_{1/2}$~20 hours). Exposure of cells to the ADC demonstrated signaling pathways leading to PARP cleavage, but differences versus free SN-38 in p53 and p21 upregulation were noted. Significant antitumor effects were produced by hRS7-SN-38 at nontoxic doses in mice bearing Calu-3 (P≤0.05), Capan-1 (P<0.018), BxPC-3 (P<0.005), and COLO 205 tumors (P<0.033) when compared to non-targeting control ADCs. Mice tolerated a dose of 2×12 mg/kg (SN-38 equivalents) with only short-lived elevations in ALT and AST liver enzyme levels. Cynomolgus monkeys infused with 2×0.96 mg/kg exhibited only transient decreases in blood counts, although, importantly, the values did not fall below normal ranges.

In summary, the anti-Trop-2 hRS7-CL2A-SN-38 ADC provided significant and specific antitumor effects against a range of human solid tumor types. It was well tolerated in monkeys, with tissue Trop-2 expression similar to humans, at clinically relevant doses.

Introduction

Successful irinotecan treatment of patients with solid tumors has been limited, due in large part to the low conversion rate of the CPT-11 prodrug into the active SN-38 metabolite. Others have examined nontargeted forms of SN-38 as a means to bypass the need for this conversion and to deliver SN-38 passively to tumors. We conjugated SN-38 covalently to a humanized anti-Trop-2 antibody, hRS7. This antibody-drug conjugate has specific antitumor effects in a range of s.c. human cancer xenograft models, including non-small cell lung carcinoma, pancreatic, colorectal, and squamous cell lung carcinomas, all at nontoxic doses (e.g., <3.2 mg/kg cumulative SN-38 equivalent dose). Trop-2 is widely expressed in many epithelial cancers, but also some normal tissues, and therefore a dose escalation study in Cynomolgus monkeys was performed to assess the clinical safety of this conjugate. Monkeys tolerated 24 mg SN-38 equivalents/kg with only minor, reversible, toxicities. Given its tumor-targeting and safety profile, hRS7-SN-38 provides a significant improvement in the management of solid tumors responsive to irinotecan.

Material and Methods

Cell Lines, Antibodies, and Chemotherapeutics—

All human cancer cell lines used in this study were purchased from the American Type Culture Collection. These include Calu-3 (non-small cell lung carcinoma), SK-MES-1 (squamous cell lung carcinoma), COLO 205 (colonic adenocarcinoma), Capan-1 and BxPC-3 (pancreatic adenocarcinomas), and PC-3 (prostatic adenocarcinomas). Humanized RS7 IgG and control humanized anti-CD20 (hA20 IgG, veltuzumab) and anti-CD22 (hLL2 IgG, epratuzumab) antibodies were prepared at Immunomedics, Inc. Irinotecan (20 mg/mL) was obtained from Hospira, Inc.

SN-38 Immunoconjugates and In Vitro Aspects—

Synthesis of CL2-SN-38 has been described previously (Moon et al., 2008, J Med Chem 51:6916-26). Its conjugation to hRS7 IgG and serum stability were performed as described (Moon et al., 2008, J Med Chem 51:6916-26; Govindan et al., 2009, Clin Chem Res 15:6052-61). Preparations of CL2A-SN-38 (M.W. 1480) and its hRS7 conjugate, and stability, binding, and cytotoxicity studies, were conducted as described in the preceding Examples.

In Vivo Therapeutic Studies—

For all animal studies, the doses of SN-38 immunoconjugates and irinotecan are shown in SN-38 equivalents. Based on a mean SN-38/IgG substitution ratio of 6, a dose of 500 µg ADC to a 20-g mouse (25 mg/kg) contains 0.4 mg/kg of SN-38. Irinotecan doses are likewise shown as SN-38 equivalents (i.e., 40 mg irinotecan/kg is equivalent to 24 mg/kg of SN-38).

NCr female athymic nude (nu/nu) mice, 4 to 8 weeks old, and male Swiss-Webster mice, 10 weeks old, were purchased from Taconic Farms. Tolerability studies were performed in Cynomolgus monkeys (Macaca fascicularis; 2.5-4 kg male and female) by SNBL USA, Ltd.

Animals were implanted subcutaneously with different human cancer cell lines. Tumor volume (TV) was determined by measurements in 2 dimensions using calipers, with volumes defined as: $L \times w^2/2$, where L is the longest dimension of the tumor and w is the shortest. Tumors ranged in size between 0.10 and 0.47 cm$^3$ when therapy began. Treatment regimens, dosages, and number of animals in each experiment are described in the Results. The lyophilized hRS7-CL2A-SN-38 and control ADC were reconstituted and diluted as required in sterile saline. All reagents were administered intraperitoneally (0.1 mL), except irinotecan, which was administered intravenously. The dosing regimen was influenced by our prior investigations, where the ADC was given every 4 days or twice weekly for varying lengths of time (Moon et al., 2008, J Med Chem 51:6916-26; Govindan et al., 2009, Clin Chem Res 15:6052-61). This dosing frequency reflected a consideration of the conjugate's serum half-life in vitro, to allow a more continuous exposure to the ADC.

Statistics—

Growth curves are shown as percent change in initial TV over time. Statistical analysis of tumor growth was based on area under the curve (AUC). Profiles of individual tumor growth were obtained through linear-curve modeling. An f-test was employed to determine equality of variance between groups before statistical analysis of growth curves. A 2-tailed t-test was used to assess statistical significance between the various treatment groups and controls, except for the saline control, where a 1-tailed t-test was used (significance at P≤0.05). Statistical comparisons of AUC were performed only up to the time that the first animal within a group was euthanized due to progression.

Pharmacokinetics and Biodistribution—

$^{111}$In-radiolabeled hRS7-CL2A-SN-38 and hRS7 IgG were injected into nude mice bearing s.c. SK-MES-1 tumors (~0.3 cm$^3$). One group was injected intravenously with 20 µCi (250-µg protein) of $^{111}$In-hRS7-CL2A-SN-38, whereas another group received 20 µCi (250-µg protein) of $^{111}$In-hRS7 IgG. At various timepoints mice (5 per timepoint) were anesthetized, bled via intracardiac puncture, and then euthanized. Tumors and various tissues were removed, weighed, and counted by γ scintillation to determine the percentage injected dose per gram tissue (% ID/g). A third group was injected with 250 µg of unlabeled hRS7-CL2A-SN-38 3 days before the administration of $^{111}$In-hRS7-CL2A-SN-38 and likewise necropsied. A 2-tailed t-test was used to compare hRS7-CL2A-SN-38 and hRS7 IgG uptake after determining equality of variance using the f-test. Pharmacokinetic analysis on blood clearance was performed using WinNonLin software (Parsight Corp.).

Tolerability in Swiss-Webster Mice and Cynomolgus Monkeys—

Briefly, mice were sorted into 4 groups each to receive 2-mL i.p. injections of either a sodium acetate buffer control or 3 different doses of hRS7-CL2A-SN-38 (4, 8, or 12 mg/kg of SN-38) on days 0 and 3 followed by blood and serum collection, as described in Results. Cynomolgus monkeys (3 male and 3 female; 2.5-4.0 kg) were administered 2 different doses of hRS7-CL2A-SN-38. Dosages, times, and number of monkeys bled for evaluation of possible hematologic toxicities and serum chemistries are described in the Results.

Results

Stability and Potency of hRS7-CL2A-SN-38—

Figure 3A:
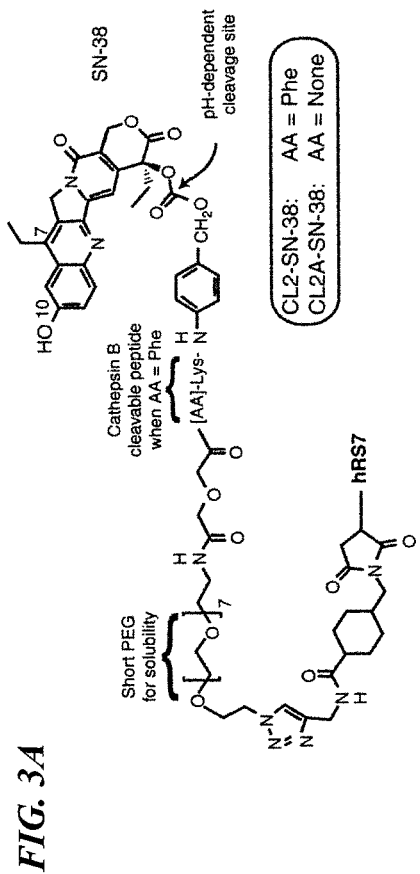
FIG. 3A. Structures of CL2-SN-38 and CL2A-SN-38.

Two different linkages were used to conjugate SN-38 to hRS7 IgG (FIG. 3A). The first is termed CL2-SN-38 and has been described previously (Moon et al., 2008, J Med Chem 51:6916-26; Govindan et al., 2009, Clin Chem Res 15:6052-61). A change in the synthesis of CL2 to remove the phenylalanine moiety within the linker was used to produce the CL2A linker. This change simplified the synthesis, but did not affect the conjugation outcome (e.g., both CL2-SN-38 and CL2A-SN-38 incorporated ~6 SN-38 per IgG molecule). Side-by-side comparisons found no significant differences in serum stability, antigen binding, or in vitro cytotoxicity. This result was surprising, since the phenylalanine residue in CL2 is part of a designed cleavage site for cathepsin B, a lysosomal protease.

Figure 3B:
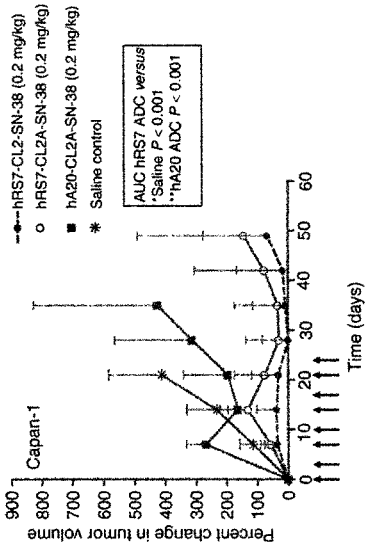
FIG. 3B. Comparative efficacy of anti-Trop-2 ADC linked to CL2 vs. CL2A linkers versus hA20 ADC and saline control, using COLO 205 colonic adenocarcinoma. Animals were treated twice weekly for 4 weeks as indicated by the arrows. COLO 205 mice (N=6) were treated with 0.4 mg/kg ADC and tumors measured twice a week.
Figure 3C:
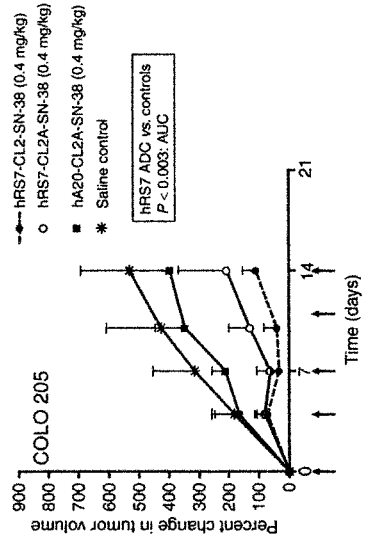
FIG. 3C. Comparative efficacy of anti-Trop-2 ADC linked to CL2 vs. CL2A linkers versus hA20 ADC and saline control, using Capan-1 pancreatic adenocarcinoma. Animals were treated twice weekly for 4 weeks as indicated by the arrows. Capan-1 mice (N=10) were treated with 0.2 mg/kg ADC and tumors measured weekly.

To confirm that the change in the SN-38 linker from CL2 to CL2A did not impact in vivo potency, hRS7-CL2A and hRS7-CL2-SN-38 were compared in mice bearing COLO 205 (FIG. 3B) or Capan-1 tumors (FIG. 3C), using 0.4 mg or 0.2 mg/kg SN-38 twice weekly×4 weeks, respectively, and with starting tumors of 0.25 cm$^3$ size in both studies. Both the hRS7-CL2A and CL2-SN-38 conjugates significantly inhibited tumor growth compared to untreated ($AUC_{14days}$P<0.002 vs. saline in COLO 205 model; $AUC_{21days}$ P<0.001 vs. saline in Capan-1 model), and a nontargeting anti-CD20 control ADC, hA20-CL2A-SN-38 ($AUC_{14days}$ P<0.003 in COLO-205 model; $AUC_{35days}$: P<0.002 in Capan-1 model). At the end of the study (day 140) in the Capan-1 model, 50% of the mice treated with hRS7-CL2A-SN-38 and 40% of the hRS7-CL2-SN-38 mice were tumor-free, whereas only 20% of the hA20-ADC-treated animals had no visible sign of disease. As demonstrated in FIG. 3, the CL2A linker resulted in a somewhat higher efficacy compared to CL2.

Mechanism of Action—

In vitro cytotoxicity studies demonstrated that hRS7-CL2A-SN-38 had $IC_{50}$ values in the nmol/L range against several different solid tumor lines (Table 2). The $IC_{50}$ with free SN-38 was lower than the conjugate in all cell lines. Although there was no apparent correlation between Trop-2 expression and sensitivity to hRS7-CL2A-SN-38, the $IC_{50}$ ratio of the ADC versus free SN-3 8 was lower in the higher Trop-2-expressing cells, most likely reflecting the enhanced ability to internalize the drug when more antigen is present.

SN-38 is known to activate several signaling pathways in cells, leading to apoptosis (e.g., Cusack et al., 2001, Cancer Res 61:3535-40; Liu et al. 2009, Cancer Lett 274:47-53; Lagadec et al., 2008, Br J Cancer 98:335-44). Our initial studies examined the expression of 2 proteins involved in early signaling events (p21$^{Waf1/Cip1}$ and p53) and 1 late apoptotic event [cleavage of poly-ADP-ribose polymerase (PARP)] in vitro (not shown). In BxPC-3, SN-38 led to a 20-fold increase in p21$^{Waf1/Cip1}$ expression (not shown), whereas hRS7-CL2A-SN-38 resulted in only a 10-fold increase (not shown), a finding consistent with the higher activity with free SN-38 in this cell line (Table 2). However, hRS7-CL2A-SN-38 increased p21$^{Waf1/Cip1}$ expression in Calu-3 more than 2-fold over free SN-38 (not shown).

A greater disparity between hRS7-CL2A-SN-38- and free SN-38-mediated signaling events was observed in p53 expression (not shown). In both BxPC-3 and Calu-3, upregulation of p53 with free SN-38 was not evident until 48 hours, whereas hRS7-CL2A-SN-38 upregulated p53 within 24 hours (not shown). In addition, p53 expression in cells exposed to the ADC was higher in both cell lines compared to SN-38 (not shown). Interestingly, although hRS7 IgG had no appreciable effect on p21$^{Waf1/Cip1}$ expression, it did induce the upregulation of p53 in both BxPC-3 and Calu-3, but only after a 48-hour exposure (not shown). In terms of later apoptotic events, cleavage of PARP was evident in both cell lines when incubated with either SN-38 or the conjugate (not shown). The presence of the cleaved PARP was higher at 24 hours in BxPC-3 (not shown), which correlates with high expression of p21 and its lower $IC_{50}$. The higher degree of cleavage with free SN-38 over the ADC was consistent with the cytotoxicity findings.

Efficacy of hRS7-SN-38—

Figure 4A:
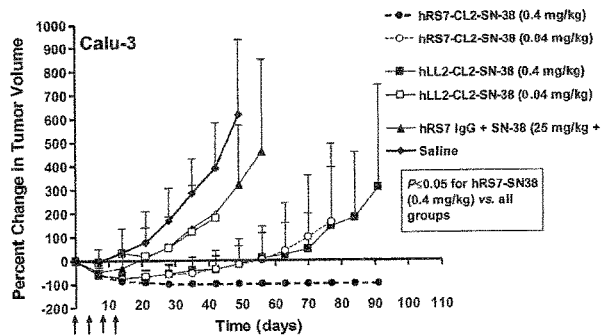
FIG. 4A. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). Mice bearing Calu-3 tumors (N=5-7) were injected with hRS7-CL2-SN-38 every 4 days for a total of 4 injections (q4dx4).

Because Trop-2 is widely expressed in several human carcinomas, studies were performed in several different human cancer models, which started using the hRS7-CL2-SN-38 linkage, but later, conjugates with the CL2A-linkage were used. Calu-3-bearing nude mice given 0.04 mg SN-38/kg of the hRS7-CL2-SN-38 every 4 days×4 had a significantly improved response compared to animals administered the equivalent amount of non-targeting hLL2-CL2-SN-38 (TV=0.14±0.22 cm$^3$ vs. 0.80+0.91 cm$^3$, respectively; $AUC_{42days}$ P<0.026; FIG. 4A). A dose-response was observed when the dose was increased to 0.4 mg/kg SN-38 (FIG. 4A). At this higher dose level, all mice given the specific hRS7 conjugate were "cured" within 28 days, and remained tumor-free until the end of the study on day 147, whereas tumors regrew in animals treated with the irrelevant ADC (specific vs. irrelevant $AUC_{98days}$: P=0.05). In mice receiving the mixture of hRS7 IgG and SN-38, tumors progressed >4.5-fold by day 56 (TV=1.10±0.88 cm$^3$; $AUC_{56days}$ P<0.006 vs. hRS7-CL2-SN-38) (FIG. 4A).

Figure 4B:
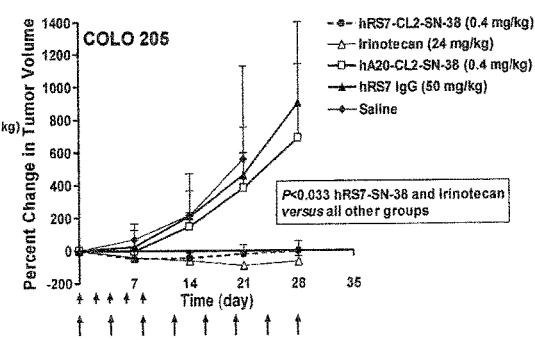
FIG. 4B. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). COLO 205 tumor-bearing mice (N=5) were injected 8 times (q4dx8) with the ADC or every 2 days for a total of 5 injections (q2dx5) with the MTD of irinotecan.

Efficacy also was examined in human colonic (COLO 205) and pancreatic (Capan-1) tumor xenografts. In COLO 205 tumor-bearing animals, (FIG. 4B http://clincancerres.aacrioumals.org/content/17/10/3157.long—F3), hRS7-CL2-SN-38 (0.4 mg/kg, q4dx8) prevented tumor growth over the 28-day treatment period with significantly smaller tumors compared to control anti-CD20 ADC (hA20-CL2-SN-38), or hRS7 IgG (TV=0.16±0.09 cm$^3$, 1.19±0.59 cm$^3$, and 1.77±0.93 cm$^3$, respectively; $AUC_{28days}$ P<0.016).

TABLE 2

Expression of Trop-2 in vitro cytotoxicity of SN-38 and hRS7-SN-38 in various solid tumor lines

| | Trop-2 expression via FACS | | Cytotoxicity results | | | | |
|---|---|---|---|---|---|---|---|
| | | | SN-38 | 95% CI | hRS7-SN-38 | 95% CI | |
| Cell line | Median fluorescence (background) | Percent positive | $IC_{50}$ (nmol/L) | $IC_{50}$ (nmol/L) | $IC_{50}$ (nmol/L) | $IC_{50}$ (nmol/L) | ADC/free SN-38 ratio |
| Calu-3 | 282.2 (4.7) | 99.6% | 7.19 | 5.77-8.95 | 9.97 | 8.12-12.25 | 1.39 |
| COLO 205 | 141.5 (4.5) | 99.5% | 1.02 | 0.66-1.57 | 1.95 | 1.26-3.01 | 1.91 |
| Capan-1 | 100.0 (5.0) | 94.2% | 3.50 | 2.17-5.65 | 6.99 | 5.02-9.72 | 2.00 |
| PC-3 | 46.2 (5.5) | 73.6% | 1.86 | 1.16-2.99 | 4.24 | 2.99-6.01 | 2.28 |
| SK-MES-1 | 44.0 (3.5) | 91.2% | 8.61 | 6.30-11.76 | 23.14 | 17.98-29.78 | 2.69 |
| BxPC-3 | 26.4 (3.1) | 98.3% | 1.44 | 1.04-2.00 | 4.03 | 3.25-4.98 | 2.80 |

The MTD of irinotecan (24 mg SN-38/kg, q2dx5) was as effective as hRS7-CL2-SN-38 in COLO 205 cells, because mouse serum can more efficiently convert irinotecan to SN-38 (Morton et al., 2000, Cancer Res 60:4206-10) than human serum, but the SN-38 dose in irinotecan (2,400 μg cumulative) was 37.5-fold greater than with the conjugate (64 μg total).

Figure 4C:
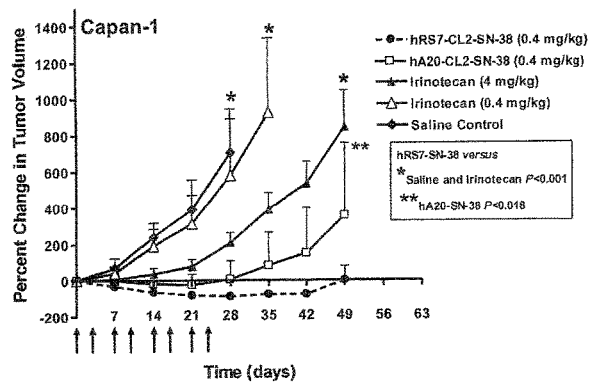
FIG. 4C. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). Capan-1 (N=10) were treated twice weekly for 4 weeks with the agents indicated.

Animals bearing Capan-1 (FIG. 4C) showed no significant response to irinotecan alone when given at an SN-38-dose equivalent to the hRS7-CL2-SN-38 conjugate (e.g., on day 35, average tumor size was 0.04±0.05 cm$^3$ in animals given 0.4 mg SN-38/kg hRS7-SN-38 vs. 1.78±0.62 cm$^3$ in irinotecan-treated animals given 0.4 mg/kg SN-38; $AUC_{day35}$ P<0.001; FIG. 4C). When the irinotecan dose was increased 10-fold to 4 mg/kg SN-38, the response improved, but still was not as significant as the conjugate at the 0.4 mg/kg SN-38 dose level (TV=0.17±0.18 cm$^3$ vs. 1.69±0.47 cm$^3$, $AUC_{day49}$ P<0.001) (FIG. 4C). An equal dose of nontargeting hA20-CL2-SN-38 also had a significant antitumor effect as compared to irinotecan-treated animals, but the specific hRS7 conjugate was significantly better than the irrelevant ADC (TV=0.17+0.18 cm$^3$ vs. 0.80±0.68 cm$^3$, $AUC_{day49}$ P<0.018) (FIG. 4C).

Figure 4D:
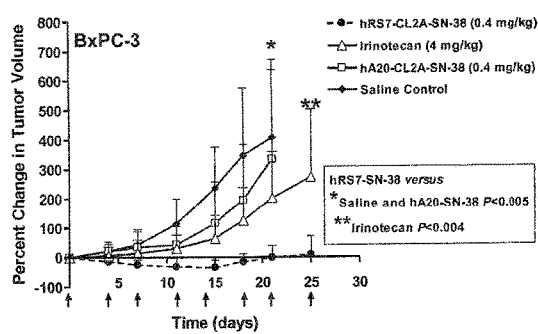
FIG. 4D. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). BxPC-3 tumor-bearing mice (N=10) were treated twice weekly for 4 weeks with the agents indicated.
Figure 4E:
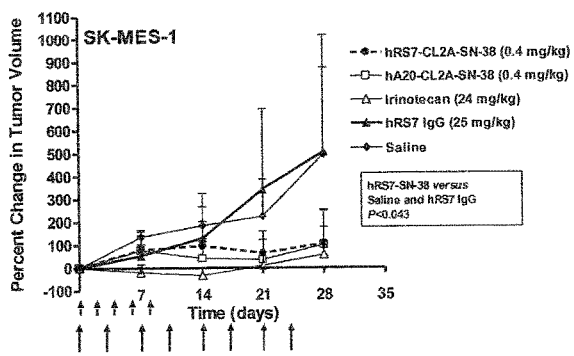
FIG. 4E. Therapeutic efficacy of hRS7-SN-38 ADC in several solid tumor-xenograft disease models. Efficacy of hRS7-CL2-SN-38 and hRS7-CL2A-SN-38 ADC treatment was studied in mice bearing human non-small cell lung, colorectal, pancreatic, or squamous cell lung tumor xenografts. All the ADCs and controls were administered in the amounts indicated (expressed as amount of SN-38 per dose; long arrows=conjugate injections, short arrows=irinotecan injections). In addition to ADC given twice weekly for 4 week, SK-MES-1 tumor-bearing (N=8) mice received the MTD of CPT-11 (q2dx5).
Figure 5A:
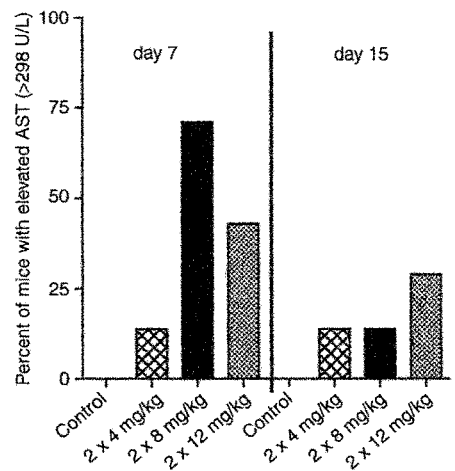
FIG. 5A. Tolerability of hRS7-CL2A-SN-38 in Swiss-Webster mice. Fifty-six Swiss-Webster mice were administered 2 i.p. doses of buffer or the hRS7-CL2A-SN-38 3 days apart (4, 8, or 12 mg/kg of SN-38 per dose; 250, 500, or 750 mg conjugate protein/kg per dose). Seven and 15 days after the last injection, 7 mice from each group were euthanized, with blood counts and serum chemistries performed. Graphs show the percent of animals in each group that had elevated levels of AST.

Studies with the hRS7-CL2A-SN-38 ADC were then extended to 2 other models of human epithelial cancers. In mice bearing BxPC-3 human pancreatic tumors (FIG. 4D), hRS7-CL2A-SN-38 again significantly inhibited tumor growth in comparison to control mice treated with saline or an equivalent amount of nontargeting hA20-CL2A-SN-38 (TV=0.24±0.11 cm$^3$ vs. 1.17±0.45 cm$^3$ and 1.05±0.73 cm$^3$, respectively; $AUC_{day21}$ P<0.001), or irinotecan given at a 10-fold higher SN-38 equivalent dose (TV=0.27+0.18 cm$^3$ vs. 0.90+0.62 cm$^3$, respectively; $AUC_{day25}$ P<0.004) (FIG. 4D). Interestingly, in mice bearing SK-MES-1 human squamous cell lung tumors treated with 0.4 mg/kg of the ADC (FIG. 4E), tumor growth inhibition was superior to saline or unconjugated hRS7 IgG (TV=0.36±0.25 cm$^3$ vs. 1.02±0.70 cm$^3$ and 1.30±1.08 cm$^3$, respectively; $AUC_{2,8d}$, P<0.043), but nontargeting hA20-CL2A-SN-38 or the MTD of irinotecan provided the same antitumor effects as the specific hRS7-SN-38 conjugate (FIG. 5E).

In all murine studies, the hRS7-SN-38 ADC was well tolerated in terms of body weight loss (not shown).

Biodistribution of hRS7-CL2A-SN-38—

The biodistributions of hRS7-CL2A-SN-38 or unconjugated hRS7 IgG were compared in mice bearing SK-MES-1 human squamous cell lung carcinoma xenografts (not shown), using the respective $^{111}$In-labeled substrates. A pharmacokinetic analysis was performed to determine the clearance of hRS7-CL2A-SN-38 relative to unconjugated hRS7 (not shown). The ADC cleared faster than the equivalent amount of unconjugated hRS7, with the ADC exhibiting ~40% shorter half-life and mean residence time. Nonetheless, this had a minimal impact on tumor uptake (not shown). Although there were significant differences at the 24- and 48-hour timepoints, by 72 hours (peak uptake) the amounts of both agents in the tumor were similar. Among the normal tissues, hepatic and splenic differences were the most striking (not shown). At 24 hours postinjection, there was >2-fold more hRS7-CL2A-SN-38 in the liver than hRS7 IgG (not shown). Conversely, in the spleen there was 3-fold more parental hRS7 IgG present at peak uptake (48-hour timepoint) than hRS7-CL2A-SN-38 (not shown). Uptake and clearance in the rest of the tissues generally reflected differences in the blood concentration (not shown).

Because twice-weekly doses were given for therapy, tumor uptake in a group of animals that first received a predose of 0.2 mg/kg (250 μg protein) of the hRS7 ADC 3 days before the injection of the $^{111}$In-labeled antibody was examined. Tumor uptake of $^{111}$In-hRS7-CL2A-SN-38 in predosed mice was substantially reduced at every timepoint in comparison to animals that did not receive the predose (e.g., at 72 hours, predosed tumor uptake was 12.5%±3.8% ID/g vs. 25.4%±8.1% ID/g in animals not given the predose; P=0.0123; not shown http://clincancerres.aacrjournals.org/content/17/10/3157.long—F4). Predosing had no appreciable impact on blood clearance or tissue uptake (not shown). These studies suggest that in some tumor models, tumor accretion of the specific antibody can be reduced by the preceding dose(s), which likely explains why the specificity of a therapeutic response could be diminished with increasing ADC doses and why further dose escalation is not indicated.

Tolerability of hRS7-CL2A-SN-38 in Swiss-Webster Mice and Cynomolgus Monkeys

Figure 5B:
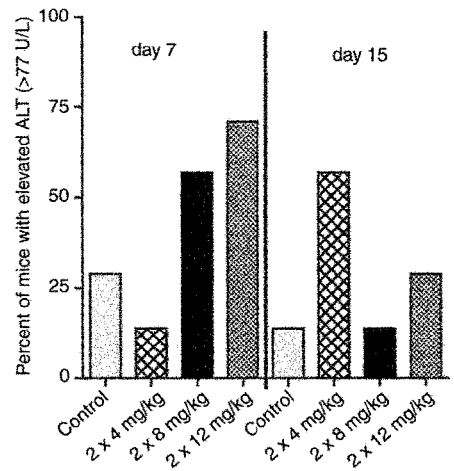
FIG. 5B. Tolerability of hRS7-CL2A-SN-38 in Swiss-Webster mice. Fifty-six Swiss-Webster mice were administered 2 i.p. doses of buffer or the hRS7-CL2A-SN-38 3 days apart (4, 8, or 12 mg/kg of SN-38 per dose; 250, 500, or 750 mg conjugate protein/kg per dose). Seven and 15 days after the last injection, 7 mice from each group were euthanized, with blood counts and serum chemistries performed. Graphs show the percent of animals in each group that had elevated levels of ALT.

Swiss-Webster mice tolerated 2 doses over 3 days, each of 4, 8, and 12 mg SN-38/kg of the hRS7-CL2A-SN-38, with minimal transient weight loss (not shown). No hematopoietic toxicity occurred and serum chemistries only revealed elevated aspartate transamninase (AST, FIG. 5A) and alanine transaminase (ALT, FIG. 5B). Seven days after treatment, AST rose above normal levels (>298 U/L) in all 3 treatment groups (FIG. 5A), with the largest proportion of mice being in the 2×8 mg/kg group. However, by 15 days posttreatment, most animals were within the normal range. ALT levels were also above the normal range (>77 U/L) within 7 days of treatment (FIG. 5B) and with evidence of normalization by Day 15. Livers from all these mice did not show histologic evidence of tissue damage (not shown). In terms of renal function, only glucose and chloride levels were somewhat elevated in the treated groups. At 2×8 mg/kg, 5 of 7 mice had slightly elevated glucose levels (range of 273-320 mg/dL, upper end of normal 263 mg/dL) that returned to normal by 15 days postinjection. Similarly, chloride levels were slightly elevated, ranging from 116 to 127 mmol/L (upper end of normal range 115 mmol/L) in the 2 highest dosage groups (57% in the 2×8 mg/kg group and 100% of the mice in the 2×12 mg/kg group), and remained elevated out to 15 days postinjection. This also could be indicative of gastrointestinal toxicity, because most chloride is obtained through absorption by the gut; however, at termination, there was no histologic evidence of tissue damage in any organ system examined (not shown).

Because mice do not express Trop-2 identified by hRS7, a more suitable model was required to determine the potential of the hRS7 conjugate for clinical use. Immunohistology studies revealed binding in multiple tissues in both humans and Cynomolgus monkeys (breast, eye, gastrointestinal tract, kidney, lung, ovary, fallopian tube, pancreas, parathyroid, prostate, salivary gland, skin, thymus, thyroid, tonsil, ureter, urinary bladder, and uterus; not shown). Based on this cross-reactivity, a tolerability study was performed in monkeys.

Figure 5C:
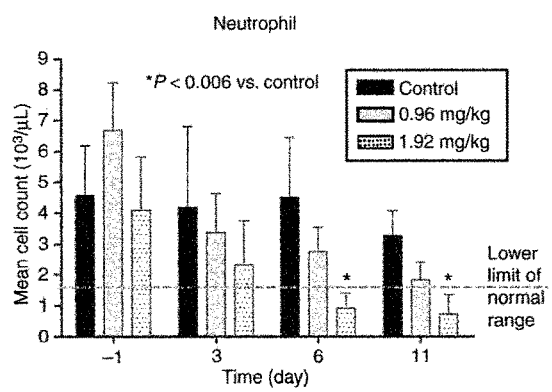
FIG. 5C. Tolerability of hRS7-CL2A-SN-38 in Cynomolgus monkeys. Six monkeys per group were injected twice 3 days apart with buffer (control) or hRS7-CL2A-SN-38 at 0.96 mg/kg or 1.92 mg/kg of SN-38 equivalents per dose (60 and 120 mg/kg conjugate protein). All animals were bled on day −1, 3, and 6. Four monkeys were bled on day 11 in the 0.96 mg/kg group, 3 in the 1.92 mg/kg group. Changes in neutrophil counts in Cynomolgus monkeys.
Figure 5D:
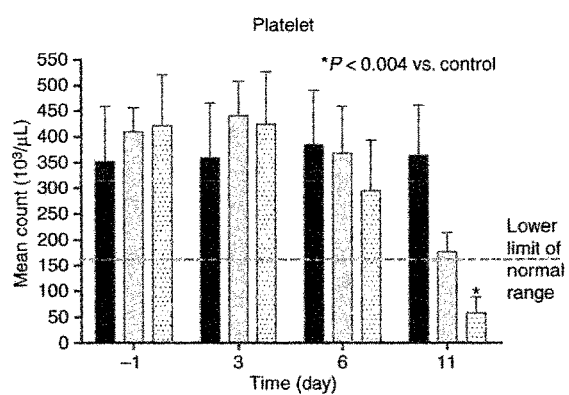
FIG. 5D. Tolerability of hRS7-CL2A-SN-38 in Cynomolgus monkeys. Six monkeys per group were injected twice 3 days apart with buffer (control) or hRS7-CL2A-SN-38 at 0.96 mg/kg or 1.92 mg/kg of SN-38 equivalents per dose (60 and 120 mg/kg conjugate protein). All animals were bled on day −1, 3, and 6. Four monkeys were bled on day 11 in the 0.96 mg/kg group, 3 in the 1.92 mg/kg group. Changes in platelet counts in Cynomolgus monkeys.

The group receiving 2×0.96 mg SN-38/kg of hRS7-CL2A-SN-38 had no significant clinical events following the infusion and through the termination of the study. Weight loss did not exceed 7.3% and returned to acclimation weights by day 15. Transient decreases were noted in most of the blood count data (neutrophil and platelet data shown in FIG. 5C and FIG. 5D), but values did not fall below normal ranges. No abnormal values were found in the serum chemistries. Histopathology of the animals necropsied on day 11 (8 days after last injection) showed microscopic changes in hematopoietic organs (thymus, mandibular and mesenteric lymph nodes, spleen, and bone marrow), gastrointestinal organs (stomach, duodenum, jejunum, ileum, cecum, colon, and rectum), female reproductive organs (ovary, uterus, and vagina), and at the injection site. These changes ranged from minimal to moderate and were fully reversed at the end of the recovery period (day 32) in all tissues, except in the thymus and gastrointestinal tract, which were trending towards full recovery at this later timepoint (not shown).

At the 2×1.92 mg SN-38/kg dose level of the conjugate, there was 1 death arising from gastrointestinal complications and bone marrow suppression, and other animals within this group showed similar, but more severe adverse events than the 2×0.96 mg/kg group (not shown). These data indicate that dose-limiting toxicities were identical to that of irinotecan; namely, intestinal and hematologic. Thus, the MTD for hRS7-CL2A-SN-38 lies between 2×0.96 and 1.92 mg SN-38/kg, which represents a human equivalent dose of 2×0.3 to 0.6 mg/kg SN-38.

Discussion

Trop-2 is a protein expressed on many epithelial tumors, including lung, breast, colorectal, pancreas, prostate, and ovarian cancers, making it a potentially important target for delivering cytotoxic agents (Ohmachi et al., 2006, Clin Cancer Res 12:3057-63; Fong et al., 2008, Br J Cancer 99:1290-95; Cubas et al., 2009, Biochim Biophys Acta 1796:309-14). The RS7 antibody internalizes when bound to Trop-2 (Shih et al., 1995, Cancer Res 55:5857s-63s), which enables direct intracellular delivery of cytotoxics.

SN-38 is a potent topoisomerase-I inhibitor, with $IC_{50}$ values in the nanomolar range in several cell lines. It is the active form of the prodrug, irinotecan, that is used for the treatment of colorectal cancer, and which also has activity in lung, breast, and brain cancers. We reasoned that a directly targeted SN-38, in the form of an ADC, would be a significantly improved therapeutic over CPT-11, by overcoming the latter's low and patient-variable bioconversion to active SN-38 (Mathijssen et al., 2001, Clin Cancer Res 7:2182-94).

The Phe-Lys peptide inserted in the original CL2 derivative allowed for possible cleavage via cathepsin B. To simplify the synthetic process, in CL2A the phenylalanine was eliminated, and thus the cathepsin B cleavage site was removed. Interestingly, this product had a better-defined chromatographic profile compared to the broad profile obtained with CL2 (not shown), but more importantly, this change had no impact on the conjugate's binding, stability, or potency in side-by-side testing. These data suggest that SN-38 in CL2 was released from the conjugate primarily by the cleavage at the pH-sensitive benzyl carbonate bond to SN-38's lactone ring and not the cathepsin B cleavage site.

In vitro cytotoxicity of hRS7 ADC against a range of solid tumor cell lines consistently had $IC_{50}$ values in the nmol/L range. However, cells exposed to free SN-3 8 demonstrated a lower $IC_{50}$ value compared to the ADC. This disparity between free and conjugated SN-38 was also reported for ENZ-2208 (Sapra et al., 2008, Clin Cancer Res 14:1888-96, Zhao et al., 2008, Bioconjug Chem 19:849-59) and NK012 (Koizumi et al., 2006, Cancer Res 66:10048-56). ENZ-2208 utilizes a branched PEG to link about 3.5 to 4 molecules of SN-38 per PEG, whereas NK012 is a micelle nanoparticle containing 20% SN-38 by weight. With our ADC, this disparity (i.e., ratio of potency with free vs. conjugated SN-38) decreased as the Trop-2 expression levels increased in the tumor cells, suggesting an advantage to targeted delivery of the drug. In terms of in vitro serum stability, both the CL2- and CL2A-SN-38 forms of hRS7-SN-38 yielded a $t_{1/2}$ of ~20 hours, which is in contrast to the short $t_{1/2}$ of 12.3 minutes reported for ENZ-2208 (Zhao et al., 2008, Bioconjug Chem 19:849-59), but similar to the 57% release of SN-38 from NK012 under physiological conditions after 24 hours (Koizumi et al., 2006, Cancer Res 66:10048-56).

Treatment of tumor-bearing mice with hRS7-SN-38 (either with CL2-SN-38 or CL2A-SN-3 8) significantly inhibited tumor growth in 5 different tumor models. In 4 of them, tumor regressions were observed, and in the case of Calu-3, all mice receiving the highest dose of hRS7-SN-38 were tumor-free at the conclusion of study. Unlike in humans, irinotecan is very efficiently converted to SN-3 8 by a plasma esterase in mice, with a greater than 50% conversion rate, and yielding higher efficacy in mice than in humans (Morton et al., 2000, Cancer Res 60:4206-10; Furman et al., 1999, J Clin Oncol 17:1815-24). When irinotecan was administered at 10-fold higher or equivalent SN-38 levels, hRS7-SN-38 was significantly better in controlling tumor growth. Only when irinotecan was administered at its MTD of 24 mg/kg q2dx5 (37.5-fold more SN-38) did it equal the effectiveness of hRS7-SN-38. In patients, we would expect this advantage to favor hRS7-CL2A-SN-38 even more, because the bioconversion of irinotecan would be substantially lower.

We also showed in some antigen-expressing cell lines, such as SK-MES-1, that using an antigen-binding ADC does not guarantee better therapeutic responses than a nonbinding, irrelevant conjugate. This is not an unusual or unexpected finding. Indeed, the nonbinding SN-38 conjugates mentioned earlier enhance therapeutic activity when compared to irinotecan, and so an irrelevant IgG-SN-38 conjugate is expected to have some activity. This is related to the fact that tumors have immature, leaky vessels that allow the passage of macromolecules better than normal tissues (Jain, 1994, Sci Am 271:58-61). With our conjugate, 50% of the SN-38 will be released in ~13 hours when the pH is lowered to a level mimicking lysosomal levels (e.g., pH 5.3 at 37° C.; data not shown), whereas at the neutral pH of serum, the release rate is reduced nearly 2-fold. If an irrelevant conjugate enters an acidic tumor microenvironment, it is expected to release some SN-38 locally. Other factors, such as tumor physiology and innate sensitivities to the drug, will also play a role in defining this "baseline" activity. However, a specific conjugate with a longer residence time should have enhanced potency over this baseline response as long as there is ample antigen to capture the specific antibody. Biodistribution studies in the SK-MES-1 model also showed that if tumor antigen becomes saturated as a consequence of successive dosing, tumor uptake of the specific conjugate is reduced, which yields therapeutic results similar to that found with an irrelevant conjugate.

Although it is challenging to make direct comparisons between our ADC and the published reports of other SN-38 delivery agents, some general observations can be made. In our therapy studies, the highest individual dose was 0.4 mg/kg of SN-38. In the Calu-3 model, only 4 injections were given for a total cumulative dose of 1.6 mg/kg SN-38 or 32 µg SN-38 in a 20 g mouse. Multiple studies with ENZ-2208 were done using its MTD of 10 mg/kg×5 (Sapra et al., 2008, Clin Cancer Res 14:1888-96; Pastorini et al., 2010, Clin Cancer Res 16:4809-21), and preclinical studies with NK012 involved its MTD of 30 mg/kg×3 (Koizumi et al., 2006, Cancer Res 66:10048-56). Thus, significant antitumor effects were obtained with hRS7-SN-38 at 30-fold and 55-fold less SN-38 equivalents than the reported doses in ENZ-2208 and NK012, respectively. Even with 10-fold less hRS7 ADC (0.04 mg/kg), significant antitumor effects were observed, whereas lower doses of ENZ-2208 were not presented, and when the NK012 dose was lowered 4-fold to 7.5 mg/kg, efficacy was lost (Koizumi et al., 2006, Cancer Res 66:10048-56). Normal mice showed no acute toxicity with a cumulative dose over 1 week of 24 mg/kg SN-38 (1,500 mg/kg of the conjugate), indicating that the MTD was higher. Thus, tumor-bearing animals were effectively treated with 7.5- to 15-fold lower amounts of SN-38 equivalents.

Biodistribution studies revealed the hRS7-CL2A-SN-38 had similar tumor uptake as the parental hRS7 IgG, but cleared substantially faster with 2-fold higher hepatic uptake, which may be due to the hydrophobicity of SN-38. With the ADC being cleared through the liver, hepatic and gastrointestinal toxicities were expected to be dose limiting. Although mice had evidence of increased hepatic transaminases, gastrointestinal toxicity was mild at best, with only transient loss in weight and no abnormalities noted upon histopathologic examination. Interestingly, no hematological toxicity was noted. However, monkeys showed an identical toxicity profile as expected for irinotecan, with gastrointestinal and hematological toxicity being dose-limiting.

Because Trop-2 recognized by hRS7 is not expressed in mice, it was important to perform toxicity studies in monkeys that have a similar tissue expression of Trop-2 as humans. Monkeys tolerated 0.96 mg/kg/dose (~12 mg/m²) with mild and reversible toxicity, which extrapolates to a human dose of ~0.3 mg/kg/dose (~11 mg/m²). In a Phase I clinical trial of NK012, patients with solid tumors tolerated 28 mg/m² of SN-38 every 3 weeks with Grade 4 neutropenia as dose-limiting toxicity (DLT; Hamaguchi et al., 2010, Clin Cancer Res 16:5058-66). Similarly, Phase I clinical trials with ENZ-2208 revealed dose-limiting febrile neutropenia, with a recommendation to administer 10 mg/m² every 3 weeks or 16 mg/m² if patients were administered G-CSF (Kurzrock et al., AACR-NCI-EORTC International Conference on Molecular Targets and Cancer Therapeutics; 2009 Nov. 15-19; Boston, Mass.; Poster No C216; Patnaik et al., AACR-NCI-EORTC International Conference on Molecular Targets and Cancer Therapeutics; 2009 Nov. 15-19; Boston, Mass.; Poster No C221). Because monkeys tolerated a cumulative human equivalent dose of 22 mg/m², it appears that even though hRS7 binds to a number of normal tissues, the MTD for a single treatment of the hRS7 ADC could be similar to that of the other nontargeting SN-38 agents. Indeed, the specificity of the anti-Trop-2 antibody did not appear to play a role in defining the DLT, because the toxicity profile was similar to that of irinotecan. More importantly, if antitumor activity can be achieved in humans as in mice that responded with human equivalent dose of just at 0.03 mg SN-38 equivalents/kg/dose, then significant antitumor responses may be realized clinically.

In conclusion, toxicology studies in monkeys, combined with in vivo human cancer xenograft models in mice, have indicated that this ADC targeting Trop-2 is an effective therapeutic in several tumors of different epithelial origin.

Example 4. Anti-Trop-2 ADC Comprising hRS7 and Paclitaxel

A new antibody-drug conjugate (ADC) was made by conjugating paclitaxel (TAXOL®) to the hRS7 anti-human Trop-2 antibody (hRS7-paclitaxel). The final product had a mean drug to antibody substitution ratio of 2.2. This ADC was tested in vitro using two different Trop-2-positive cell lines as targets: BxPC-3 (human pancreatic adenocarcinoma) and MDA-MB-468 (human triple negative breast carcinoma). One day prior to adding the ADC, cells were harvested from tissue culture and plated into 96-well plates at 2000 cells per well. The next day cells were exposed to free paclitaxel ($6.1 \times 10^{-11}$ to $4 \times 10^{-6}$ M) or the drug-equivalent of hRS7-paclitaxel. For comparison, hRS7-SN-38 and free SN-38 were also tested at a range of $3.84 \times 10^{-12}$ to $2.5 \times 10^{-7}$ M. Plates were incubated at 37° C. for 96 h. After this incubation period, an MTS substrate was added to all of the plates and read for color development at half-hour intervals until untreated control wells had an $OD_{492nm}$ reading of approximately 1.0. Growth inhibition was measured as a percent of growth relative to untreated cells using Microsoft Excel and Prism software (non-linear regression to generate sigmoidal dose response curves which yield $IC_{50}$-values).

Figure 6:
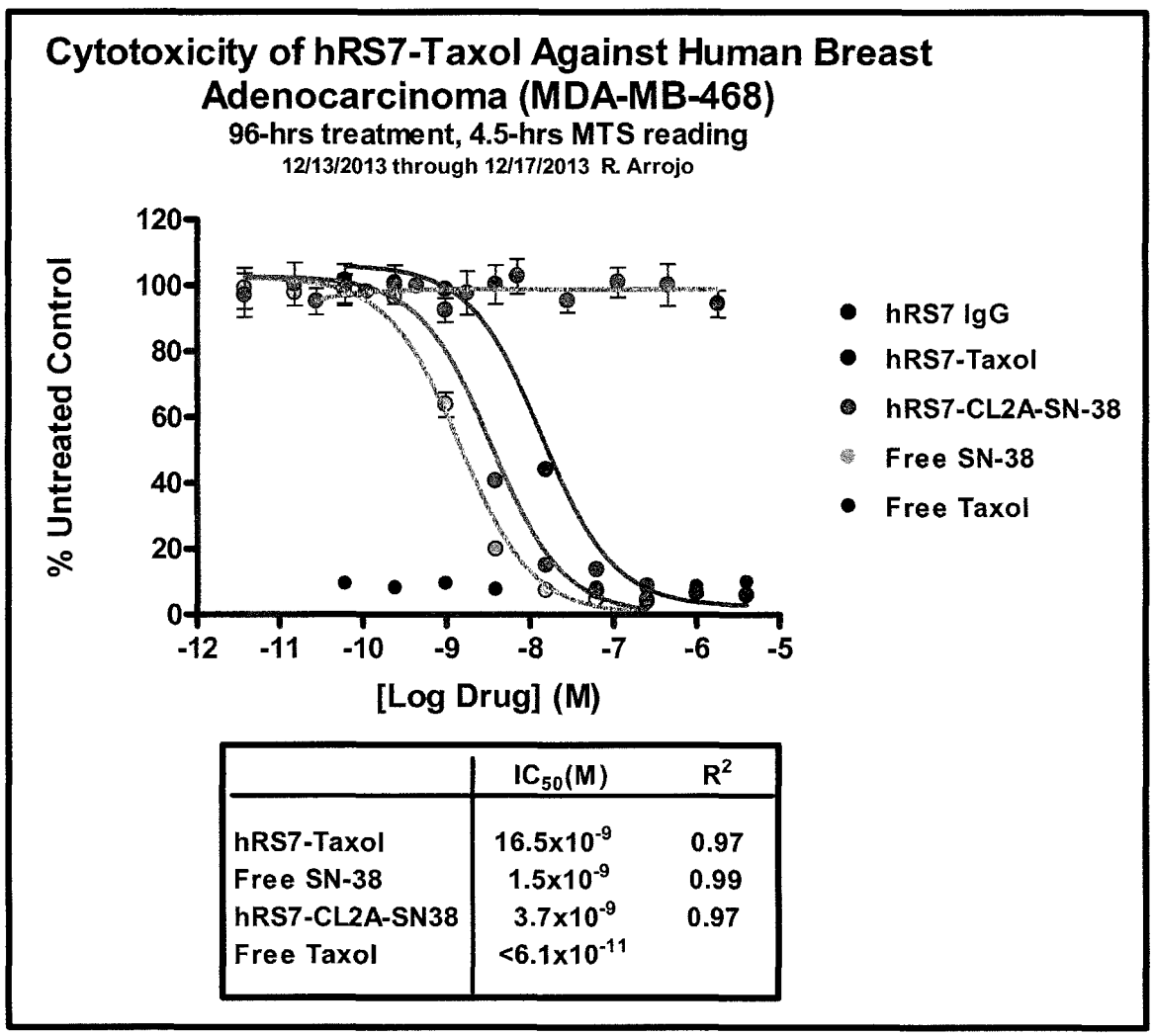
FIG. 6. In vitro efficacy of anti-Trop-2-paclitaxel ADC against MDA-MB-468 human breast adenocarcinoma.
Figure 7:
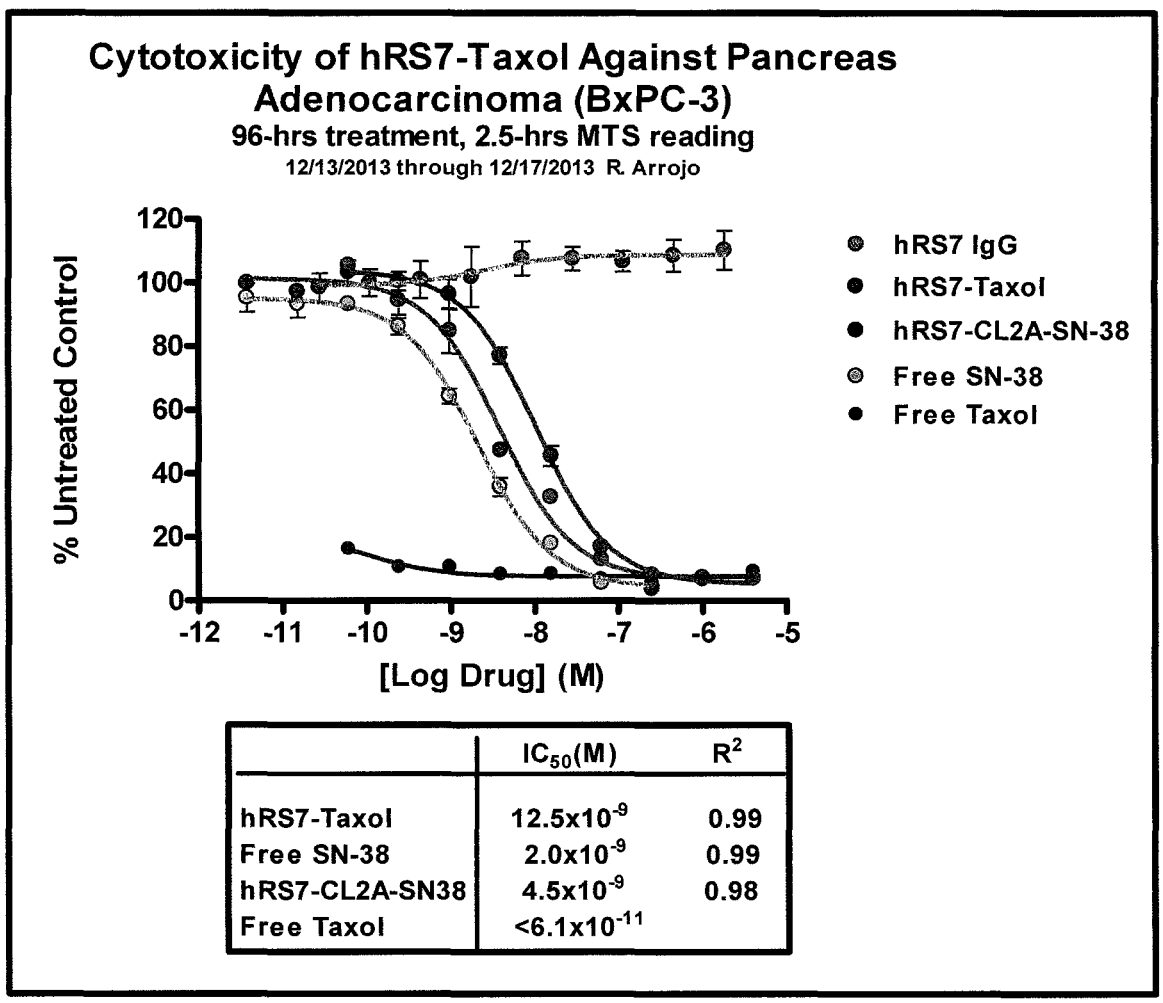
FIG. 7. In vitro efficacy of anti-Trop-2-paclitaxel ADC against BxPC-3 human pancreatic adenocarcinoma.

The hRS7-paclitaxel ADC exhibited cytotoxic activity in the MDA-MB-468 breast cell line (FIG. 6), with an $IC_{50}$-value approximately 4.5-fold higher than hRS7-SN-38. The free paclitaxel was much more potent than the free SN-38 (FIG. 6). While the $IC_{50}$ for free SN-38 was $1.54 \times 10^{-9}$ M, the $IC_{50}$ for free paclitaxel was less than $6.1 \times 10^{-11}$ M. Similar results were obtained for the BxPC-3 pancreatic cell line (FIG. 7) in which the hRS7-paclitaxel ADC had an $IC_{50}$-value approximately 2.8-fold higher than the hRS7-SN-38 ADC. These results show the efficacy of anti-Trop-2 conjugated paclitaxel in vitro, with $IC_{50}$-values in the nanomolar range, similar to the hRS7-SN-38 ADC.

Example 5. Cell Binding Assay of Anti-Trop-2 Antibodies

Two different murine monoclonal antibodies against human Trop-2 were obtained for ADC conjugation. The first, 162-46.2, was purified from a hybridoma (ATCC, HB-187) grown up in roller-bottles. A second antibody, MAB650, was purchased from R&D Systems (Minneapolis, Minn.). For a comparison of binding, the Trop-2 positive human gastric carcinoma, NCI-N87, was used as the target. Cells ($1.5 \times 10^5$/well) were plated into 96-well plates the day before the binding assay. The following morning, a dose/response curve was generated with 162-46.2, MAB650, and murine RS7 (0.03 to 66 nM). These primary antibodies were incubated with the cells for 1.5 h at 4° C. Wells were washed and an anti-mouse-HRP secondary antibody was added to all the wells for 1 h at 4° C. Wells are washed again followed by the addition of a luminescence substrate. Plates were read using Envision plate reader and values are reported as relative luminescent units.

All three antibodies had similar $K_D$-values of 0.57 nM for RS7, 0.52 nM for 162-46.2 and 0.49 nM for MAB650. However, when comparing the maximum binding ($B_{max}$) of 162-46.2 and MAB650 to RS7 they were reduced by 25% and 50%, respectively ($B_{Max}$ 11,250 for RS7, 8,471 for 162-46.2 and 6,018 for MAB650) indicating different binding properties in comparison to RS7.

Example 6. Cytotoxicity of Anti-Trop-2 ADC (MAB650-SN-38)

A novel anti-Trop-2 ADC was made with SN-38 and MAB650, yielding a mean drug to antibody substitution ratio of 6.89. Cytotoxicity assays were performed to compare the MAB650-SN-38 and hRS7-SN-38 ADCs using two different human pancreatic adenocarcinoma cell lines (BxPC-3 and Capan-1) and a human triple negative breast carcinoma cell line (MDA-MB-468) as targets.

One day prior to adding the ADCs, cells were harvested from tissue culture and plated into 96-well plates. The next day cells were exposed to hRS7-SN-38, MAB650-SN-38, and free SN-38 at a drug range of $3.84 \times 10^{-12}$ to $2.5 \times 10^{-7}$ M. Unconjugated MAB650 was used as a control at protein equivalent doses as the MAB650-SN-38. Plates were incubated at 37° C. for 96 h. After this incubation period, an MTS substrate was added to all of the plates and read for color development at half-hour intervals until an $OD_{492nm}$ of approximately 1.0 was reached for the untreated cells. Growth inhibition was measured as a percent of growth relative to untreated cells using Microsoft Excel and Prism software (non-linear regression to generate sigmoidal dose response curves which yield $IC_{50}$-values.

Figure 8B:
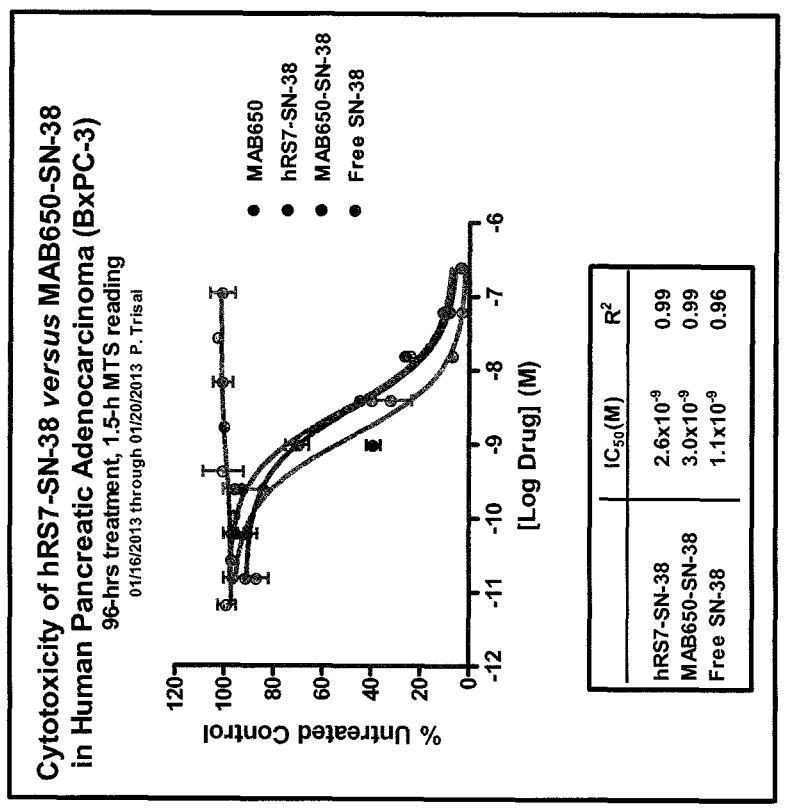
FIG. 8B. Comparison of in vitro efficacy of anti-Trop-2 ADCs (hRS7-SN-38 versus MAB650-SN-38) in BxPC-3 human pancreatic adenocarcinoma.
Figure 8A:
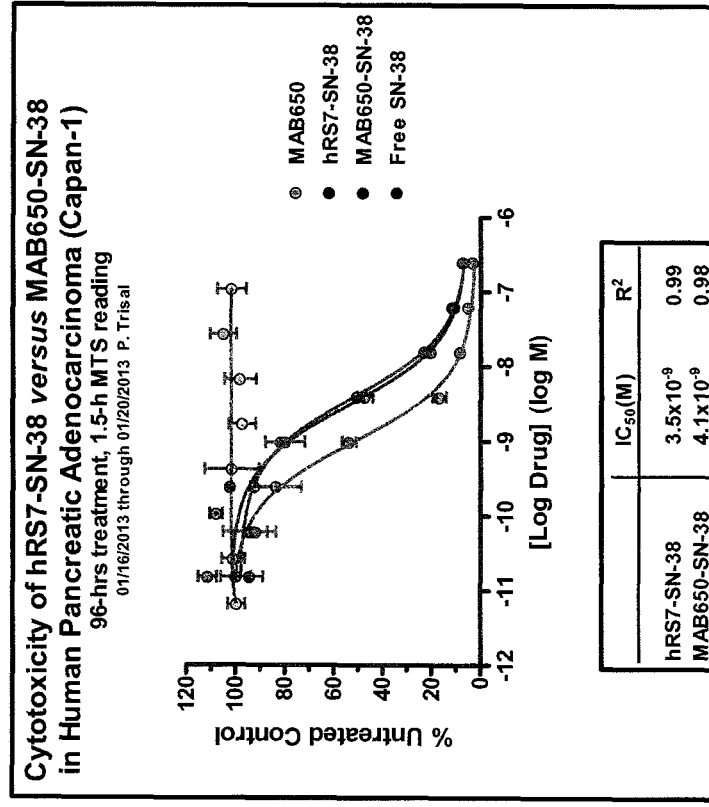
FIG. 8A. Comparison of in vitro efficacy of anti-Trop-2 ADCs (hRS7-SN-38 versus MAB650-SN-38) in Capan-1 human pancreatic adenocarcinoma.
Figure 8C:
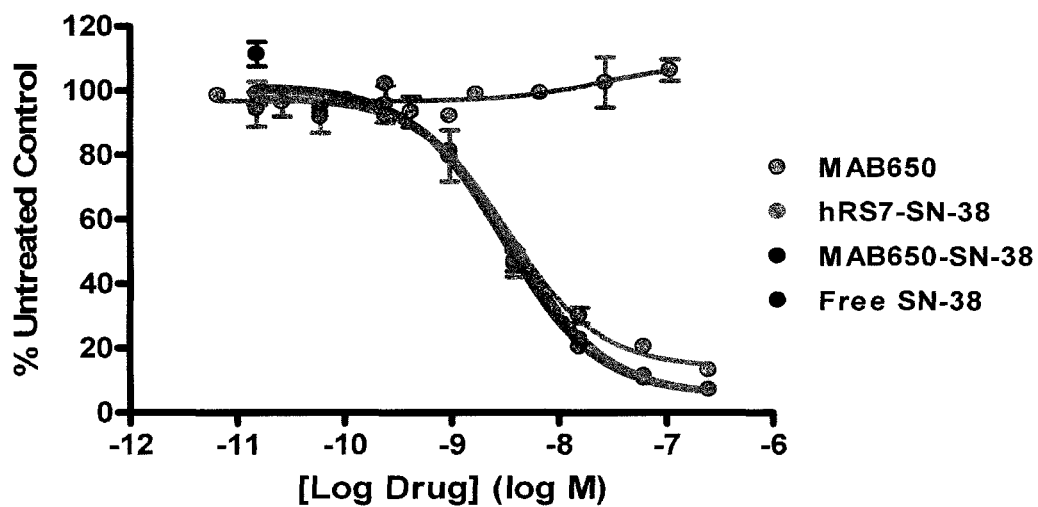
FIG. 8C. Comparison of in vitro efficacy of anti-Trop-2 ADCs (hRS7-SN-38 versus MAB650-SN-38) in NCI-N87 human gastric adenocarcinoma.

As shown in FIG. 8, hRS7-SN-38 and MAB650-SN-38 had similar growth-inhibitory effects with $IC_{50}$-values in the low nM range which is typical for SN-38-ADCs in these cell lines. In the human Capan-1 pancreatic adenocarcinoma cell line (FIG. 8A), the hRS7-SN-38 ADC showed an $IC_{50}$ of 3.5 nM, compared to 4.1 nM for the MAB650-SN-38 ADC and 1.0 nM for free SN-38. In the human BxPC-3 pancreatic adenocarcinoma cell line (FIG. 8B), the hRS7-SN-38 ADC showed an $IC_{50}$ of 2.6 nM, compared to 3.0 nM for the MAB650-SN-38 ADC and 1.0 nM for free SN-38. In the human NCI-N87 gastric adenocarcinoma cell line (FIG. 8C), the hRS7-SN-38 ADC showed an $IC_{50}$ of 3.6 nM, compared to 4.1 nM for the MAB650-SN-38 ADC and 4.3 nM for free SN-38.

In summary, in these in vitro assays, the SN-38 conjugates of two anti-Trop-2 antibodies, hRS7 and MAB650, showed equal efficacies against several tumor cell lines, which was similar to that of free SN-38. Because the targeting function of the anti-Trop-2 antibodies would be a much more significant factor in vivo than in vitro, the data support that anti-Trop-2-SN-38 ADCs as a class would be highly efficacious in vivo, as demonstrated in the Examples above for hRS7-SN-38.

Example 7. Cytotoxicity of Anti-Trop-2 ADC (162-46.2-SN-38)

A novel anti-Trop-2 ADC was made with SN-38 and 162-46.2, yielding a drug to antibody substitution ratio of 6.14. Cytotoxicity assays were performed to compare the 162-46.2-SN-38 and hRS7-SN-38 ADCs using two different Trop-2-positive cell lines as targets, the BxPC-3 human pancreatic adenocarcinoma and the MDA-MB-468 human triple negative breast carcinoma.

One day prior to adding the ADC, cells were harvested from tissue culture and plated into 96-well plates at 2000 cells per well. The next day cells were exposed to hRS7-SN-38, 162-46.2-SN-38, or free SN-38 at a drug range of $3.84 \times 10^{-12}$ to $2.5 \times 10^{-7}$ M. Unconjugated 162-46.2 and hRS7 were used as controls at the same protein equivalent doses as the 162-46.2-SN-38 and hRS7-SN-38, respectively. Plates were incubated at 37° C. for 96 h. After this incubation period, an MTS substrate was added to all of the plates and read for color development at half-hour intervals until untreated control wells had an $OD_{492nm}$ reading of approximately 1.0. Growth inhibition was measured as a percent of growth relative to untreated cells using Microsoft Excel and Prism software (non-linear regression to generate sigmnoidal dose response curves which yield $IC_{50}$-values).

Figure 9B:
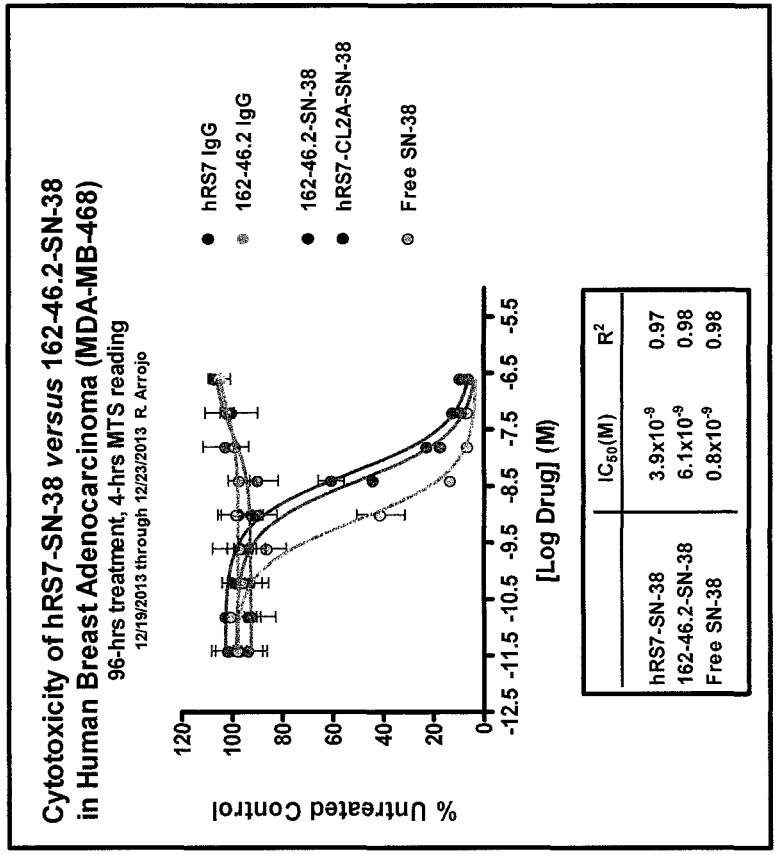
FIG. 9B. Comparison of cytotoxicity of naked or SN-38 conjugated hRS7 vs. 162-46.2 antibodies in MDA-MB-468 human breast adenocarcinoma.
Figure 9A:
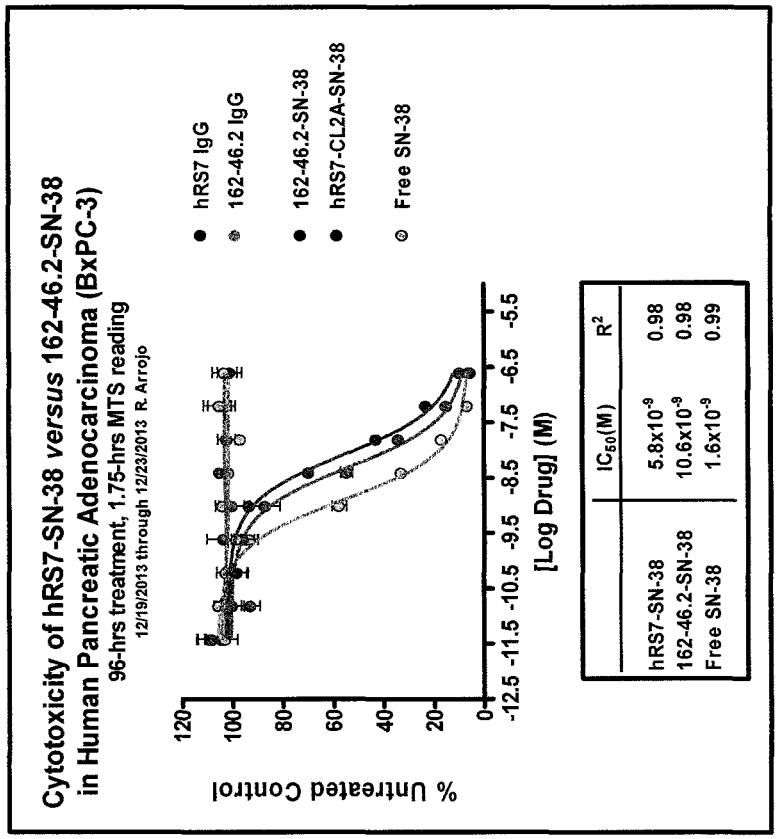
FIG. 9A. Comparison of cytotoxicity of naked or SN-38 conjugated hRS7 vs. 162-46.2 antibodies in BxPC-3 human pancreatic adenocarcinoma.

As shown in FIG. 9A and FIG. 9B, the 162-46.2-SN-38 ADC had a similar $IC_{50}$-values when compared to hRS7-SN-38. When tested against the BxPC-3 human pancreatic adenocarcinoma cell line (FIG. 9A), hRS7-SN-38 had an $IC_{50}$ of 5.8 nM, compared to 10.6 nM for 162-46.2-SN-38 and 1.6 nM for free SN-38. When tested against the MDA-MB-468 human breast adenocarcinoma cell line (FIG. 9B), hRS7-SN-38 had an $IC_{50}$ of 3.9 nM, compared to 6.1 nM for 162-46.2-SN-38 and 0.8 nM for free SN-38. The free antibodies alone showed little cytotoxicity to either Trop-2 positive cancer cell line.

In summary, comparing the efficacies in vitro of three different anti-Trop-2 antibodies conjugated to the same cytotoxic drug, all three ADCs exhibited equivalent cytotoxic effects against a variety of Trop-2 positive cancer cell lines. These data support that the class of anti-Trop-2 antibodies, incorporated into drug-conjugated ADCs, are effective anti-cancer therapeutic agents for Trop-2 expressing solid tumors.

Example 8. Clinical Trials with IMMU-132 Anti-Trop-2 ADC Comprising hRS7 Antibody Conjugated to SN-38

Summary

The present Example reports results from a phase I clinical trial and ongoing phase II extension with IMMU-132, an ADC of the internalizing, humanized, hRS7 anti-Trop-2 antibody conjugated by a pH-sensitive linker to SN-38 (mean drug-antibody ratio=7.6). Trop-2 is a type I transmembrane, calcium-transducing, protein expressed at high density ($\sim 1 \times 10^5$), frequency, and specificity by many human carcinomas, with limited normal tissue expression. Preclinical studies in nude mice bearing Capan-1 human pancreatic tumor xenografts have revealed IMMU-132 is capable of delivering as much as 120-fold more SN-38 to tumor than derived from a maximally tolerated irinotecan therapy.

The present Example reports the initial Phase I trial of 25 patients who had failed multiple prior therapies (some including topoisomerase-I/II inhibiting drugs), and the ongoing Phase II extension now reporting on 69 patients, including in colorectal (CRC), small-cell and non-small cell lung (SCLC, NSCLC, respectively), triple-negative breast (TNBC), pancreatic (PDC), esophageal, and other cancers.

As discussed in detail below, Trop-2 was not detected in serum, but was strongly expressed ($\geq 2^+$) in most archived tumors. In a 3+3 trial design, IMMU-132 was given on days 1 and 8 in repeated 21-day cycles, starting at 8 mg/kg/dose, then 12 and 18 mg/kg before dose-limiting neutropenia. To optimize cumulative treatment with minimal delays, phase II is focusing on 8 and 10 mg/kg (n=30 and 14, respectively). In 49 patients reporting related AE at this time, neutropenia $\geq$G3 occurred in 28% (4% G4). Most common non-hematological toxicities initially in these patients have been fatigue (55%; $\geq$G3=9%), nausea (53%; $\geq$G3=0%), diarrhea (47%; $\geq$G3=9%), alopecia (40%), and vomiting (32%; $\geq$G3=2%). Homozygous UGT1A1*28/*28 was found in 6 patients, 2 of whom had more severe hematological and GI toxicities. In the Phase I and the expansion phases, there are now 48 patients (excluding PDC) who are assessable by RECIST/CT for best response. Seven (15%) of the patients had a partial response (PR), including patients with CRC (N=1), TNBC (N=2), SCLC (N=2), NSCLC (N=1), and esophageal cancers (N=1), and another 27 patients (56%) had stable disease (SD), for a total of 38 patients (79%) with disease response; 8 of 13 CT-assessable PDC patients (62%) had SD, with a median time to progression (TTP) of 12.7 wks compared to 8.0 weeks in their last prior therapy. The TTP for the remaining 48 patients is 12.6+ wks (range 6.0 to 51.4 wks).

Plasma CEA and CA19-9 correlated with responses. No anti-hRS7 or anti-SN-38 antibodies were detected despite dosing over months. The conjugate cleared from the serum within 3 days, consistent with in vivo animal studies where 50% of the SN-38 was released daily, with >95% of the SN-38 in the serum being bound to the IgG in a non-glucoronidated form, and at concentrations as much as 100-fold higher than SN-38 reported in patients given irinotecan. These results show that the hRS7-SN-38-containing ADC is therapeutically active in metastatic solid cancers, with manageable diarrhea and neutropenia.

Pharmacokinetics

Two ELISA methods were used to measure the clearance of the IgG (capture with anti-hRS7 idiotype antibody) and the intact conjugate (capture with anti-SN-38 IgG/probe with anti-hRS7 idiotype antibody). SN-38 was measured by HPLC. Total IMMU-132 fraction (intact conjugate) cleared more quickly than the IgG (not shown), reflecting known gradual release of SN-38 from the conjugate. HPLC determination of SN-38 (Unbound and TOTAL) showed >95% the SN-3 8 in the serum was bound to the IgG. Low concentrations of SN-3 8G suggest SN-38 bound to the IgG is protected from glucoronidation. Comparison of ELISA for conjugate and SN-38 HPLC revealed both overlap, suggesting the ELISA is a surrogate for monitoring SN-38 clearance.

A summary of the dosing regiment and patient poll is provided in Table 3.

TABLE 3

Clinical Trial Parameters

| | |
|---|---|
| Dosing regimen | Once weekly for 2 weeks administered every 21 days for up to 8 cycles. In the initial enrollment, the planned dose was delayed and reduced if $\geq$G2 treatment-related toxicity; protocol was amended to dose delay and reduction only in the event of $\geq$G3 toxicity. |
| Dose level cohorts | 8, 12, 18 mg/kg; later reduced to an intermediate dose level of 10 mg/kg. |
| Cohort size | Standard Phase I [3 + 3] design; expansion includes 15 patients in select cancers. |
| DLT | G4 ANC $\geq$7 d; $\geq$G3 febrile neutropenia of any duration; G4 Plt $\geq$5 d; G4 Hgb; Grade 4 N/V/D any duration/G3 N/V/D for >48 h; G3 infusion-related reactions; related $\geq$G3 non-hematological toxicity. |
| Maximum Acceptable Dose (MAD) | Maximum dose where $\geq$2/6 patients tolerate $1^{st}$ 21-d cycle w/o delay or reduction or $\geq$G3 toxicity. |
| Patients | Metastatic colorectal, pancreas, gastric, esophageal, lung (NSCLC, SCLC), triple-negative breast (TNBC), prostate, ovarian, renal, urinary bladder, head/neck, hepatocellular. Refractory/relapsed after standard treatment regimens for metastatic cancer. Prior irinotecan-containing therapy NOT required for enrollment. No bulky lesion >5 cm. Must be 4 weeks beyond any major surgery, and 2 weeks beyond radiation or chemotherapy regimen. Gilbert's disease or known CNS metastatic disease are excluded. |

Clinical Trial Status

A total of 69 patients (including 25 patients in Phase I) with diverse metastatic cancers having a median of 3 prior therapies were reported. Eight patients had clinical progression and withdrew before CT assessment. Thirteen CT-assessable pancreatic cancer patients were separately reported. The median TTP (time to progression) in PDC patients was 11.9 wks (range 2 to 21.4 wks) compared to median 8 wks TTP for the preceding last therapy.

Figure 10:
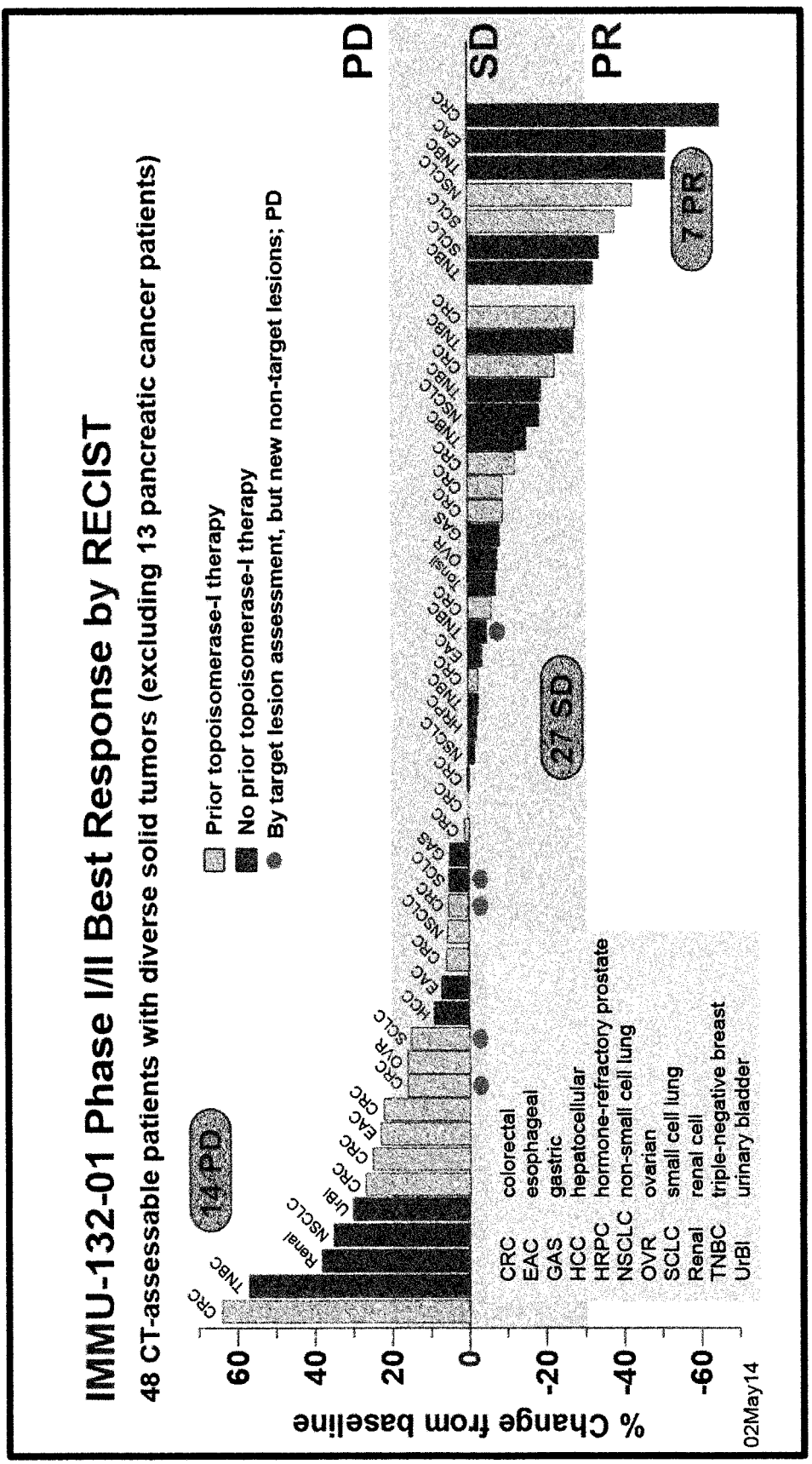
FIG. 10. IMMU-132 phase I/II data for best response by RECIST criteria.
Figure 11:
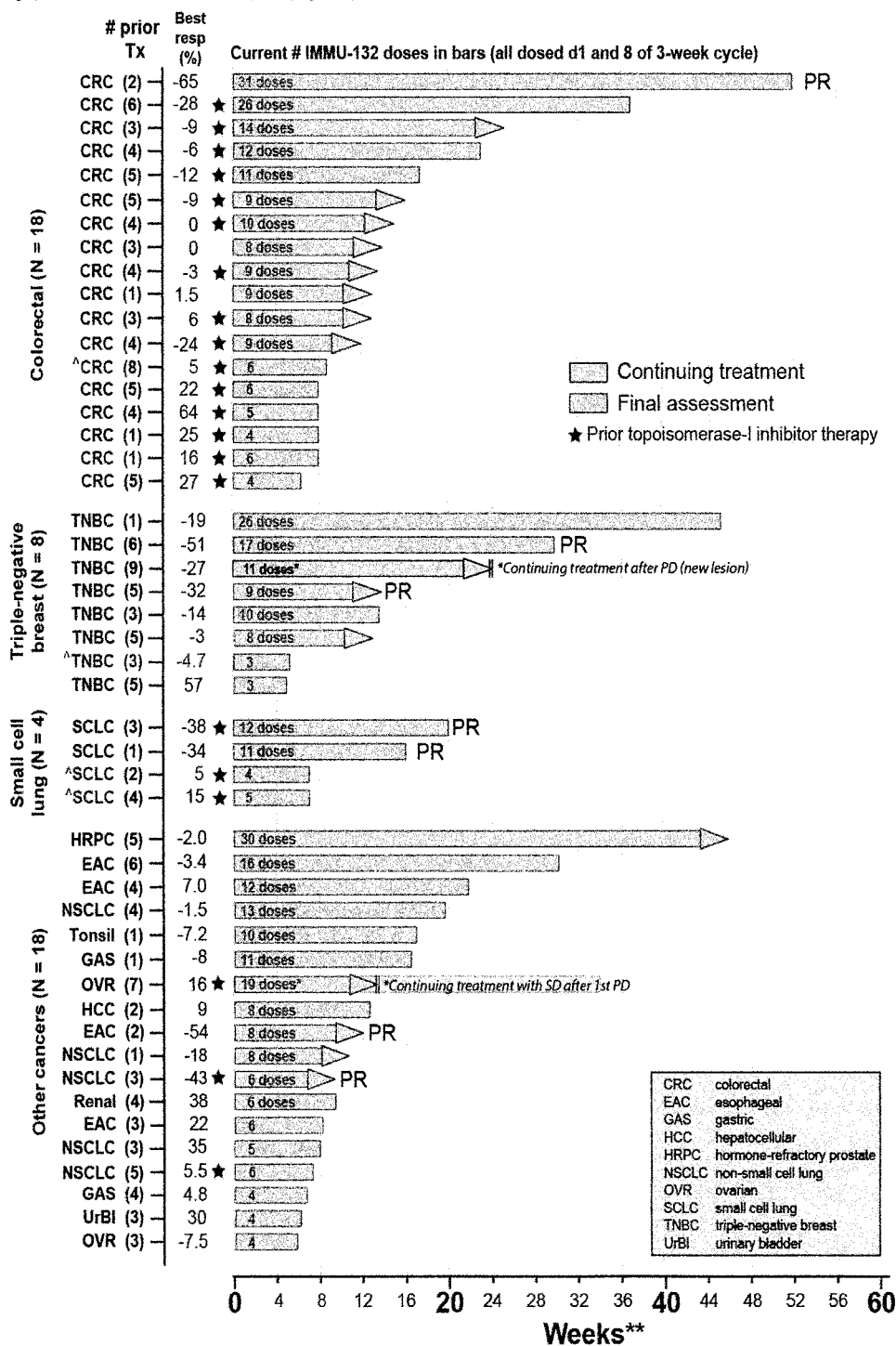
FIG. 11. IMMU-132 phase I/II data for time to progression and best response (RECIST).

A total of 48 patients with diverse cancers had at least 1 CT-assessment from which Best Response (FIG. 10) and Time to Progression (TTP; FIG. 11) were determined. To summarize the Best Response data, of 8 assessable patients with TNBC (triple-negative breast cancer), there were 2 PR (partial response), 4 SD (stable disease) and 2 PD (progressive disease) for a total response [PR+SD] of 6/8 (75%). For SCLC (small cell lung cancer), of 4 assessable patients there were 2 PR, 0 SD and 2 PD for a total response of 2/4 (50%). For CRC (colorectal cancer), of 18 assessable patients there were 1 PR, 11 SD and 6 PD for a total response of 12/18 (67%). For esophageal cancer, of 4 assessable patients there were 1 PR, 2 SD and 1 PD for a total response of 3/4 (75%). For NSCLC (non-small cell lung cancer), of 5 assessable patients there were 1 PR, 3 SD and 1 PD for a total response of 4/5 (80%). Over all patients treated, of 48 assessable patients there were 7 PR, 27 SD and 14 PD for a total response of 34/48 (71%). These results demonstrate that the anti-Trop-2 ADC (hRS7-SN-38) showed significant clinical efficacy against a wide range of solid tumors in human patients.

The reported side effects of therapy (adverse events) are summarized in Table 4. As apparent from the data of Table 4, the therapeutic efficacy of hRS7-SN-38 was achieved at dosages of ADC showing an acceptably low level of adverse side effects.

TABLE 4

Related Adverse Events Listing for IMMU-132-01
Criteria: Total ≥10% or ≥Grade 3

| | N = 47 patients | | |
|---|---|---|---|
| | TOTAL | Grade 3 | Grade 4 |
| Fatigue | 55% | 4 (9%) | 0 |
| Nausea | 53% | 0 | 0 |
| Diarrhea | 47% | 4 (9%) | 0 |
| Neutropenia | 43% | 11 (24%) | 2 (4%) |
| Alopecia | 40% | — | — |
| Vomiting | 32% | 1 (2%) | 0 |
| Anemia | 13% | 2 (4%) | 0 |
| Dysgeusia | 15% | 0 | 0 |
| Pyrexia | 13% | 0 | 0 |
| Abdominal pain | 11% | 0 | 0 |
| Hypokalemia | 11% | 1 (2%) | 0 |
| WBC Decrease | 6% | 1 (2%) | 0 |
| Febrile Neutropenia | 6% | 1 (2%) | 2 (4%) |
| Deep vein thrombosis | 2% | 1 (2%) | 0 |

Grading by CTCAE v 4.0

Exemplary partial responses to the anti-Trop-2 ADC were confirmed by CT data (not shown). As an exemplary PR in CRC, a 62 year-old woman first diagnosed with CRC underwent a primary hemicolectomy. Four months later, she had a hepatic resection for liver metastases and received 7 mos of treatment with FOLFOX and 1 mo 5FU. She presented with multiple lesions primarily in the liver (3+ Trop-2 by immunohistology), entering the hRS7-SN-38 trial at a starting dose of 8 mg/kg about 1 year after initial diagnosis. On her first CT assessment, a PR was achieved, with a 37% reduction in target lesions (not shown). The patient continued treatment, achieving a maximum reduction of 65% decrease after 10 months of treatment (not shown) with decrease in CEA from 781 ng/mL to 26.5 ng/mL), before progressing 3 months later.

As an exemplary PR in NSCLC, a 65 year-old male was diagnosed with stage IIIB NSCLC (sq. cell). Initial treatment of carboplatin/etoposide (3 mo) in concert with 7000 cGy XRT resulted in a response lasting 10 mo. He was then started on Tarceva maintenance therapy, which he continued until he was considered for IMMU-132 trial, in addition to undergoing a lumbar laminectomy. He received first dose of IMMU-132 after 5 months of Tarceva, presenting at the time with a 5.6 cm lesion in the right lung with abundant pleural effusion. He had just completed his 6$^{th}$ dose two months later when the first CT showed the primary target lesion reduced to 3.2 cm (not shown).

As an exemplary PR in SCLC, a 65 year-old woman was diagnosed with poorly differentiated SCLC. After receiving carboplatin/etoposide (Topo-II inhibitor) that ended after 2 months with no response, followed with topotecan (Topo-I inhibitor) that ended after 2 months, also with no response, she received local XRT (3000 cGy) that ended 1 month later. However, by the following month progression had continued. The patient started with IMMU-132 the next month (12 mg/kg; reduced to 6.8 mg/kg; Trop-2 expression 3+), and after two months of IMMU-132, a 38% reduction in target lesions, including a substantial reduction in the main lung lesion occurred (not shown). The patient progressed 3 months later after receiving 12 doses.

These results are significant in that they demonstrate that the anti-Trop-2 ADC was efficacious, even in patients who had failed or progressed after multiple previous therapies.

In conclusion, at the dosages used, the primary toxicity was a manageable neutropenia, with few Grade 3 toxicities. IMMU-132 showed evidence of activity (PR and durable SD) in relapsed/refractory patients with triple-negative breast cancer, small cell lung cancer, non-small cell lung cancer, colorectal cancer and esophageal cancer, including patients with a previous history of relapsing on topoisomerase-I inhibitor therapy. These results show efficacy of the anti-Trop-2 ADC in a wide range of cancers that are resistant to existing therapies.

Example 9. Conjugation of Bifunctional SN-38 Products to Mildly Reduced Antibodies The anti-CEACAM5 humanized MAb, hMN-14 (also known as labetuzumab), the anti-CD22 humanized MAb, hLL2 (also known as epratuzumab), the anti-CD20 humanized MAb, hA20 (also known as veltuzumab), the anti-EGP-1 humanized MAb, hRS7, and anti-mucin humanized MAb, hPAM4 (also known as clivatuzumab), were conjugated to SN-38 using a CL2A linker. Each antibody was reduced with dithiothreitol (DTT), used in a 50-to-70-fold molar excess, in 40 mM PBS, pH 7.4, containing 5.4 mM EDTA, at 37° C. (bath) for 45 min. The reduced product was purified by size-exclusion chromatography and/or diafiltration, and was buffer-exchanged into a suitable buffer at pH 6.5. The thiol content was determined by Ellman's assay, and was in the 6.5-to-8.5 SH/IgG range. Alternatively, the antibodies were reduced with Tris (2-carboxyethyl) phosphine (TCEP) in phosphate buffer at pH in the range of 5-7, followed by in situ conjugation. The reduced MAb was reacted with ~10-to-15-fold molar excess of CL2A-SN-38 using DMSO at 7-15% v/v as co-solvent, and incubating for 20 min at ambient temperature. The conjugate was purified by centrifuged SEC, passage through a hydrophobic column, and finally by ultrafiltration-diafiltration. The product was assayed for SN-38 by absorbance at 366 nm and correlating with standard values, while the protein concentration was deduced from absorbance at 280 nm, corrected for spillover of SN-38 absorbance at this wavelength. This way, the SN-38/MAb substitution ratios were determined. The purified conjugates were stored as lyophilized formulations in glass vials, capped under vacuum and stored in a −20° C. freezer. SN-38 molar substitution ratios (MSR) obtained for these conjugates were typically in the 5-to-7 range.

Example 10. Combination Therapy with Anti-Trop-2 ADC in SCLC

Since cisplatinum is one of the main chemotherapeutics used in combination with irinotecan in advanced small-cell lung cancer (SCLC), an experiment was performed testing the combination of cisplatinum with IMMU-132 in mice bearing human SCLC tumors (DMS 53). Furthermore, carboplatin was tested in this tumor model since it too is used clinically in SCLC.

Female C.B.-17 SCID mice were injected s.c. with a tumor suspension made from of DMS 53 stock tumors (20% w/v) plus cells harvested from tissue culture ($5\times10^6$ cells per mouse) mixed 1:1 with matrigel. Once tumors reached a mean tumor volume of 0.270+0.048 cm$^3$, the animals were divided up into nine different treatment groups of 9 mice each. Three groups of mice received IMMU-132 (500, 250 or 100 μg i.p.) while a control group received a non-tumor targeting antibody-drug conjugate made with h679, a humanized anti-histamine-succinyl-glycine IgG (h679-SN-38; 500 μg i.p.). All were administered twice weekly for 4 weeks. Two groups received only chemotherapy of either cisplatinum (5 mg/kg i.p.) or carboplatin (50 mg/kg i.p.) weekly for 4 weeks. Two groups received a combination of IMMU-132 (250 μg i.v. weekly×4 wks) plus either cisplatinum or carboplatin. A final untreated control group of mice received saline (100 μL i.p. twice weekly×4 wks). Tumors were measured and mice weighed twice weekly.

Results

Figure 12:
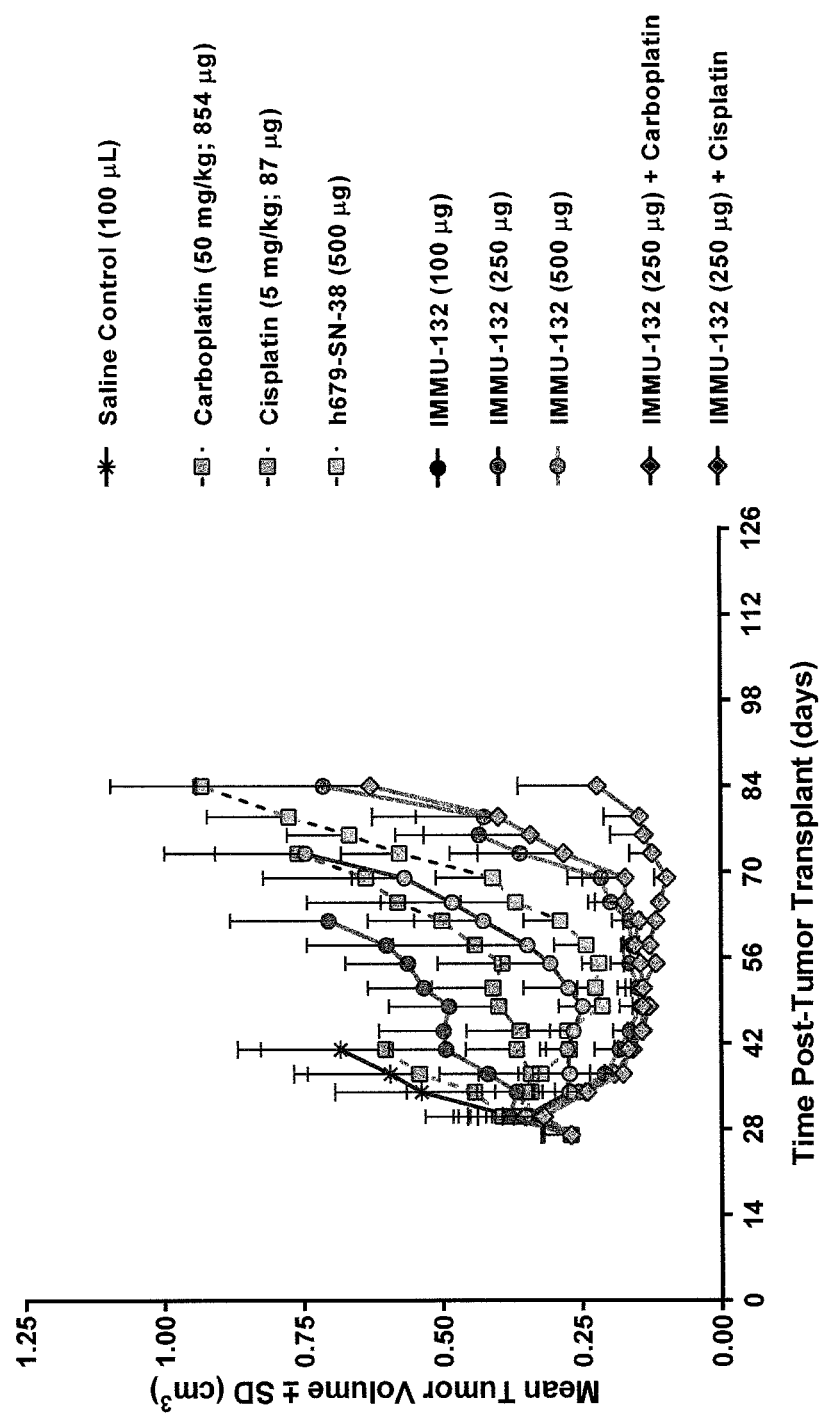
FIG. 12. Combination therapy with IMMU-132 and carboplatin or cisplatin, compared to IMMU-132, carboplatin or cisplatin alone, a non-targeting ADC or saline control.

Mean tumor volumes for the various groups are shown in FIG. 12. All three doses of IMMU-132 provided a significant antitumor effect compared to saline control animals (P<0.0161; AUC one-tailed t-test). Therapy with the highest dose of IMMU-132 (500 μg) produced significantly greater tumor regressions in tumor-bearing mice compared to all the monotherapy groups, including control h679-SN-38 (P<0.0032; AUC two-tailed t-test).

Figure 13:
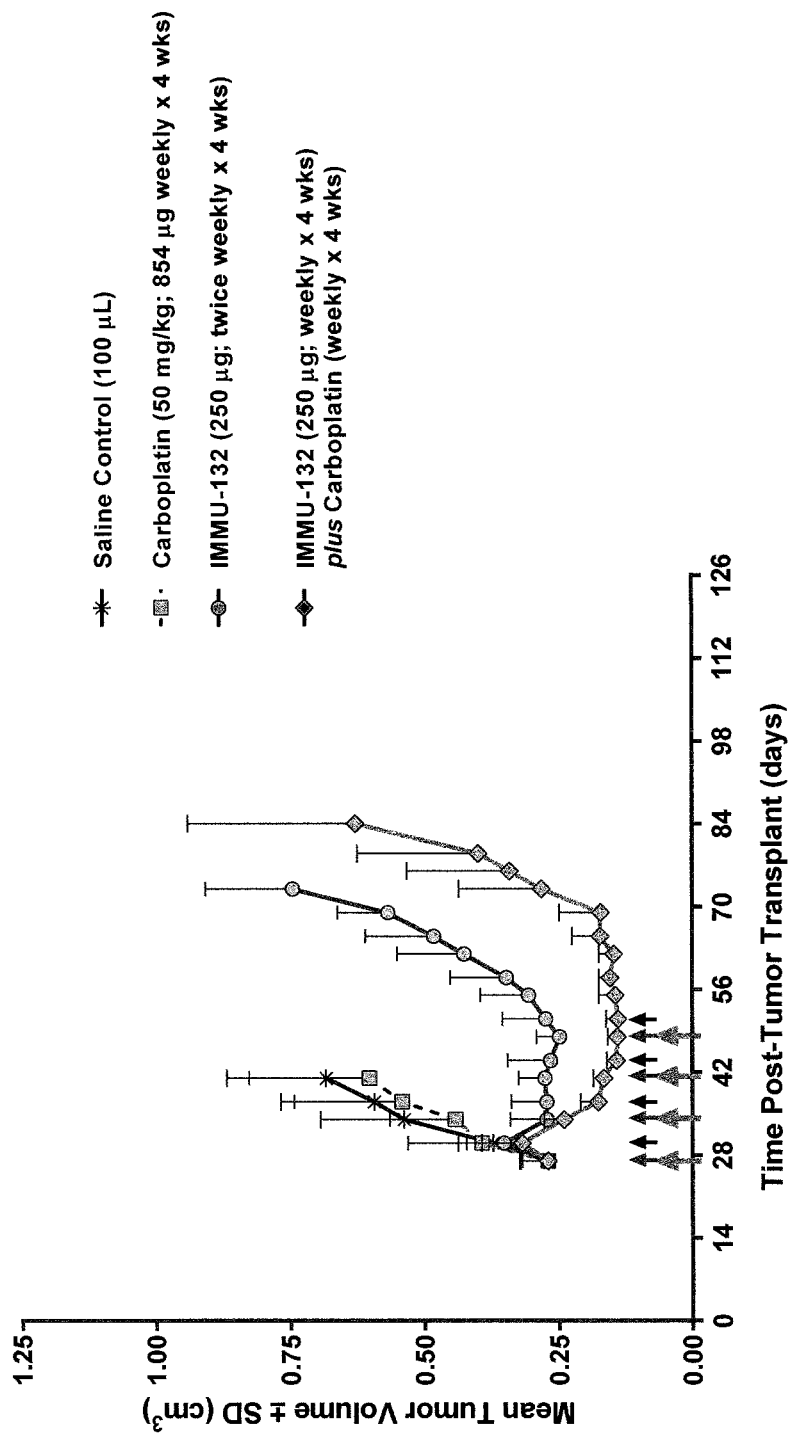
FIG. 13. Combination therapy with IMMU-132 plus carboplatin, compared to IMMU-132 or caboplatin alone or saline control.

For the combination groups, IMMU-132 (250 μg) plus carboplatin (FIG. 13) was approaching significance (P=0.0983; AUC two-tailed t-test) at the time the first mouse in the control carboplatin monotherapy group reached its end-point of tumor volume >1.0 $cm^3$ on day 41 (therapy day 14). However, in terms of absolute mean tumor volumes, on this day the combination of IMMU-132 (250 μg) plus carboplatin had significantly smaller tumors when compared to carboplatin monotherapy (0.166±0.019 $cm^3$ vs. 0.602±0.224 $cm^3$, respectively; P=0.0004, two-tailed t-test). When compared to mice treated with only IMMU-132 (250 μg twice weekly), the IMMU-132 (weekly) plus carboplatin treated animals had significantly smaller tumors as of day 73 (last day of comparison due to several mice reaching end-point; 0.745+0.162 $cm^3$ vs. 0.282±0.153 $cm^3$, respectively; P=0.0003, AUC two-tailed t-test).

Figure 14:
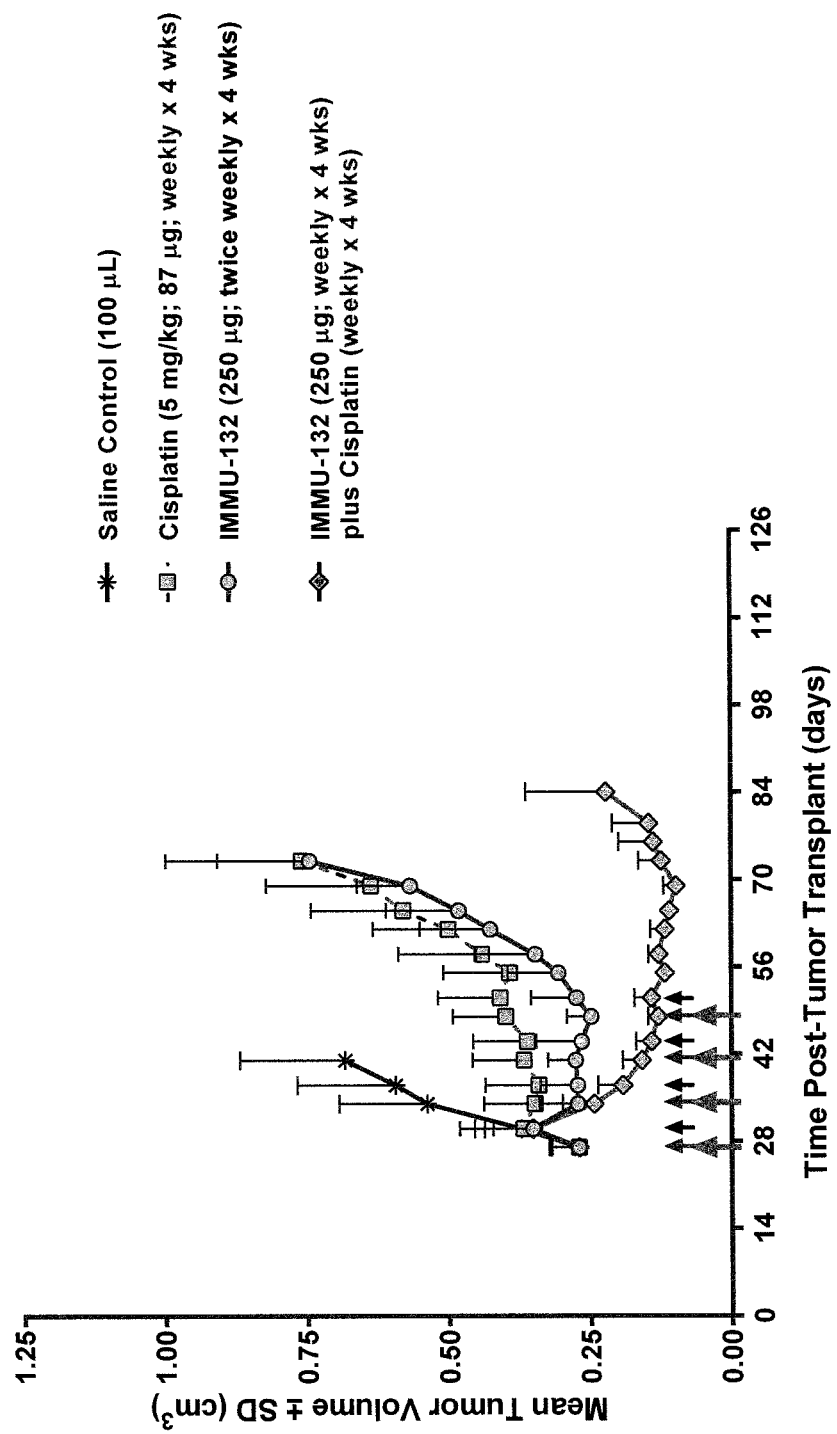
FIG. 14. Combination therapy with IMMU-132 plus cisplatinum, compared to IMMU-132 or cisplatinum alone or saline control.

Mice treated with the combination of IMMU-132 (250 μg) plus cisplatinum (FIG. 14) exhibited significant tumor-growth inhibition when compared to cisplatinum monotherapy (P=0.0002, AUC two-tailed t-test). When tumor volumes were compared on day 73 (last day of comparison due to several mice in cisplatinum monotherapy group reaching end-point), the combination group had tumors that were ~6.2-fold smaller than those in the cisplatinum monotherapy group (0.123±0.040 $cm^3$ vs. 0.758±0.240 $cm^3$, respectively; P<0.0001, two-tailed t-test). Likewise, mice treated with the weekly schedule of IMMU-132 (250 μg) combined with cisplatinum had significantly smaller tumors than animals treated with only IMMU-132 (250 μg) even though in the monotherapy group IMMU-132 was administered twice weekly (P<0.0001, AUC two-tailed t-test). Finally, the combination of IMMU-132 plus cisplatinum proved to be superior to all the other groups including IMMU-132 plus carboplatin combination and high dose IMMU-132 (500 μg) monotherapy treatment groups (P<0.0066, AUC two-tailed t-test).

Figure 15:
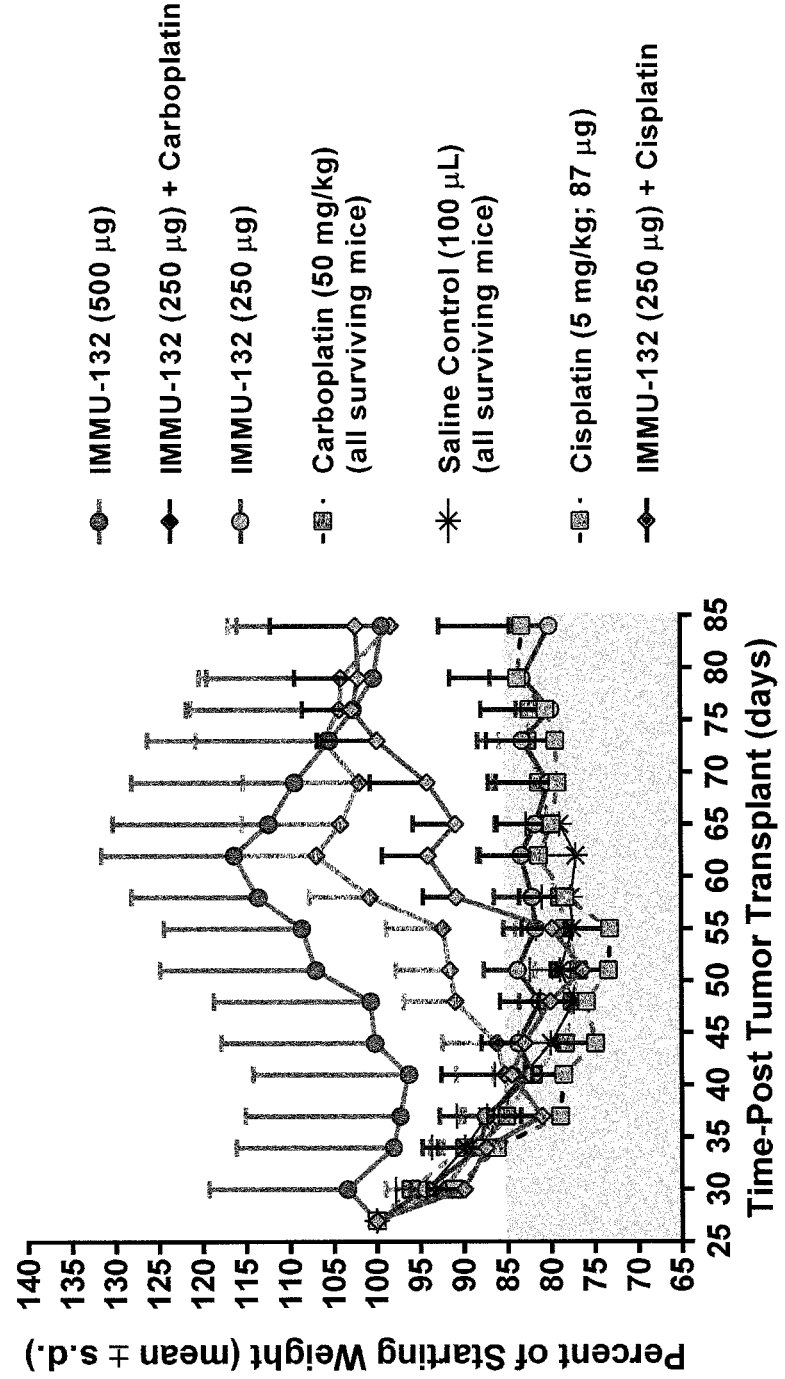
FIG. 15. Cachexia in mice treated with combination therapy with IMMU-132 and carboplatin or cisplatin, compared to IMMU-132, carboplatin or cisplatin alone, or saline control.

Both the IMMU-132 plus carboplatin treatment as well as the IMMU-132 plus cisplatinum treatment were well tolerated by the mice. An unusual aspect of this tumor model was the observation that mice bearing DMS 53 tumors exhibited cachexia (FIG. 15) with weights dropping on average greater than 15% from the start. For example, in the saline control mice, as the tumor burden grew from 0.270±0.053 $cm^3$ on day 27 to 0.683±0.185 $cm^3$ on day 41, the animal's body weight dropped 16.9%±3.4%. However, as the antitumor effects of IMMU-132 (500 μg) monotherapy or the combinations of IMMU-132 plus carboplatin or cisplatinum became evident, the mice began to gain weight again. For example, in the IMMU-132 plus carboplatin group, mice lost their greatest weight by day 38 (15.3%±5.6%), after which, they began to regain this lost weight as the tumors regressed with the mice returning to 100% of starting weight by day 58. During that time, the tumors regressed to 0.128±0.0.018 $cm^3$ from a starting size of 0.270±0.050 $cm^3$ on day 27. However, animals began to lose weight again as the tumors regrew to a size larger than when therapy started (0.282+0.153 $cm^3$ on day 73). In short, as the tumor-burden was decrease by these therapies, the debilitating effects of cachexia were being reversed in these mice, further indicating the benefit of these combinations in this human SCLC disease model.

Example 11. Therapy of Human mSCLC Patients with Anti-Trop-2-SN-38 ADC

Summary

Topotecan, a topoisomerase I inhibitor, is approved as a second-line therapy in patients sensitive to first-line platinum-containing regimens, but no new therapeutic has been approved for the treatment of metastatic small-cell lung cancer (mSCLC) in twenty years. In this Example, a novel antibody-drug conjugate (ADC), sacituzumab govitecan, comprised of an antibody targeting Trop-2 and containing the active metabolite of irinotecan, SN-38 (also a topoisomerase I inhibitor), was studied. Patients with a median of 2 prior therapies (range 1-7) received the ADC on days 1 and 8 of 21-day cycles, with a median of ten doses (range, 1 to 63) being given. The principal grade ≥3 toxicities were manageable neutropenia, fatigue, and diarrhea. Despite up to 63 repeated doses, the ADC was not immunogenic.

Forty-nine percent of the 43 assessable patients had a reduction of tumor size from baseline; the objective response rate (partial responses) was 16% and stable disease was achieved in 49% of patients. Median progression-free survival and median overall survival were 3.6 and 7.0 months, respectively, based on an intention-to-treat (N=53) analysis. This ADC was active in patients who were chemosensitive or chemoresistant to first-line chemotherapy, and also in patients who failed second-line topotecan therapy. These data support the use of sacituzumab govitecan as a new therapeutic for advanced mSCLC.

Methods

Patients ≥18 years of age with mSCLC who had relapsed or were refractory to at least one prior standard line of therapy for stage IV metastatic disease, and with measurable tumors by CT, were enrolled. They were required to have Eastern Cooperative Oncology Group (ECOG) performance status of 0 or 1, adequate bone marrow, hepatic and renal function, and other eligibility as described in the phase I trial (Starodub et al., 2015, Clin Cancer Res 21:3870-8). Previous therapy had to be completed at least 4 weeks before enrollment.

The overall objective of this portion of the basket trial being conducted for diverse cancers (ClinicalTrials.gov, NCT01631552) was to evaluate safety and antitumor activity of sacituzumab govitecan in patients with mSCLC. Sacituzumab govitecan was administered intravenously at an initial infusion rate of 50 mg/h, completed within 3 h (subsequent infusions completed within 60-90 min). Pre-medications (e.g., diphenhydramine, acetaminophen, and dexamethasone) were prescribed optionally to reduce the risk of infusion reactions. Doses of 8 or 10 mg/kg were given on days 1 and 8 of a 21-day cycle, with contingencies to delay (maximum of 2 weeks). Toxicities were managed by supportive hematopoietic growth-factor therapy for blood cell reduction, dose delays and/or modification as specified in the protocol (e.g., 25% of prior dose), or by standard medical practice. Treatment was continued until disease progression, initiation of alternative anticancer therapy, unacceptable toxicity, or withdrawal of consent.

Fifty-three patients were enrolled with mSCLC (30 females, 23 males, with a median age 63 years (range, 44-82). The median time from initial diagnosis to treatment with sacituzumab govitecan was 9.5 months (range, 3 to 53). Most patients were heavily pretreated, with a median of 2 prior lines of therapy (range, 1 to 7). Everyone received cisplatinum or carboplatin plus etoposide. Twenty-two (41%) patients had 1 prior line of therapy, while 14 (26%) and 17 (32%) were given 2 and ≥3 prior chemotherapy regimens, respectively. In addition, 18 (33%) received topotecan and/or irinotecan, 9 (16%) had a taxane, and 5 (9%) had an immune checkpoint inhibitor therapy, comprising nivolumab (N=4) or atezolizumab (N=1).

Based on a duration of response to a platinum-containing frontline therapy greater or less than 3 months, there were 27 (51%) and 26 (49%) chemosensitive and chemoresistant patients, respectively. Most patients had extensive disease, with metastases to multiple organs, including lungs (66%), liver (59%), lymph nodes (76%), chest (34%), adrenals (25%), bone (23%), and pleura (6%). Other sites of disease included pancreas (N=4), brain (N=2), skin (N=2), and esophageal wall, ovary, and sinus (1 each).

The primary endpoint was the proportion of patients with a confirmed objective response, assessed approximately every 8 weeks until disease progression, by each institution's radiology group or a contracted local radiology service. Objective responses were assessed by Response Evaluation Criteria in Solid Tumors, version 1.1 (RECIST 1.1) (Eisenhauer et al., 2009, Eur J Cancer 45:228-47). Partial (PR) or complete responses (CR) required confirmation within 4 to 6 weeks after the initial response. Clinical benefit rate (CBR) is defined as those patients with an objective response plus stable disease (SD)≥4 months. Survival was monitored every 3 months until death or withdrawal of consent.

Safety evaluations were conducted during scheduled visits or more frequently if warranted. Blood count and serum chemistries were checked routinely before administration of sacituzumab govitecan and when clinically indicated.

Statistical Analyses—

The data included in the analyses were derived from patients enrolled from November 2013 to June 2016, with follow-up through Jan. 31, 2017. The frequency and severity of adverse events (AEs) were defined by MedDRA Preferred Term and System Organ Class (SOC) version 10, with severity assessed by NCI-CTCAE v4.03. All patients who received sacituzumab govitecan were evaluated for toxicities.

The protocol provided that objective response rates (ORR) were determined for patients who received ≥2 doses (1 cycle) and had their initial 8-week CT assessment. Duration of response is defined in accordance to RECIST 1.1 criteria, with those having an objective response marked from time of the first evidence of response until progression, while stable disease duration is marked from the start of treatment until progression. PFS and OS are defined from the start of treatment until an objective assessment of progression was determined (PFS) or death (OS). Duration of response, PFS, and OS were estimated by Kaplan-Meier methods, with 95% confidence intervals (CI), using MedCalc Statistical Software, version 16.4.3 (Ostend, Belgium).

Tumor Trop-2 Immunohistochemistry and Immunogenicity of Sacituzumab Govitecan and Components—

Archival tumor specimens for Trop-2 were stained by IHC and interpreted as reported previously (Starodub et al., 2015, Clin Cancer Res 21:3870-8). Positivity required at least 10% of the tumor cells to be stained, with an intensity scored as 1+(weak), 2+(moderate), and 3+(strong). Antibody responses to sacituzumab govitecan, the IgG antibody, and SN-38 were monitored in serum samples taken at baseline and then prior to each even-numbered cycle by enzyme-linked immunosorbent assays performed by the sponsor (Starodub et al., 2015, Clin Cancer Res 21:3870-8). Assay sensitivity is 50 ng/mL for the ADC and the IgG, and 170 ng/mL for anti-SN-38 antibody.

TABLE 5

Baseline demographics and disease characteristics of all patients (N = 53)

| | | |
|---|---|---|
| Age | Years (median; range) | 63 (44-82) |
| Gender, N (%) | Female | 30 (56) |
| | Male | 23 (44) |
| Race, N (%) | White | 47 (88) |
| | Black | 3 (6) |
| | Other | 3 (6) |
| ECOG, N (%) | 0 | 6 (11) |
| | 1 | 47 (89) |
| Sites of metastases, N (%) | Lung | 35 (66) |
| | Liver | 18 (59) |
| | Lymph nodes | 40 (76) |
| | Chest | 18 (34) |
| | Adrenals | 13 (25) |
| | Bone | 12 (23) |
| | Pleural effusion | 3 (5) |
| | Pancreas | 4 (7) |
| | Pelvis | 2 (3) |
| | Brain | 2 (3) |
| | Skin | 2 (3) |
| | Others | 3 (5) |
| Prior Lines of Therapy N (%) | 1 | 22 (41) |
| | 2 | 14 (26) |
| | ≥3 | 17 (32) |
| Sensitivity to 1$^{st}$ line chemotherapy, N (%) | Sensitive | 27 (51) |
| | Resistant | 26 (49) |
| Prior Therapy, N (%) | Platinum and Etoposide | 53 (100) |
| | Topotecan and/or Irinotecan | 18 (33) |
| | Taxanes | 9 (16) |
| | Checkpoint inhibitors (CPI) | 5 (9) |

Results

Patients—

From November 2013 to June 2016, 53 patients were enrolled with mSCLC (30 females, 23 males, with a median age 63 years (range, 44-82) (Table 5). The median time from initial diagnosis to treatment with sacituzumab govitecan was 9.5 months (range, 3 to 53). Most patients were heavily pretreated, with a median of 2 prior lines of therapy (range, 1 to 7). Everyone received cisplatin or carboplatin plus etoposide. Twenty-two (41%) patients had 1 prior line of therapy, while 14 (26%) and 17 (32%) were given 2 and ≥3 prior chemotherapy regimens, respectively. In addition, 18 (33%) received topotecan and/or irinotecan, 9 (16%) had a taxane, and 5 (9%) had an immune checkpoint inhibitor therapy, comprising nivolumab (N=4) or atezolizumab (N=1). Based on a duration of response to a platinum-containing frontline therapy greater or less than 3 months, there were 27 (51%) and 26 (49%) chemosensitive and chemoresistant patients, respectively. Most patients had extensive disease, with metastases to multiple organs, including lungs (66%), liver (59%), lymph nodes (76%), chest (34%), adrenals (25%), bone (23%), and pleura (6%) (Table 5). Other sites of disease included pancreas (N=4), brain (N=2), skin (N=2), and esophageal wall, ovary, and sinus (1 each).

Treatment Exposure, Safety and Tolerability—

Of the 53 patients enrolled, two first treated in May 2016 were continuing sacituzumab govitecan therapy at the cutoff date of Jan. 31, 2017. All other patients had discontinued treatment and otherwise were being monitored for survival. More than 590 doses (over 295 cycles) have been administered, with a median of 10 doses (range, 1-63) per patient. No infusion-related reactions were reported.

The initial doses in 15 patients were given at a starting dose of 8 mg/kg; 10 mg/kg was the starting dose for the next 38 patients. Between the 2 dose groups, 25 patients received ≥10 doses (≥5 cycles), and 2 received 62 and 63 doses (>30 cycles). The median treatment duration was 2.5 months (range, 1 to 23). Neutropenia (grade ≥2) was the only indication for dose reduction, and was recorded in 29% (11/38) patients at the 10 mg/kg dose level after a median of 2.5 doses (range, 1 to 9). Two of the fifteen patients (13%) treated at 8 mg/kg had reductions, one after 2 doses and another after 41 doses (20 cycles). Once reduced, additional reductions were infrequent. No treatment-related deaths were observed.

In this trial, ten patients dropped out before the first response assessment; four received 1 dose, five received 2 doses, and another after 4 doses. Three were ineligible for response evaluation after receiving 1 or 2 doses, because one had mixed histology of SCLC and NSCLC, and the other 2 were diagnosed with pre-trial brain and/or spinal cord metastases after receiving the first dose of sacituzumab govitecan. Two patients who reported CTCAE grade 3 adverse events (neutropenia and fatigue) after one dose that did not recover in time for the second dose were discontinued per protocol guidelines. Four patients withdrew from the study after 2 doses, 2 withdrew consent and 2 withdrew due to grade 2 fatigue. An additional patient left the study after 4 treatments because of concurrent multiple comorbidities, dying suddenly before the first response assessment.

The most frequently reported AEs in the 53 patients receiving at least one dose of sacituzumab govitecan were nausea, diarrhea, fatigue, alopecia, neutropenia, vomiting and anemia (Table 6). Grade 3 or 4 neutropenia occurred in 34% (18/53) of patients, and only one patient had febrile neutropenia. Other grade 3 or 4 adverse events were few, and included fatigue (13%), diarrhea (9%), anemia (8%), increased alkaline phosphatase (8%), and hyponatremia (8%). While there were fewer patients requiring dose reduction in the 8 mg/kg dose group (13% vs 28% in 10 mg/kg), the 10 mg/kg dose level was equally well tolerated, with dose modification and/or growth factor support in a few patients.

TABLE 6

Frequency of adverse events (N = 53), regardless of causality, occurring in >15% (all grades) or ≥2% (grade ≥3) of patients (ranked by all grades).

| Adverse Events | All Grades | | Grades 3 and 4 | |
| --- | --- | --- | --- | --- |
| (N = 53) | N | % | N | % |
| Diarrhea | 28 | 52.8 | 5 | 9.4 |
| Nausea | 27 | 50.9 | — | — |
| Fatigue | 25 | 47.2 | 7 | 13.2 |
| Neutropenia | 23 | 43.4 | 18 | 34.0 |
| Vomiting | 18 | 34.0 | — | — |
| Abdominal pain | 16 | 30.2 | — | — |
| Anorexia | 15 | 28.3 | — | — |
| Anemia | 14 | 26.4 | 3 | 5.7 |
| Alopecia | 12 | 22.6 | — | — |
| Constipation | 11 | 20.8 | — | — |
| Hypomagnesemia | 10 | 18.9 | — | — |
| Dehydration | 9 | 17.0 | — | — |
| Dyspnoea | 9 | 17.0 | — | — |
| Cough | 8 | 15.1 | — | — |

TABLE 6-continued

Frequency of adverse events (N = 53), regardless of causality, occurring in >15% (all grades) or ≥2% (grade ≥3) of patients (ranked by all grades).

| Adverse Events | All Grades | | Grades 3 and 4 | |
| --- | --- | --- | --- | --- |
| (N = 53) | N | % | N | % |
| Hypoxia | 3 | 5.7 | 2 | 3.8 |
| Febrile neutropenia | 1 | 1.9 | 1 | 1.9 |

Efficacy—

Figure 16:
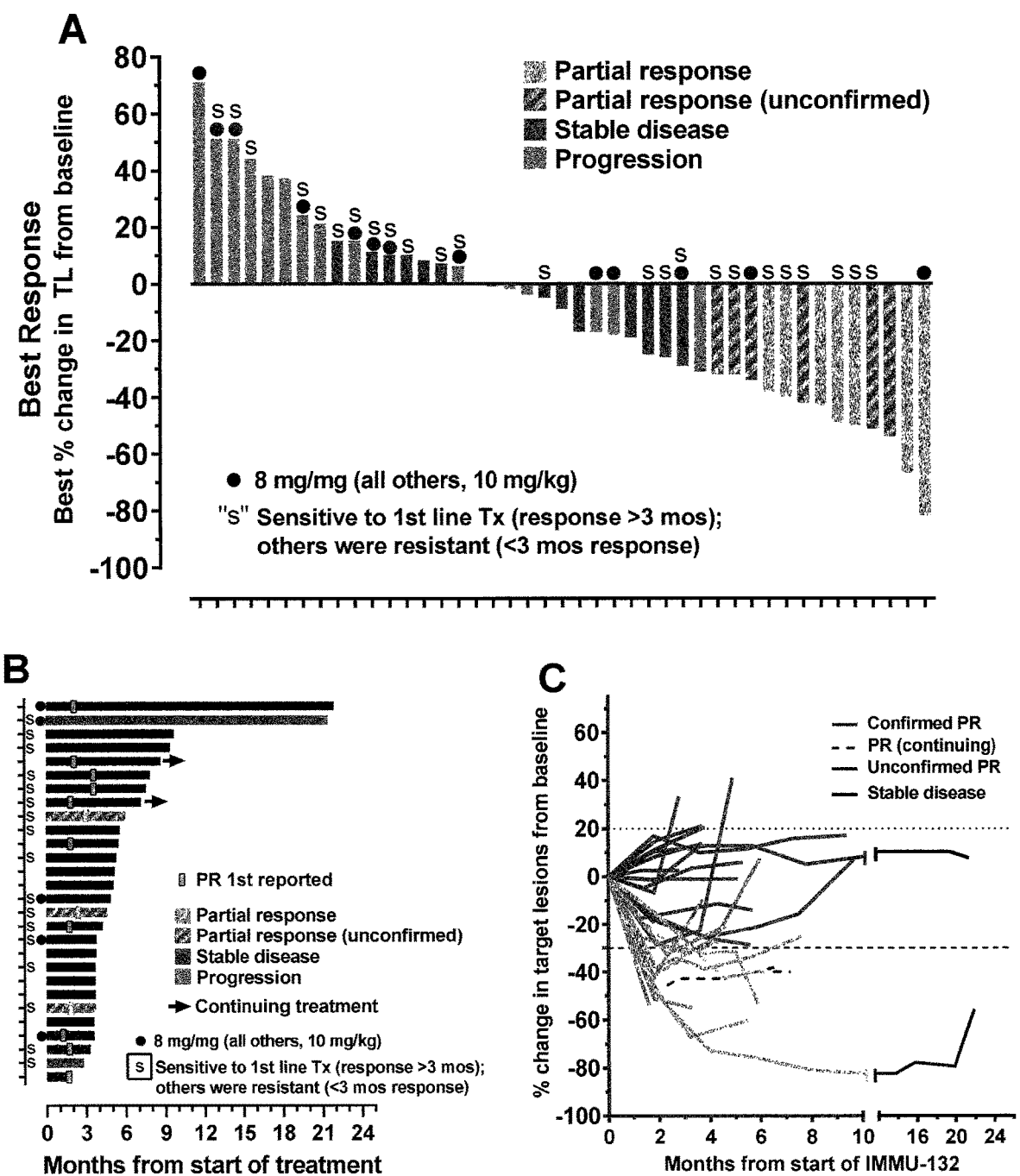
FIG. 16. Graphic representation of anti-tumor response and duration in response-assessable patients. (A) Best percentage change in the sum of the diameters for the selected target lesion and best overall response descriptor according to RECIST 1.1 criteria. Patients are identified with respect to the sacituzumab govitecan starting dose and whether they were sensitive or resistant to prior first-line therapy. Patient with unconfirmed partial responses failed to maintain ≥30% on their next CT assessment 4-6 weeks after the first observed objective response. The best overall response for these patients by RECIST 1.0 is stable disease. (B) Duration of response from the start of treatment for those patients who achieved stable disease or better. Timing when tumor shrinkage achieved ≥30% is shown, along with sacituzumab govitecan starting dose and sensitivity to first-line therapy. (C) Dynamics of response for patients who achieved stable disease or better. Two patients with confirmed partial responses who are continuing treatment are shown with dashed line.

As described, of the 53 mNSCLC patients enrolled, ten discontinued prior to their first CT response assessment, leaving 43 patients with the protocol-required objective assessment of response after receiving at least two doses of sacituzumab govitecan and at least one follow-up scan. FIG. 16 provides a series of graphic representations of the responses, including a waterfall plot of the best percentage change in the diameter sum of the target lesions for the 43 patients (FIG. 16A), a graph showing the duration of the responses for those achieving PR or SD status (FIG. 16B), and a plot tracking the response changes of the patients with PR and SD over time (FIG. 16C).

Twenty-one of the 43 CT-assessable patients (49%) experienced a reduction of tumor size from baseline (FIG. 16A). Confirmed partial responses (≥30% reduction) occurred in seven patients, yielding an ORR of 16% (Table 7). The median time to response in these patients was 2.0 months (range, 1.8 to 3.6 months), with a Kaplan-Meier estimated median duration of response of 5.7 months (95% CI: 3.6, 19.9). Two of the seven responders had ongoing responses at the last follow-up (i.e., patients were alive, free of disease progression, and had not started alternate anticancer treatments), one at 7.2+ months and the other 8.7+ months from start of treatment (FIG. 1B, FIG. 1C).

TABLE 7

Response summary of sacituzumab govitecan (IMMU-132) in SCLC patients

| Best overall response, N (%) | |
| --- | --- |
| Total with response assessment | 43 |
| PR (confirmed) | 7 (16%) |
| PRu (unconfirmed; SD with >30% shrinkage as best response) | 6 (14%) |
| SD | 15 (35%) |
| PD | 15 (35%) |
| Clinical benefit rate (PR + SD ≥4 months) N (%) | 17/43 (40%) |
| Duration of confirmed objective response, months median (95% CI) | 5.7 (3.6, 19.9) |
| Progression-free survival, months (N = 53), median (95% CI) | 3.6 (2.0, 4.3) |
| Overall survival, months (N = 53), median (95% CI) | 7.0 (5.5, 8.3) |
| IMMU-132 response assessment in patients who were sensitive (N = 24) to 1$^{st}$ line. | |
| PFS (median months; 95% CI) | |
| OS (median months; 95% CI) | 3.8 (2.8, 6.0) |
| Clinical benefit rate (PR + SD ≥4 months) N (%) | 8.3 (7.0, 13.2) |
| IMMU-1 32 response assessment in patients who were resistant (N = 19) to 1$^{st}$ line. | 12/24 (50%) |
| PFS (median months; 95% CI) | 3.6 (1.8, 3.8) |
| OS (median months; 95% CI) | 6.2 (4.0, 10.5) |
| Clinical benefit rate (PR + SD ≥4 months) N (%) | 5/19 (26%) |

TABLE 7-continued

Response summary of sacituzumab govitecan (IMMU-132) in SCLC patients

| Patients receiving IMMU-132 as second line (N = 19) | |
|---|---|
| PFS, median months (95% CI) | 3.6 (2.0, 5.3) |
| OS (median months; 95% CI) | 8.1 (7.5, 10.5) |
| Clinical benefit rate (PR + SD ≥4 months) N (%) | 7/19 (37%) |
| Patients receiving IMMU-132 as ≥3 line (N = 24) | |
| PFS, median months (95% CI) | 3.7 (1.8, 5.5) |
| OS (median months; 95% CI) | 7.0 (6.2, 20.9) |
| Clinical benefit rate (PR + SD ≥4 months) N (%) | 9/24 (38%) |
| IMMU-132 given as ≥3 line and Prior topotecan/irinotecan (N = 15) | |
| PFS, median months (95% CI) | 3.6 (3.3, 5.5) |
| OS (median months; 95% CI) | 8.8 (6.2, 20.9) |
| Clinical benefit rate (PR + SD ≥4 months) N (%) | 6/15 (40%) |
| No prior topotecan/irinotecan (N = 9) | |
| PFS, median months (95% CI) | 3.7 (1.7, 4.3) |
| OS (median months; 95% CI) | 5.5 (3.2, 8.3) |
| Clinical benefit rate (PR + SD ≥4 months) N (%) | 3/9 (33%) |

Figure 17:
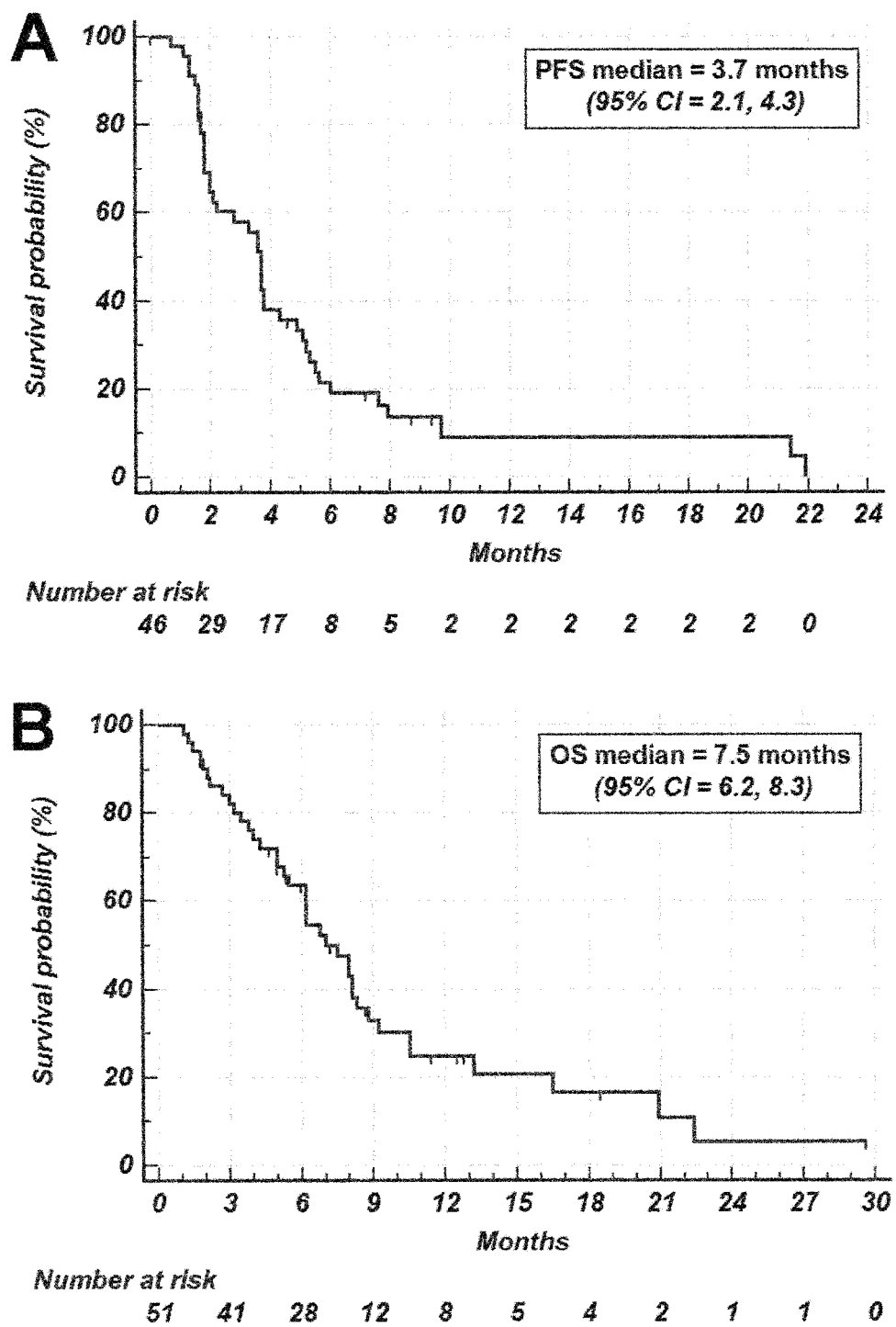
FIG. 17. (A) Kaplan-Meier derived progression-free and (B) overall survival curves for all 53 SCLC patients enrolled in the sacituzumab govitecan trial.

Stable disease (SD) was determined in 21 patients (49%), and included six (14%) who initially had >30% tumor reduction that was not maintained at the subsequent confirmatory CT (unconfirmed PR, or PRu), and three patients who had ≥20% tumor reduction. It is important to note that ten patients had SD for ≥4 months (Kaplan-Meier-derived median=5.6 months, 95% CI: 5.2, 9.7), which was not significantly different from the median PFS for the confirmed PR group (7.9 months, 95% CI: 7.6, 21.9; P=0.1620), and a clinical benefit rate (CBR: PR+SD≥4 months) of 40% (17/43). Indeed, even the OS for these ten SD patients was not significantly different from the seven confirmed PR patients (8.3 months, 95% CI 7.5, 22.4 months vs 9.2 months, 95% CI: 6.2, 20.9, respectively; P=0.5599). This suggests that maintaining SD for a suitable duration (≥4 months) should be an endpoint of interest. On an intention-to-treat (ITT) basis (N=53), the median PFS was 3.6 months (95% CI: 2.0, 4.3) (FIG. 17 (A)), while the median OS was 7.0 months (95% CI: 5.5, 8.3), with 17 patients alive and 5 lost to follow-up (one after 1.8 months, one after 5 months, and three after 11.4-12.8 months) (FIG. 17 (B)).

Thirteen of the 43 patients with an objective response assessment were treated at 8 mg/kg, with one confirmed (8%), one unconfirmed PR, and three SD. In the 10 mg/kg group (N=30), six patients had confirmed PR (20%) and twelve had SD, including five with one CT showing a reduction ≥30% (PRu). The CBR was 47% (14/30), suggesting that the starting dose of 10 mg/kg provided a better overall response.

Twenty-four patients with a response assessment were classified as sensitive to the first line of platinum-based chemotherapy (Table 7). Four (17%) achieved a confirmed PR and nine had SD, including four with a single scan showing a >30% tumor reduction (PRu). Nineteen patients were resistant, with three (16%) having confirmed PR and six with SD, including two with PRu. The median PFS for the chemosensitive and chemoresistant groups was 3.8 months (95% CI: 2.8, 6.0) and 3.6 months (95% CI: 1.8, 3.8), respectively, while the median OS was 8.3 months (95% CI: 7.0, 13.2) and 6.2 months (95% CI: 4.0, 10.5), respectively (Table 7). No significant differences in PFS or OS were found between the chemosensitive and chemoresistant groups (P=0.3981 and P=0.3100, respectively).

Nineteen of the 43 patients received sacituzumab govitecan in the second-line setting, and 3/19 (16%) had a PR and seven SD as best response (two of the latter had one >30% tumor shrinkage). The response seen in these patients was the same as that found for the patients who were given sacituzumab govitecan as their third or higher line of therapy (N=24), with four confirmed PR (16%) and 8 SD, including four SD patients with >30% tumor shrinkage on one CT. No significant differences in duration of the PFS or OS were found (P=0.9538 and P=0.6853, respectively). Response analyses are summarized in Table 7.

Among the five patients who received prior treatment with an immune checkpoint inhibitor (CPI), one experienced an unconfirmed PR (54% shrinkage on first assessment, withdrew consent without additional treatment or assessments), two achieved SD with one having 17% tumor shrinkage lasting 8.7 months and the other no change in tumor size for 3.7 months, one had progressing disease, while the fifth patient withdrew consent after one cycle of sacituzumab govitecan. All of the CPI-treated patients either failed to respond to the CPI or progressed before receiving sacituzumab govitecan, indicating that patients can be responsive to IMMU-132 after receiving CPI-treatment.

Of the 24 patients who received sacituzumab govitecan as third- or later-line therapy, fifteen had previously received topotecan and/or irinotecan, while nine never received these agents. The objective responses in these two groups were similar, with no significant difference in PFS (3.8 vs 3.7 months; P=0.7341). However, those treated with sacituzumab govitecan who received prior topotecan therapy had a significantly longer OS than those who did not (8.8 months, 95% CI: 6.2, 20.9 vs 5.5 months, 95% CI: 3.2, 8.3; P=0.0357). The longer OS in this group may reflect the known activity of topotecan in patients who are platinum-sensitive, and therefore may have a better long-term outcome.

Figure 18:
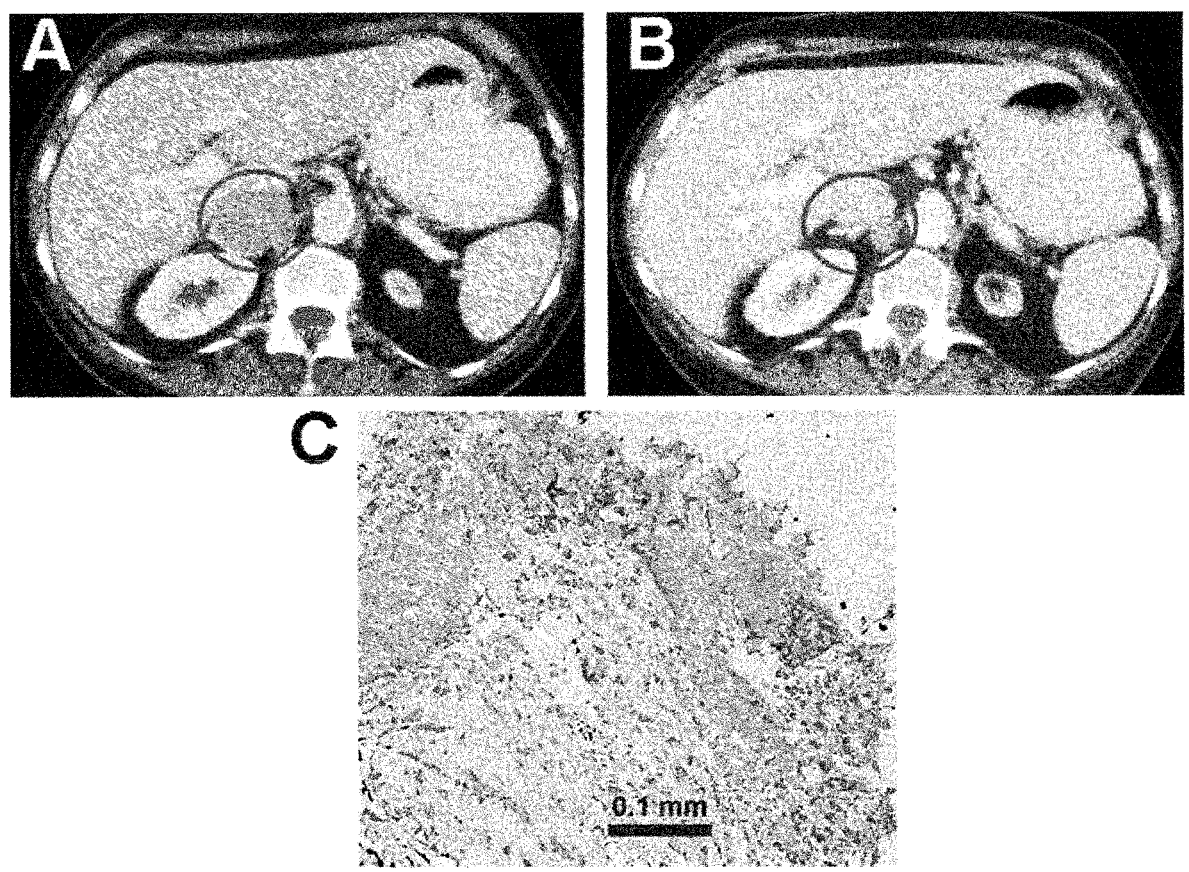
FIG. 18. This 64-year-old male diagnosed with advanced SCLC received carboplatin as $1^{st}$ line therapy from July 2013 to November 2013, with etoposide added in November and December 2013. The disease relapsed in May 2014. Prior to starting sacituzumab govitecan, the tumor lesions at baseline (May 2014) included subcarinal lymph node (20 mm) and right adrenal gland tumors (A) (43×34 mm diameter adrenal mass), as well as multiple unmeasurable lesions in the right and left lobes of the liver, thickening of the right hilum, a left upper lobe pulmonary nodule, and esophageal thickening. The response evaluation after 2 months of therapy showed 50% reduction according to RECIST 1.1 (B) (adrenal mass shrinks to 14 mm, subcarinal lymph node shrinks to 17 mm). By the second response assessment, the adrenal mass was no longer visible, while the subcarinal node experienced its maximum shrinkage ~11 months from the start of treatment (to 11 mm), yielding maximum shrinkage of 82%. The patient experienced a 21-month duration of response (July 2014 to March 2016). (C) Immunohistology of a biopsy from the adrenal mass stained for Trop-2 and scored as 2+, but with sparse distribution among the tumor cells.
Figure 19:
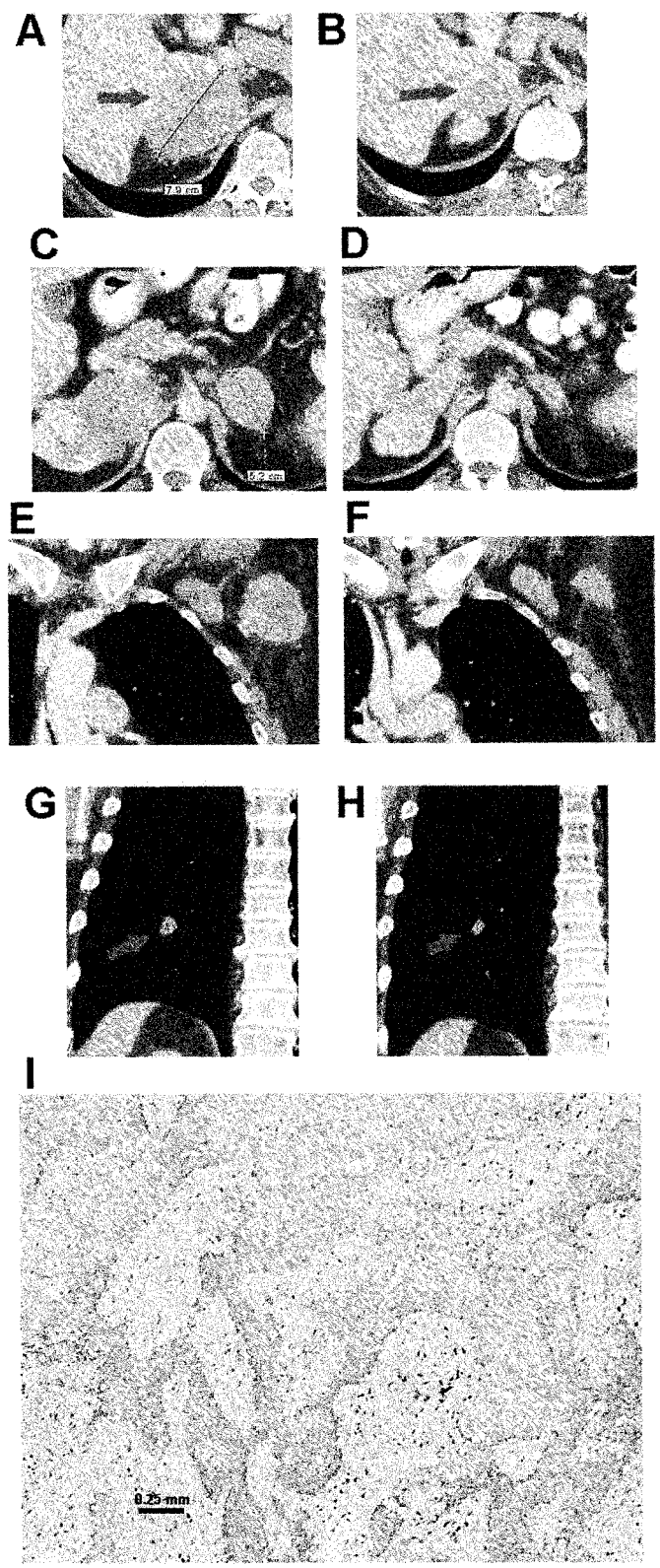
FIG. 19. The Figure shows the effects of IMMU-132 therapy in a 57-year-old male, 1 pack/day smoker since aged 13, who was diagnosed with metastatic small cell neuroendocrine carcinoma in 2012, received carboplatin and etoposide as $1^{st}$ line therapy from October 2012 to January 2013, and upon recurrence, received topotecan from September 2013 to November 2013 with no response. Due to progressing disease, the patient transitioned to a combination of carboplatin and etoposide from November 2013 to April 2014 and further transitioned to paclitaxel from May 2014 to June 2014. In September 2014, he commenced on sacituzumab govitecan achieving a durable response. CT images of 4 of the 5 target lesions from baseline and after 2 months of treatment, when the sum reduced from 230 mm to 138 mm (40% shrinkage), are shown. (A) Axial slice of the right suprarenal mass measuring 79×65 mm at baseline; (B) showing a reduction to 48×26 mm at first assessment. (C) Left adrenal mass measuring 52×38 mm at baseline; (D) 36×17 mm at first assessment. (E) Left axillary mass at baseline shown in coronal plane (60×55 mm) and after 2 months of treatment (F), it shrinks to 30×24 mm. (G) Right upper lobe lung mass shown in coronal plane (21×12 mm) shrinking to 16×12 mm (H). (I) Immunohistology of a lung biopsy stained for Trop-2 with a range of staining of tumor cells from negative to 3+, but overall scored as 2+.

A patient given sacituzumab govitecan after relapsing to first-line carboplatin plus etoposide therapy is presented in FIG. 18. Another example with considerable tumor reduction is shown in FIG. 19.

Immunohistochemical (IHC) Staining of Tumor Specimens—

Archival tumor specimens were obtained from 29 patients, but four were inadequate for review, leaving 25 assessable tumors, of which 92% were positive, with two (8%) having strong (3+) and thirteen (52%) moderate (2+) staining. Twenty-three of these patients had an objective response assessment. There were five with confirmed PR and two unconfirmed PR in this group; five had 2+ staining, while the other two were 1+(not shown), suggesting that higher expression provided better responses. However, an assessment of PFS and OS values against IHC score showed no clear trend (not shown), and Kaplan-Meier estimates for PFS and OS for patients with IHC scores of 0 and 1+ combined (N=10) vs 2+ and 3+ combined (N=13) indicated no significant differences (PFS, P=0.2661; OS, P=0.7186) based on IHC score (not shown).

Immunogenicity of ADC, SN-38, or hRS7 Antibody—

No neutralizing antibodies to sacituzumab govitecan, the antibody, or SN-38 were detected in patients who maintained treatment for even up to 22 months.

Discussion

The relapse of SCLC to frontline chemotherapy continues to be divided into two categories, resistant relapse, occurring within three months of the first platinum-based therapy, and sensitive relapse, which occurs after at least 3 months post treatment (O'Brien et al., 2006, J Clin Oncol 24:5441-7;

Perez-Soler et al., 1996, J Clin Oncol 14:2785-90). Although there is still some ambiguity regarding the best management of recurrent SCLC, topotecan, a topoisomerase-I inhibitor similar to the SN-38 used in the ADC studied here, is the only product approved for chemosensitive relapse, as supported by numerous trials (O'Brien et al., 2006, J Clin Oncol 24:5441-7; Horita et al., 2015, Sci Rep 5:15437). However, the efficacy and adverse events of topotecan have varied considerably in prior studies, as demonstrated in a meta-analysis of over a thousand patients reported in 14 articles that topotecan had an objective response rate of 5% in chemoresistant frontline patients and 17% in chemosensitive patients (Horita et al., 2015, Sci Rep 5:15437). There were grade ≥3 neutropenia, thrombocytopenia, and anemia in 69%, 1%, and 24% of patients, respectively, and approximately 2% of patients died from this chemotherapy (Horita et al., 2015, Sci Rep 5:15437). Thus, topotecan shows some promise in this second-line setting in patients who relapsed after showing sensitivity to a platinum-based chemotherapy, but with considerable hematological toxicity. However, even this conclusion was challenged recently by Lara et al. (2015, J Thorac Oncol 10:110-5), who asserted that platinum-sensitivity is not strongly associated with improved PFS and OS following treatment with topotecan, which is its currently approved indication.

It is in this setting that the results reported here with sacituzumab govitecan in extended, advanced-disease patients (stage IV) following a median of 2 (range, 1 to 7) prior therapies are promising. Forty-nine percent of patients showed a reduction of tumor measurements from baseline, according to RECIST 1.1, with an ORR of 16% and a median duration of response of 5.7 months (95% CI: 3.6, 19.9). Stable disease was found in 35% of patients, where 14% of these SD patients had >30% tumor shrinkage as best response, although not maintained on the second scan. The clinical benefit rate at ≥4 months was 40%. Median PFS and OS were 3.6 and 7.0 months, respectively. It is interesting that the median OS for the ten patients with SD was 8.3 months (95% CI: 7.5, 22.4), which is not statistically different from the median OS of 9.2 months (95% CI: 6.2, 20.9) for patients with a PR (P=0.5599). In the group receiving 10 mg/kg as their starting dose (N=30), there was a confirmed objective response in six (20%), with an additional five patients having a single CT showing ≥30% tumor reduction (PRu). Also, the clinical benefit rate for this group at the 10 mg/kg dose was 47%. This supports the preferred dose of 10 mg/kg. Noteworthy also is the lack of patient selection required based on immunohistochemical staining of tumor Trop-2, although there was a suggestion that stronger staining correlated with better response, but no significant difference in PFS or OS was found with regard to IHC score.

As mentioned, PFS and OS did not differ substantially between patients with SD>4 months or PR. Patients with unconfirmed PR (i.e., >30% tumor reduction on one CT) or with SD generally are not considered in most ORR assessments. However, the results here indicate no difference in duration of response between patients with confirmed PR or SD lasting for more than 4 months (FIG. 16B). Indeed, the dynamic tracking of the individual patient responses for PR or SD (especially when the SD last ≥4 months, which is a similar time frame for confirming PR) suggests a clinical benefit for both groups by remaining below the baseline tumor size for several months (FIG. 16C). Although there was a trend for the PFS of patients with confirmed PR to be longer than the group of patients with SD lasting ≥4 months (P=0.1620), the OS for these 2 groups was not significantly different (P=0.5599). Therefore, while the number of patients in this initial analysis is relatively small, the data suggest that more consideration should be given to disease stabilization as an important indicator of clinical activity when an appropriate duration is achieved, similar to follow-up for patients receiving immune checkpoint inhibitors.

Evaluating patients based on prior chemosensitivity (N=24) or chemoresistance (N=19) shows no response differences with sacituzumab govitecan treatment (Table 7). PFS and OS results were 3.8 and 8.3 months for patients who were chemosensitive in first-line, compared to a PFS and OS of 3.6 months and 6.2 months, respectively, for the chemoresistant group. With no statistical difference, it appears that sacituzumab govitecan can be administered to patients in second- or later-line therapies irrespective of the patients being chemosensitive or chemoresistant to first-line chemotherapy. This differs from topotecan, which is indicated only in those SCLC patients who showed a ≥3-month response to first-line cisplatin and etoposide chemotherapy ((O'Brien et al., 2006, J Clin Oncol 24:5441-7; Perez-Soler et al., 1996, J Clin Oncol 14:2785-90). Of 28 patients studied by Perez-Solar et al. (1996, J Clin Oncol 14:2785-90), 11% had a PR, with a median survival of 5 months and a one-year survival of 3.5%.

Although both topotecan and SN-38 are inhibitors of the DNA topoisomerase I enzyme, which is responsible for relaxing a supercoiled DNA helix when DNA is synthesized by stabilizing the DNA complex, causing accumulation of single strand DNA breaks (Takimoto & Arbuck, 1966, Camptothecins. In: Chabner & Long (Eds.). *Cancer Chemotherapy and Biotherapy*. Second ed. Philadelphia: Lippincott-Raven; p. 463-84), sacituzumab govitecan showed activity in patients who relapsed after topotecan therapy. Thus, topotecan resistance or relapse may not be a contraindication for administering sacituzumab govitecan, and because of being similarly active in patients who were chemoresistant to cisplatin and etoposide, may be of particular value as a second-line therapeutic in patients with metastatic SCLC regardless of chemosensitivity status.

In the twenty years since the approval of topotecan in the second-line setting, no new agent has been licensed for metastatic SCLC therapy in second-line or later therapy. However, there has been progress more recently with inhibitors of the T-cell checkpoint receptors programmed cell-death protein (PD-1) and cytotoxic T-lymphocyte-associated protein 4 (CTLA-4) (Antonia et al., 2016, Lancet Oncol 17:883-95). These authors conducted a phase I-II trial of nivolumab with or without CTLA-4 antibody ipilimumab in patients with recurrent SCLC. Nivolumab alone achieved a 10% response rate, while the combination had response rates of 19 to 23%, and a disease-control rate of 32% (Antonia et al., 2016, Lancet Oncol 17:883-95). However, a recent study of ipilimumab with or without chemotherapy in SCLC failed to confirm these results (Reck et al., 2016, J Clin Oncol 34:3740-48). Since we observed that sacituzumab govitecan may have activity in patients failing therapy with immune checkpoint inhibitors, we are studying this further, especially because of evidence showing such responses after therapy with an immune checkpoint inhibitor in patients with other cancer types (Bardia et al., 2017, J Clin Oncol 35:2141-48; Faltas et al., 2016, Clin Genitourin Cancer 14:e75-9; Heist et al., 2017, J Clin Oncol 35:2790-97; Tagawa et al., 2017, J Clin Oncol 35:abstract 327).

Despite recent progress in immunotherapy and the identification of other novel targets for SCLC (Rudin et al., 2017, Lancet Oncol 18:42-51), this still is a lethal disease, especially in the population that is chemoresistant to first-line therapy. The current results of sacituzumab govitecan in heavily-pretreated patients with advanced, relapsed, stage IV, SCLC suggest that this ADC is of use in the therapy of both chemosensitive and chemoresistant SCLC patients, both before or after topotecan.

It will be apparent to those skilled in the art that various modifications and variations can be made to the products, compositions, methods and processes of this invention. Thus, it is intended that the present invention cover such modifications and variations, provided they come within the scope of the appended claims and their equivalents.

What is claimed is:

1. A method of treating small cell lung cancer (SCLC) comprising (i) administering to a human patient with SCLC an anti-Trop-2 antibody-drug conjugate (ADC) wherein the anti-Trop-2 ADC is sacituzumab govitecan, and (ii) administering to the patient cisplatin or carboplatin;
wherein the ADC and cisplatin or carboplatin are administered as a second-line or later therapy to patients who have received previous cancer treatment for the SCLC.

2. The method of claim 1, wherein the cancer is metastatic (mSCLC).

3. The method of claim 1, wherein the patient has previously relapsed from or been resistant to treatment with a standard anti-cancer agent.

4. The method of claim 1, wherein the patient has previously relapsed from or been resistant to treatment with topotecan or irinotecan.

5. The method of claim 1, wherein the SCLC is sensitive to chemotherapy with platinum-containing agents.

6. The method of claim 1, wherein the SCLC is resistant to chemotherapy with platinum-containing agents.

7. The method of claim 1, wherein the treatment results in a reduction in tumor size of at least 15%, at least 20%, at least 30%, or at least 40%.

8. The method of claim 2, further comprising reducing in size or eliminating the metastases.

9. The method of claim 1, wherein the cancer is refractory to other therapies but responds to the ADC.

10. The method of claim 1, wherein the ADC dosage is administered to the human subject once or twice a week on a schedule with a cycle selected from the group consisting of: (i) weekly; (ii) every other week; (iii) one week of therapy followed by two, three or four weeks off; (iv) two weeks of therapy followed by one, two, three or four weeks off; (v) three weeks of therapy followed by one, two, three, four or five weeks off; (vi) four weeks of therapy followed by one, two, three, four or five weeks off; (vii) five weeks of therapy followed by one, two, three, four or five weeks off; and (viii) monthly.

11. The method of claim 10, wherein the cycle is repeated 4, 6, 8, 10, 12, 16 or 20 times.

12. The method of claim 1, wherein the ADC is administered in combination with one or more therapeutic modalities selected from the group consisting of an unconjugated antibody, an immunoconjugate, gene therapy, chemotherapy, a therapeutic peptide, cytokine therapy, localized radiation therapy, surgery, interference RNA therapy, a drug, a toxin and a cytokine.

13. The method of claim 12, wherein the drug, toxin or chemotherapeutic agent is selected from the group consisting of 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatinum (CDDP), Cox-2 inhibitors, irinotecan (CPT-11), SN-38, carboplatin, cladribine, camptothecans, cyclophosphamide, crizotinib, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, flavopiridol, floxuridine (FUdR), 3',5'-O-dioleoyl-FudR (FUdR-dO), fludarabine, flutamide, farnesyl-protein transferase inhibitors, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839.

* * * * *